(12) United States Patent
Shima et al.

(10) Patent No.: US 10,302,626 B2
(45) Date of Patent: May 28, 2019

(54) METHOD FOR EVALUATING COAGULATION ABILITY OF BLOOD SPECIMEN, AND REAGENT, REAGENT KIT AND DEVICE TO BE USED THEREIN

(71) Applicants: PUBLIC UNIVERSITY CORPORATION NARA MEDICAL UNIVERSITY, Kashihara-shi, Nara (JP); CHUGAI SEIYAKU KABUSHIKI KAISHA, Tokyo (JP); SYSMEX CORPORATION, Kobe-shi, Hyogo (JP)

(72) Inventors: Midori Shima, Kashihara (JP); Keiji Nogami, Kashihara (JP); Tomoko Matsumoto, Kashihara (JP); Takehisa Kitazawa, Tokyo (JP); Tetsuhiro Soeda, Tokyo (JP); Yuka Ikeda, Kobe (JP)

(73) Assignees: PUBLIC UNIVERSITY CORPORATION NARA MEDICAL UNIVERSITY, Nara (JP); CHUGAI SEIYAKU KABUSHIKI KAISHA, Tokyo (JP); SYSMEX CORPORATION, Hyogo (JP)

( * ) Notice: Subject to any disclaimer, the term of this patent is extended or adjusted under 35 U.S.C. 154(b) by 0 days.

(21) Appl. No.: 15/791,551

(22) Filed: Oct. 24, 2017

(65) Prior Publication Data
US 2018/0045709 A1 Feb. 15, 2018

Related U.S. Application Data

(63) Continuation of application No. PCT/JP2016/060566, filed on Mar. 30, 2016.

(30) Foreign Application Priority Data

Apr. 24, 2015 (JP) ................. 2015-089865

(51) Int. Cl.
| | |
|---|---|
| G01N 33/49 | (2006.01) |
| G01N 33/86 | (2006.01) |
| C12Q 1/56 | (2006.01) |
| G01N 21/59 | (2006.01) |
| G01N 21/51 | (2006.01) |
| B01L 3/00 | (2006.01) |

(52) U.S. Cl.
CPC ............ *G01N 33/4905* (2013.01); *B01L 3/00* (2013.01); *C12Q 1/56* (2013.01); *G01N 21/51* (2013.01); *G01N 21/59* (2013.01); *G01N 33/86* (2013.01); *G01N 2201/122* (2013.01)

(58) Field of Classification Search
None
See application file for complete search history.

(56) References Cited

U.S. PATENT DOCUMENTS

| 2008/0138843 A1 | 6/2008 | Nowak et al. |
| 2014/0295470 A1 | 10/2014 | Okuda et al. |
| 2015/0240287 A1 | 8/2015 | Soeda et al. |

FOREIGN PATENT DOCUMENTS

| CN | 104076156 A | 10/2014 |
| JP | 2004-191320 A | 7/2004 |
| JP | 2008-530992 A | 8/2008 |
| JP | 2010-217059 A | 9/2010 |
| JP | 2012-048586 A | 3/2012 |
| JP | 2013-053960 A | 3/2013 |
| JP | 2014190954 A | 10/2014 |
| WO | 2014/050926 A1 | 4/2014 |

OTHER PUBLICATIONS

Douxfils, Jonathan, et al. "Assessment of the impact of rivaroxaban on coagulation assays: laboratory recommendations for the monitoring of rivaroxaban and review of the literature." Thrombosis research 130.6 (2012): 956-966. (Year: 2012).*
Matsumoto, T., et al. "The measurement of low levels of factor VIII or factor IX in hemophilia A and hemophilia B plasma by clot waveform analysis and thrombin generation assay." Journal of thrombosis and haemostasis 4.2 (2006): 377-384. (Year: 2006).*
Matsumoto, Tomoko, et al. "A modified thrombin generation test for investigating very low levels of factor VIII activity in hemophilia A." International journal of hematology 90.5 (2009): 576. (Year: 2009).*
A. Muto et al., "Anti-factor IXa/X antibody (ACE910): hemostatic potency against ongoing bleeds in a hemophilia A model and the possibility of routine supplementation", Journal of Thrombosis and Haemostasis, Feb. 2014, 20 pages, vol. 12, No. 2.
T. Matsumoto et al., "A novel bispecific antibody (ACE910) against coagulation factors IXa and X improves procoagulant activity of patients with hemophilia A ex vivo to hemostatic level", ISTH, OC 37.3. Jul. 2, 2013, 19 pages.
International Search Report for PCT/JP2016/060566 dated Jun. 28, 2016 [PCT/ISA/210].
International Preliminary Report on Patentability dated Oct. 26, 2017 for PCT/JP2016/060566 filed Mar. 30, 2016.

* cited by examiner

*Primary Examiner* — Robert J Yamasaki
(74) *Attorney, Agent, or Firm* — Sughrue Mion, PLLC

(57) ABSTRACT

The present invention relates to a method for evaluating coagulability of a blood specimen obtained from a subject to whom a substance having a coagulation factor VIII-substituting activity is administered. The present invention also relates to a reagent for blood coagulation analysis, a reagent kit for blood coagulation analysis, and an apparatus for blood coagulation analysis. Furthermore, the present invention relates to an apparatus and computer program for evaluating coagulability of a blood specimen.

7 Claims, 72 Drawing Sheets

[Fig. 1]
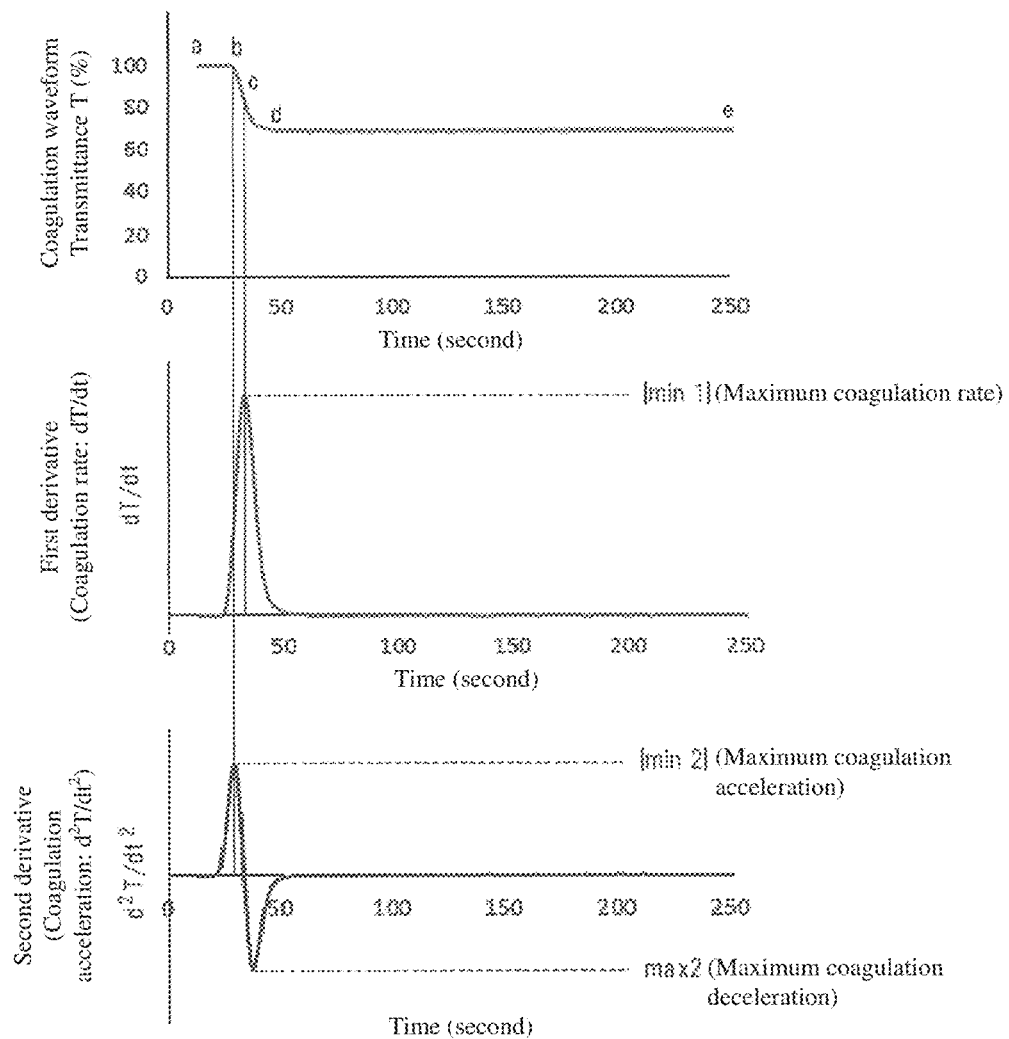
[Fig. 2]
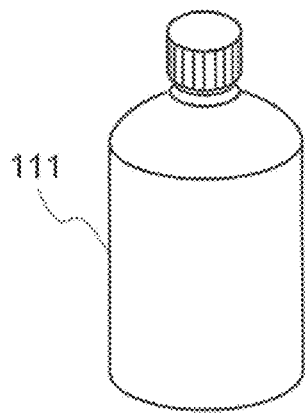

[Fig. 3A]
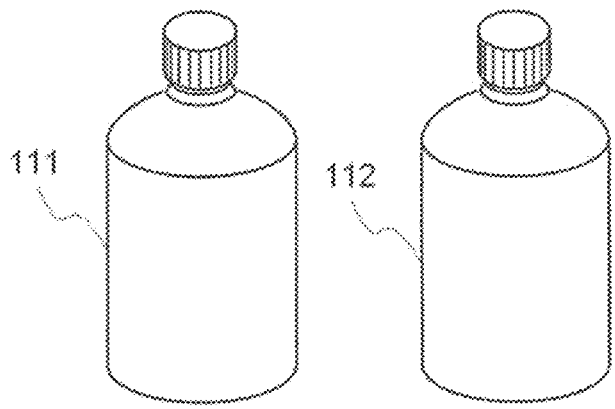
[Fig. 3B]
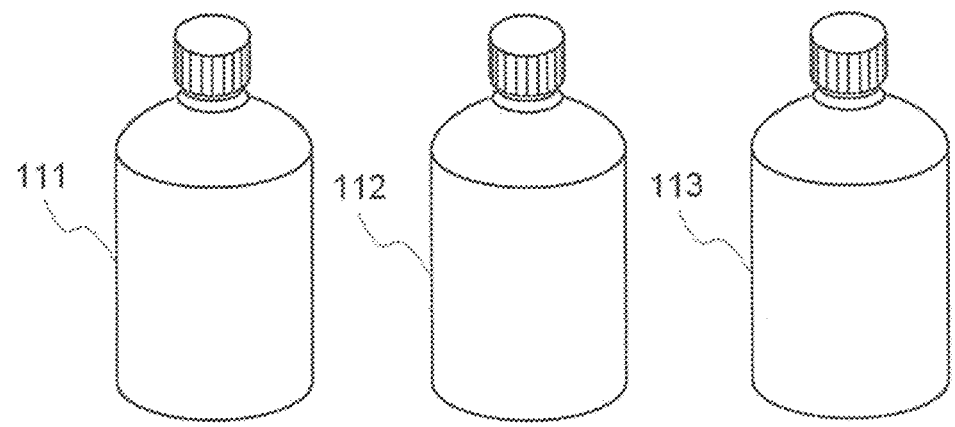

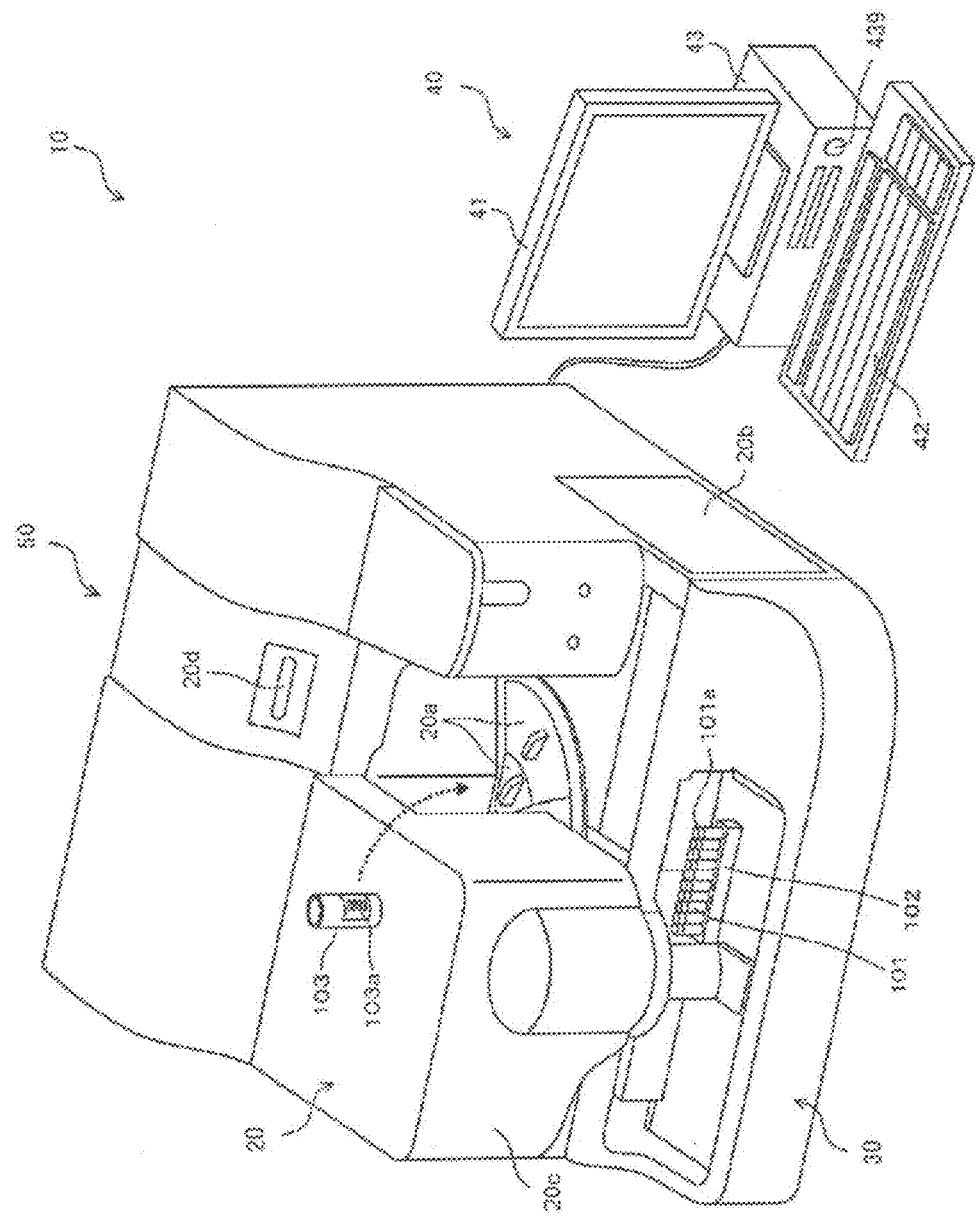
[Fig. 4]

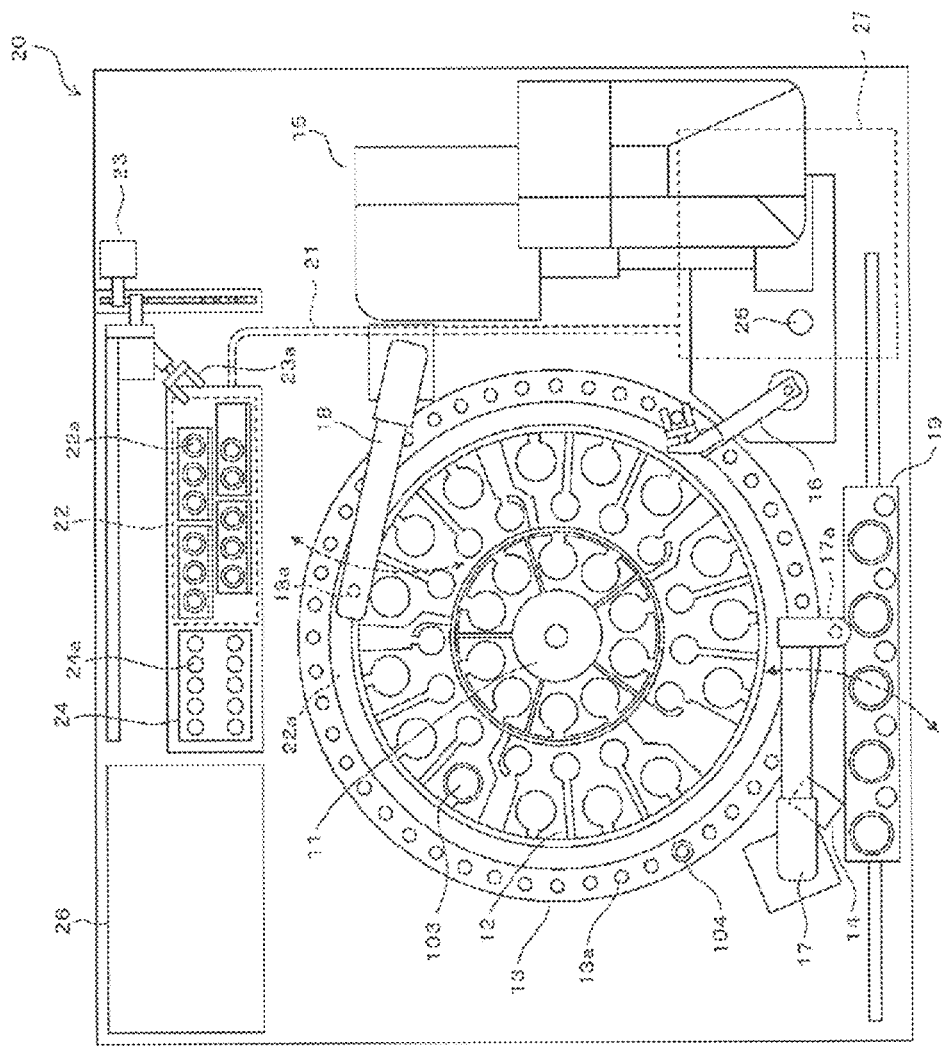
[Fig. 5]

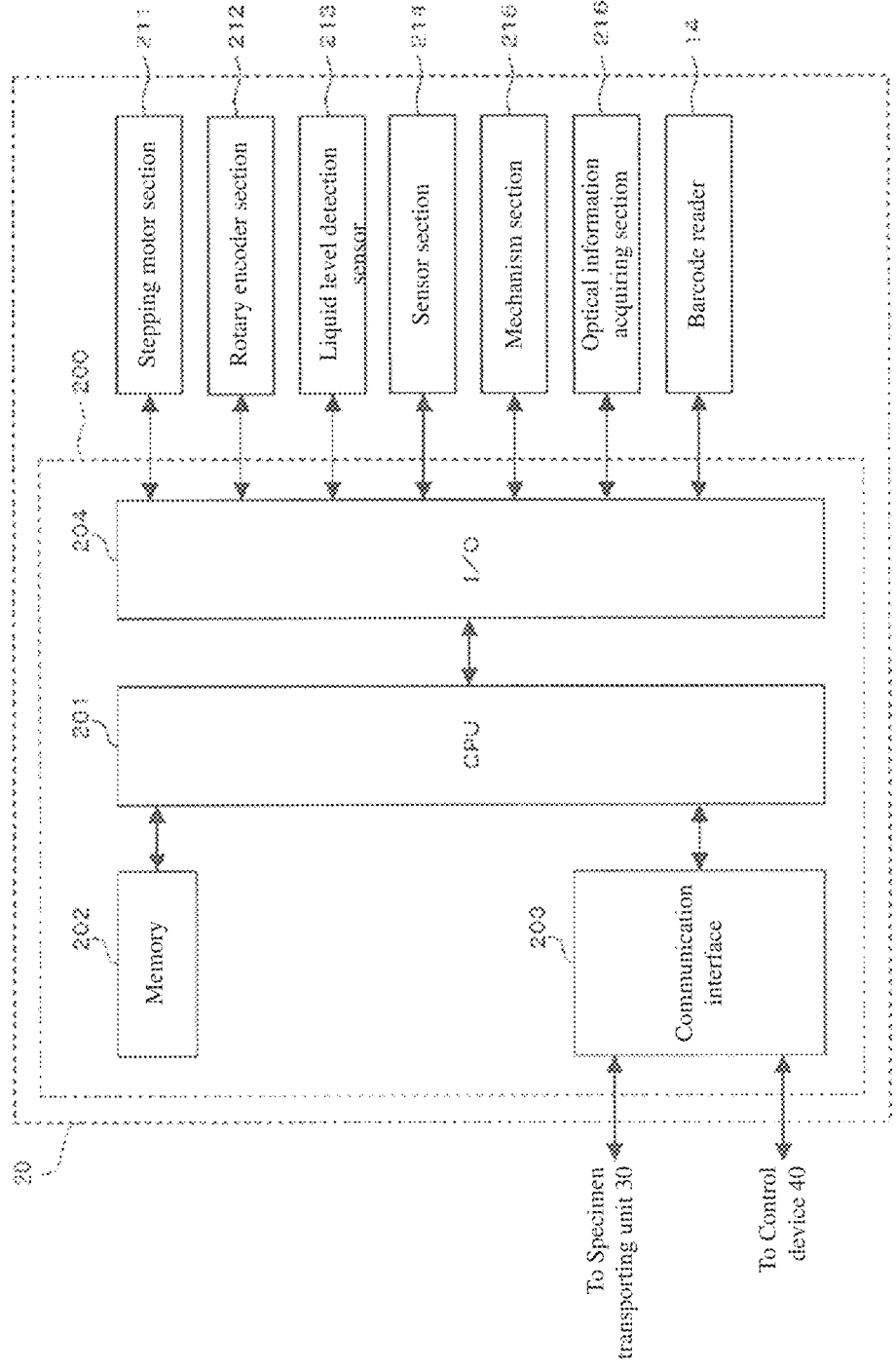
[Fig. 6]

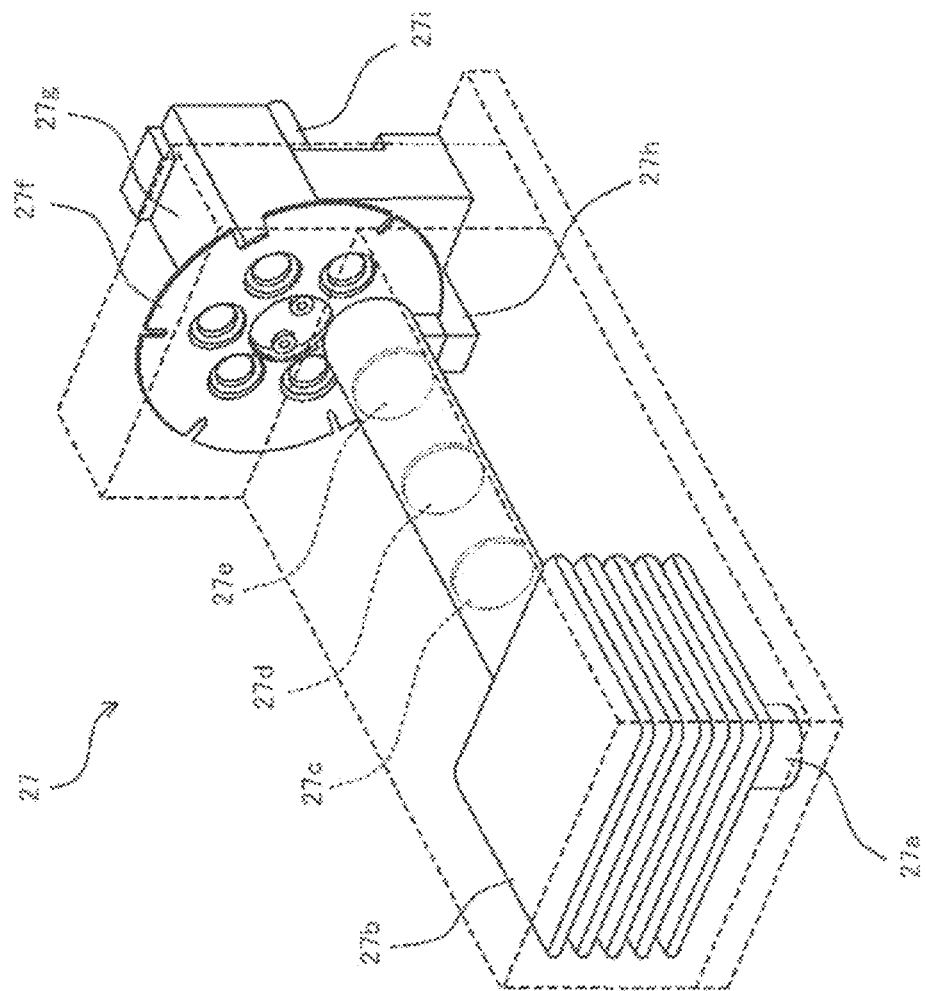
[Fig. 7]

[Fig. 8A]
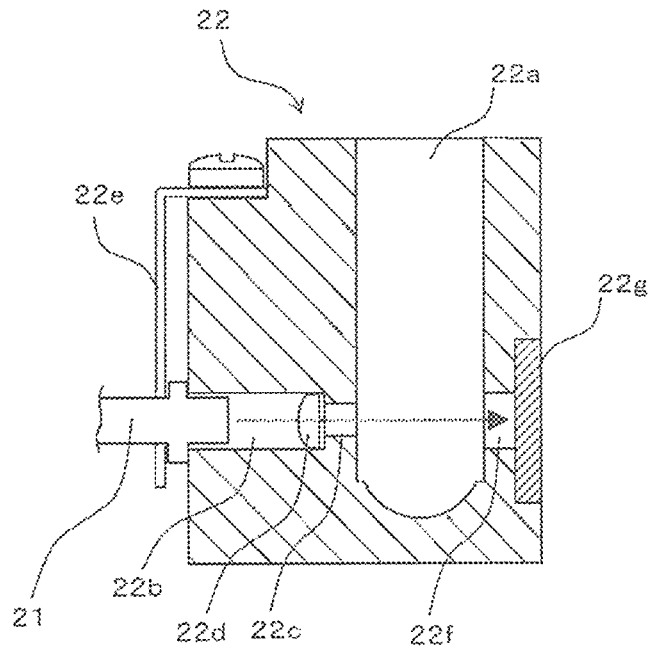
[Fig. 8B]
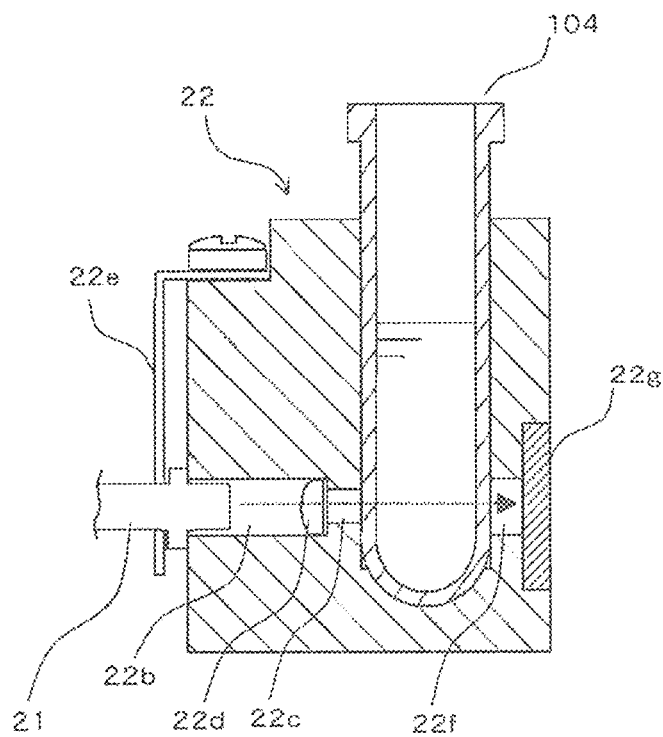

[Fig. 8C]
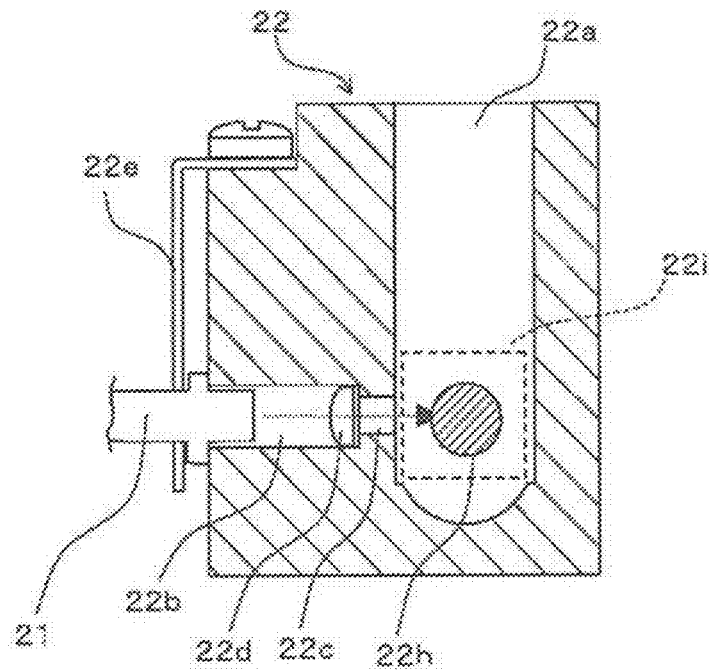
[Fig. 8D]
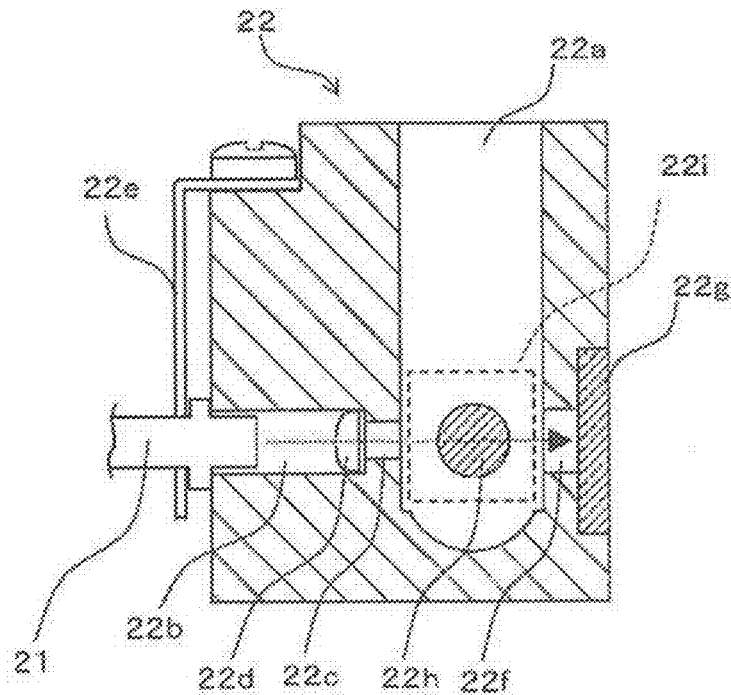

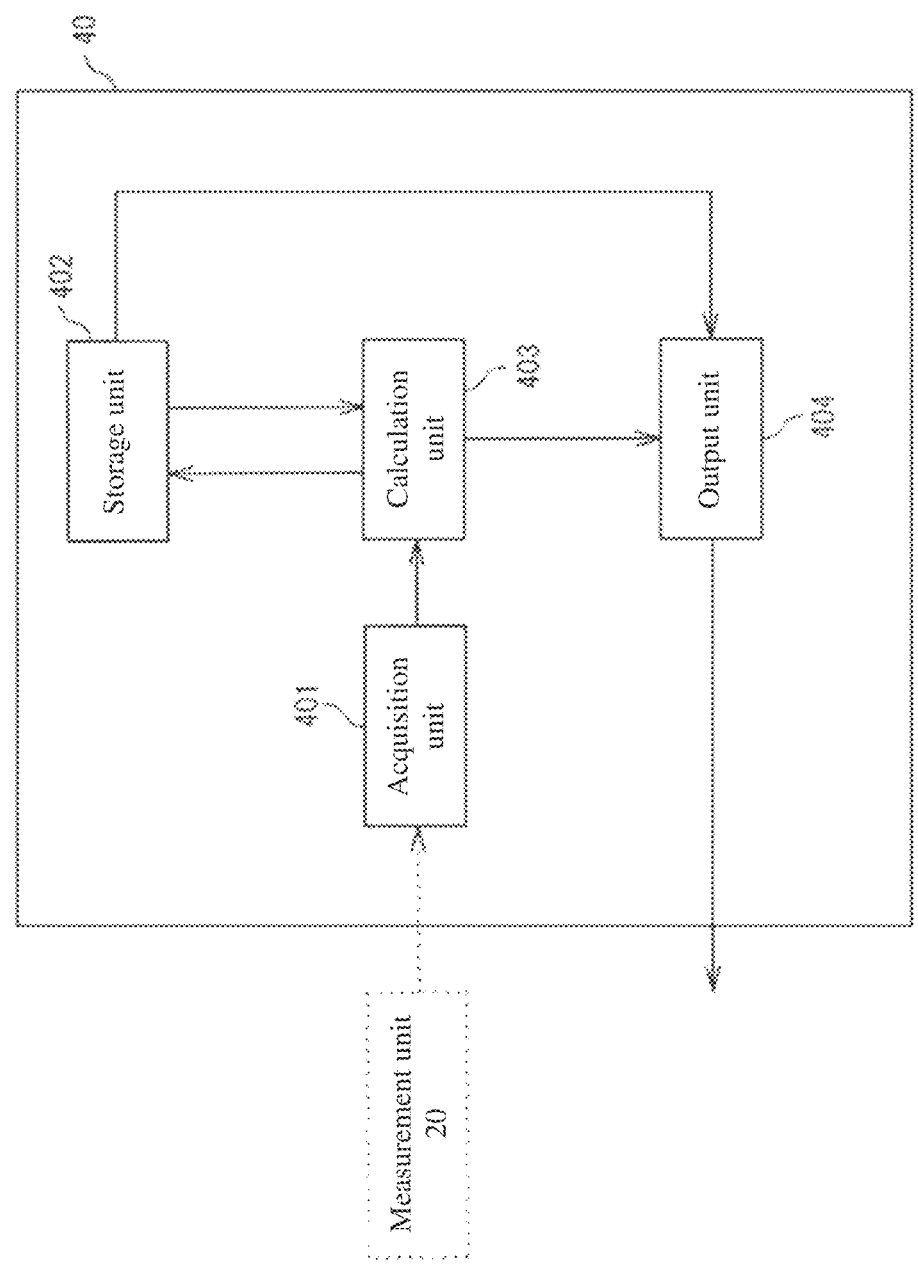
[Fig. 9]

[Fig. 10]
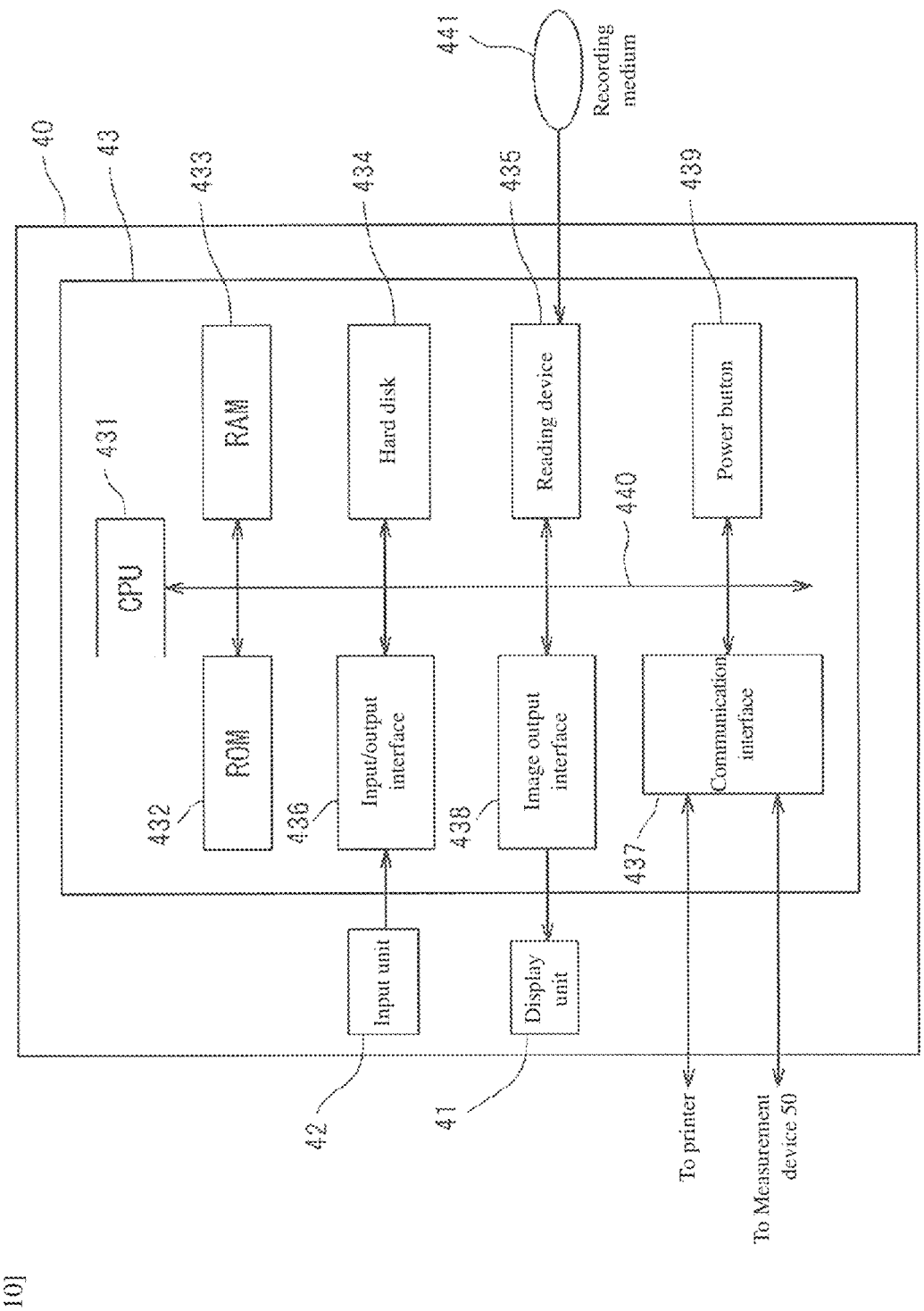

[Fig. 11]
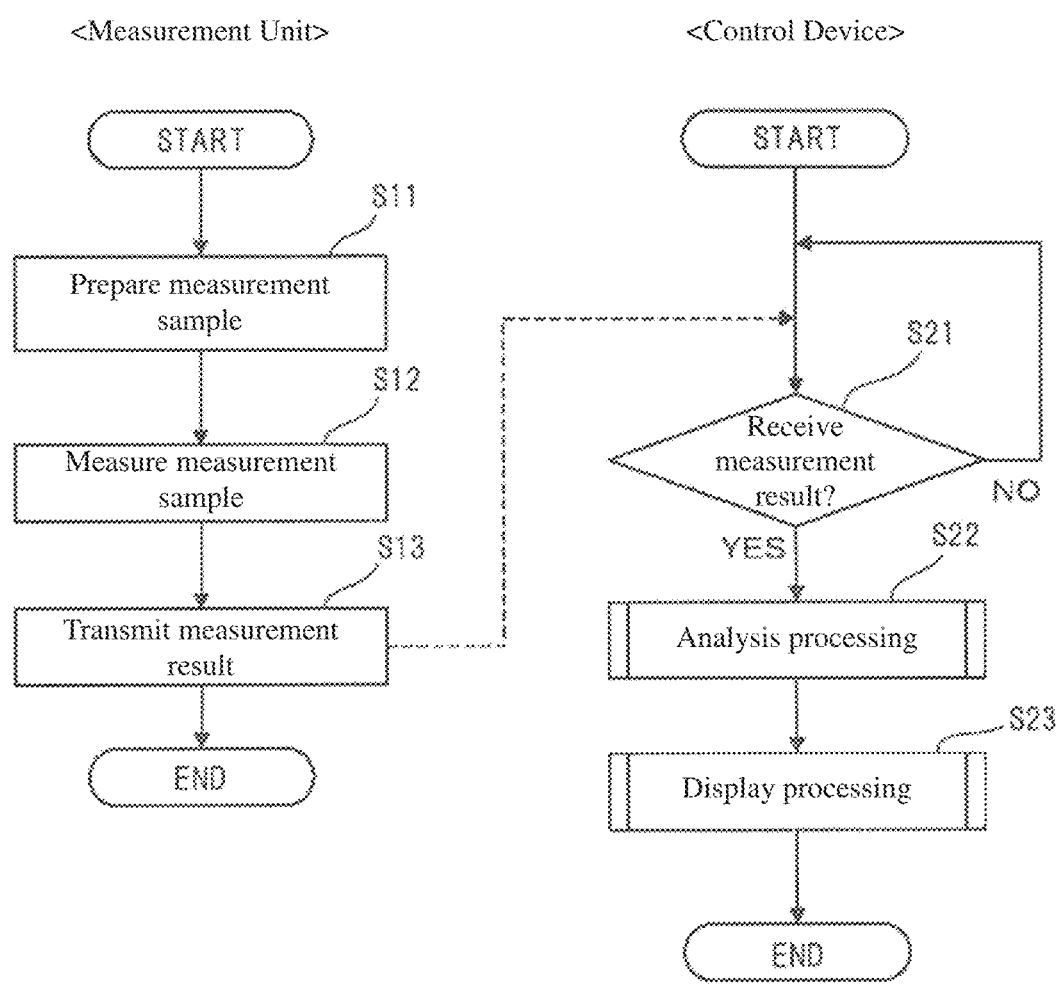

[Fig. 12]
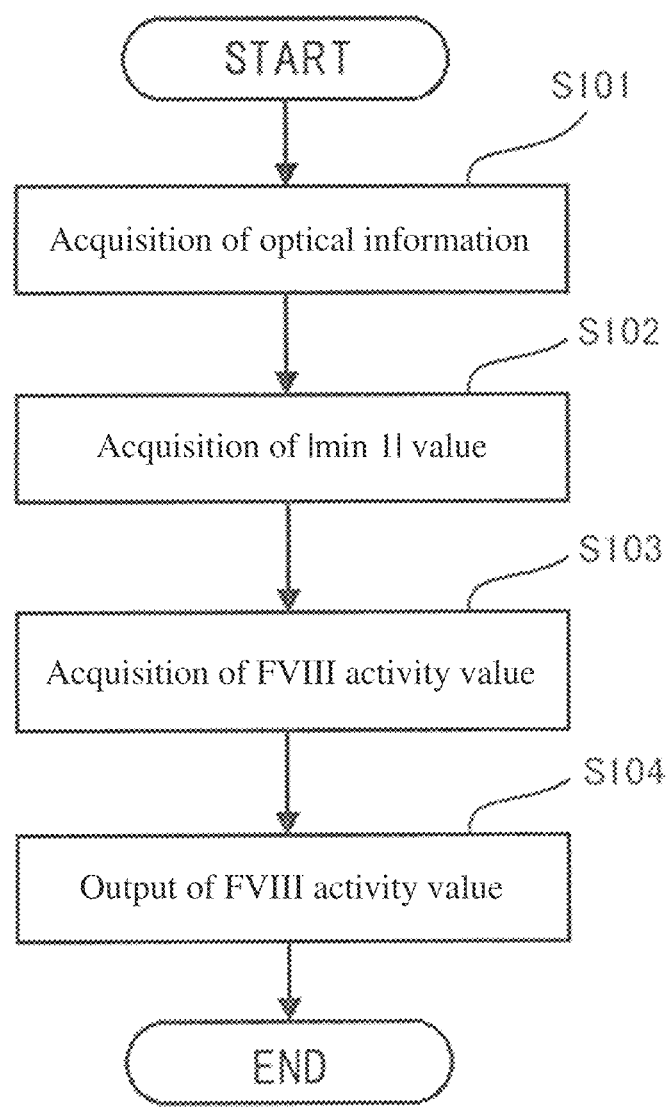

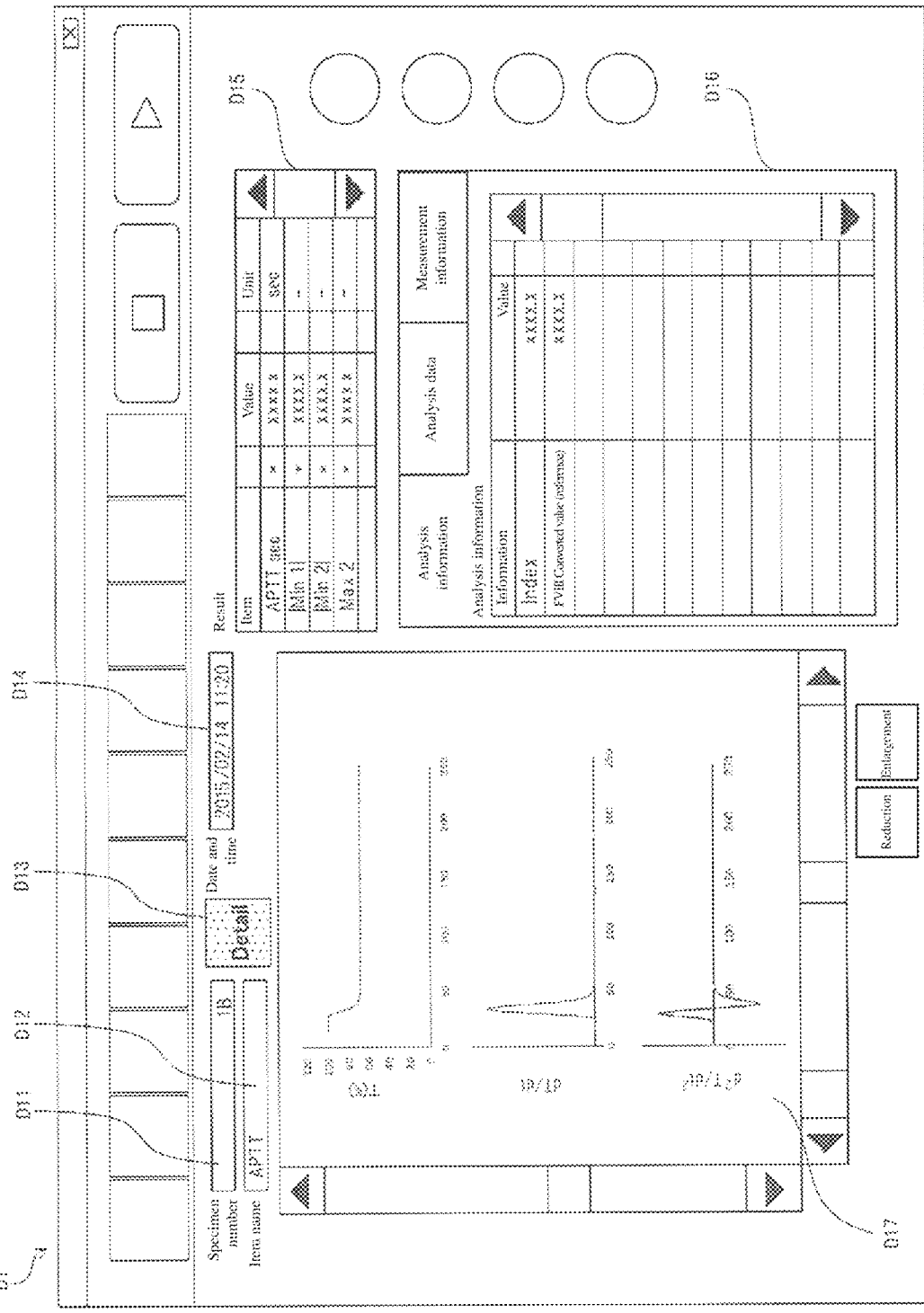
[Fig. 13]

[Fig. 14A]
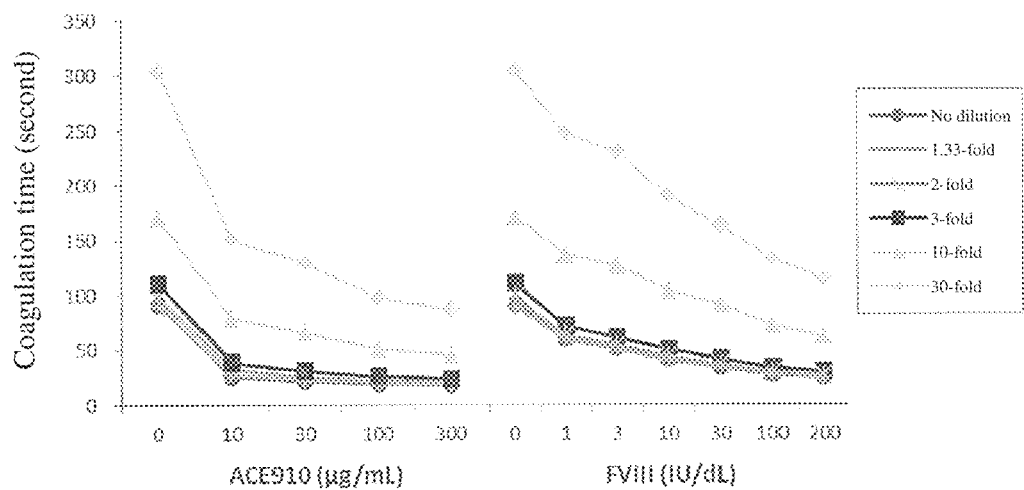
[Fig. 14B]
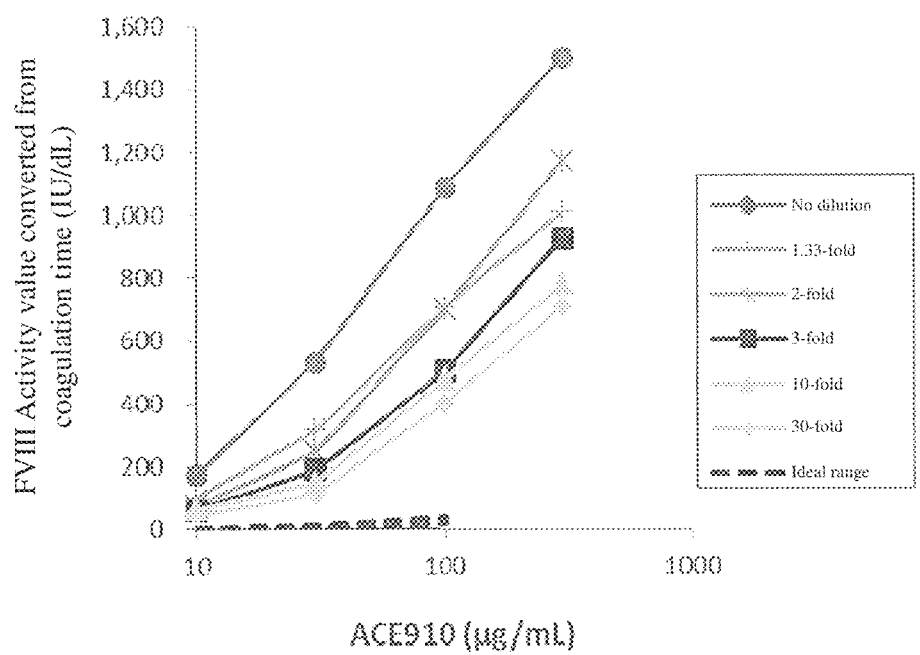

[Fig. 15A]
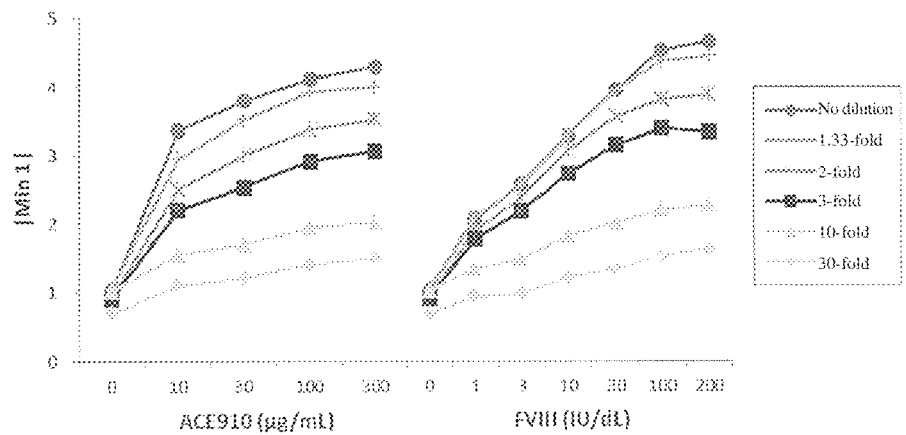
[Fig. 15B]
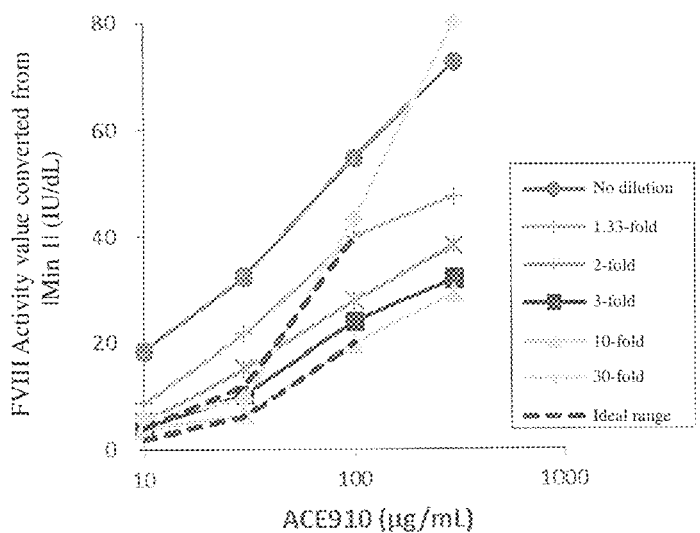
[Fig. 16A]
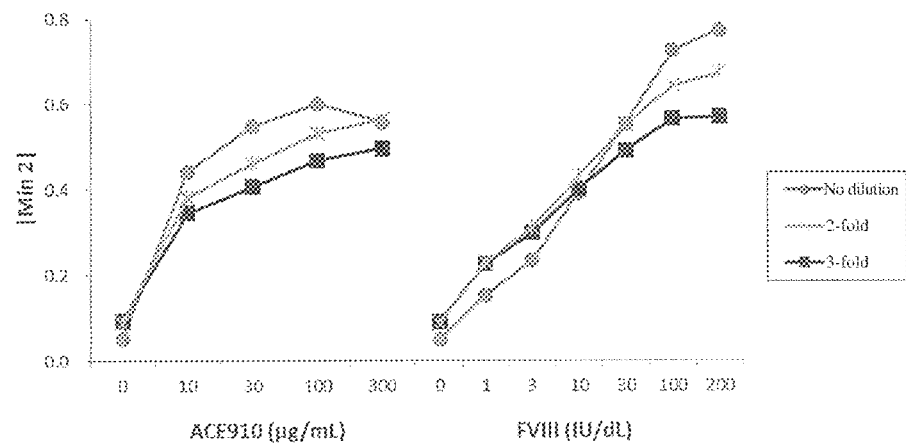

[Fig. 16B]
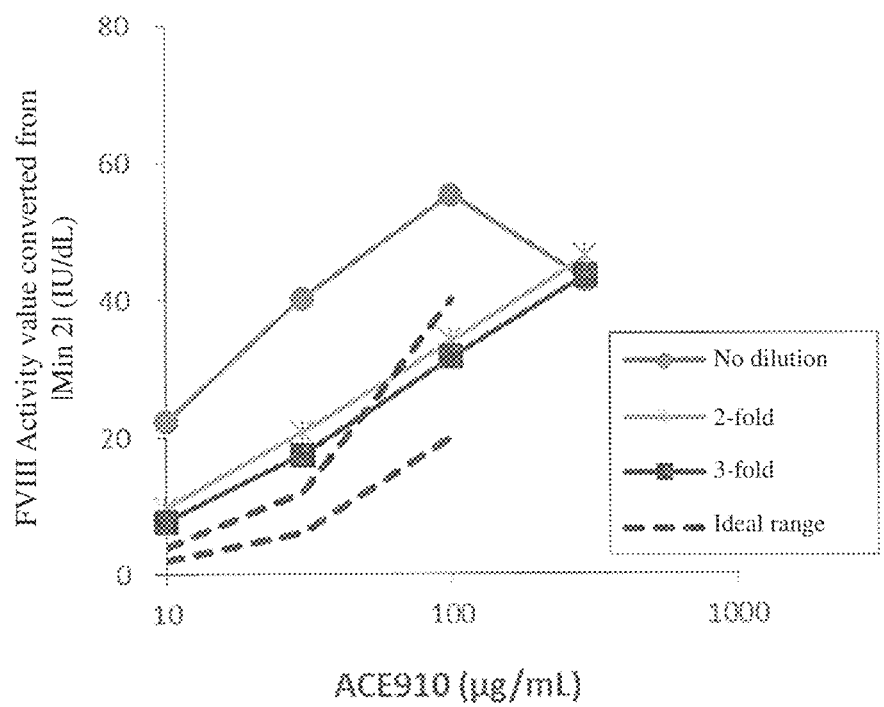
[Fig. 17A]
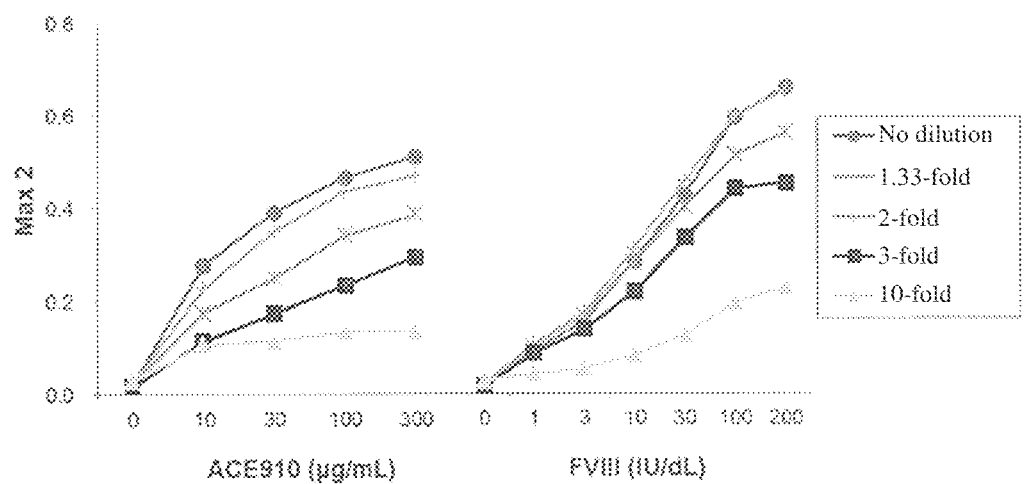

[Fig. 17B]
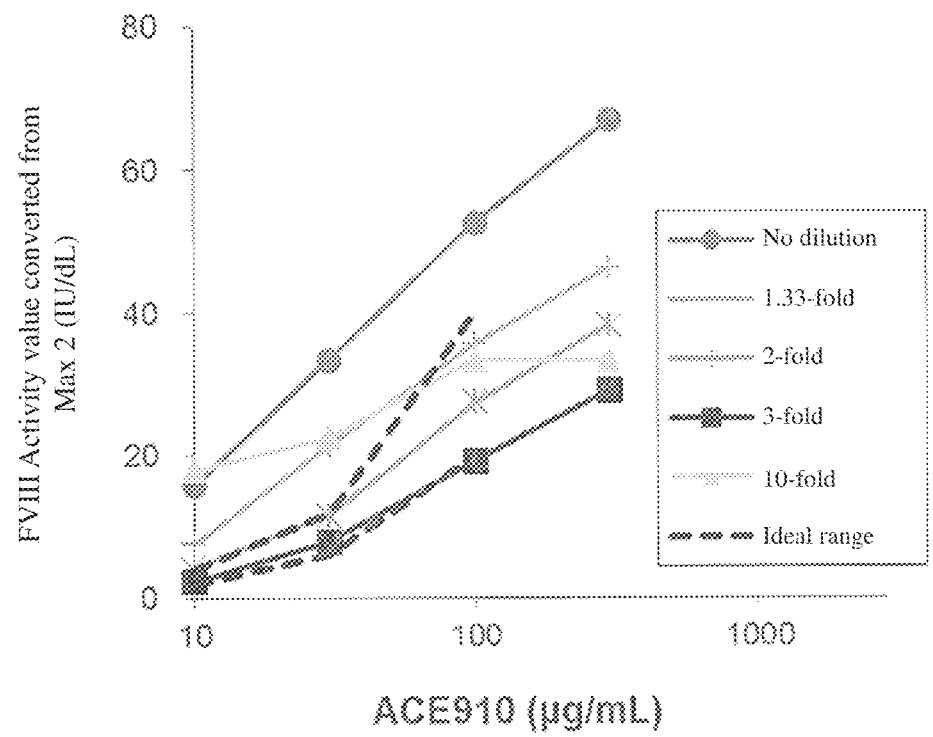
[Fig. 18A]
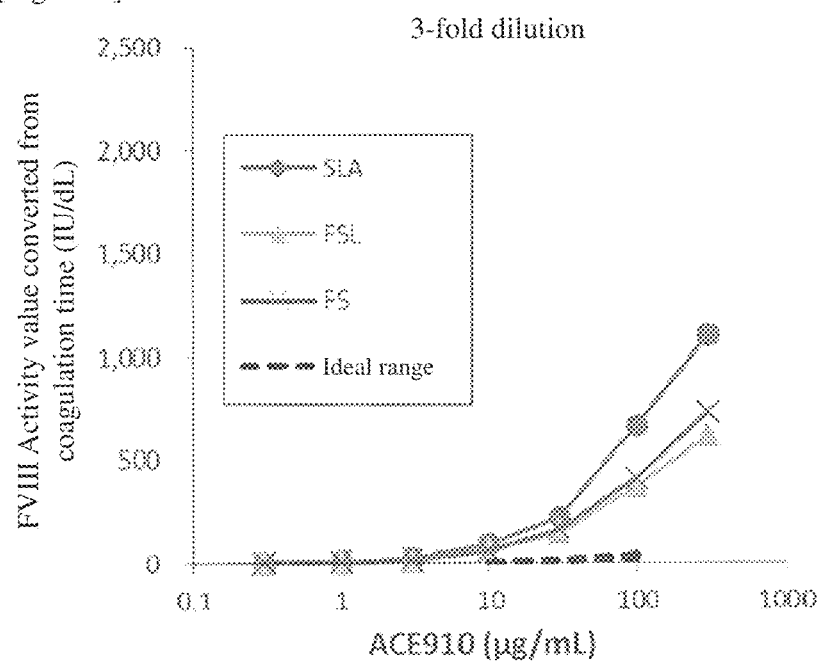

[Fig. 18B]
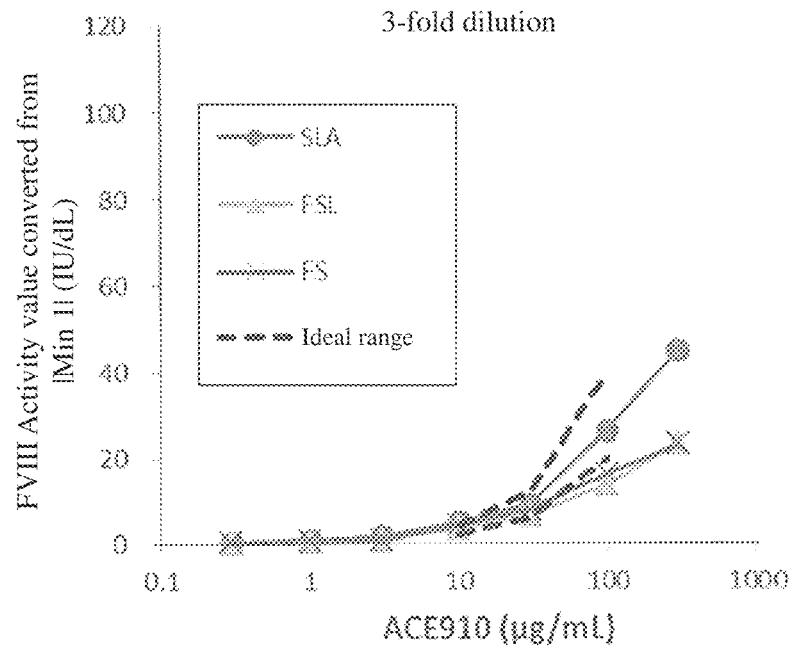
[Fig. 18C]
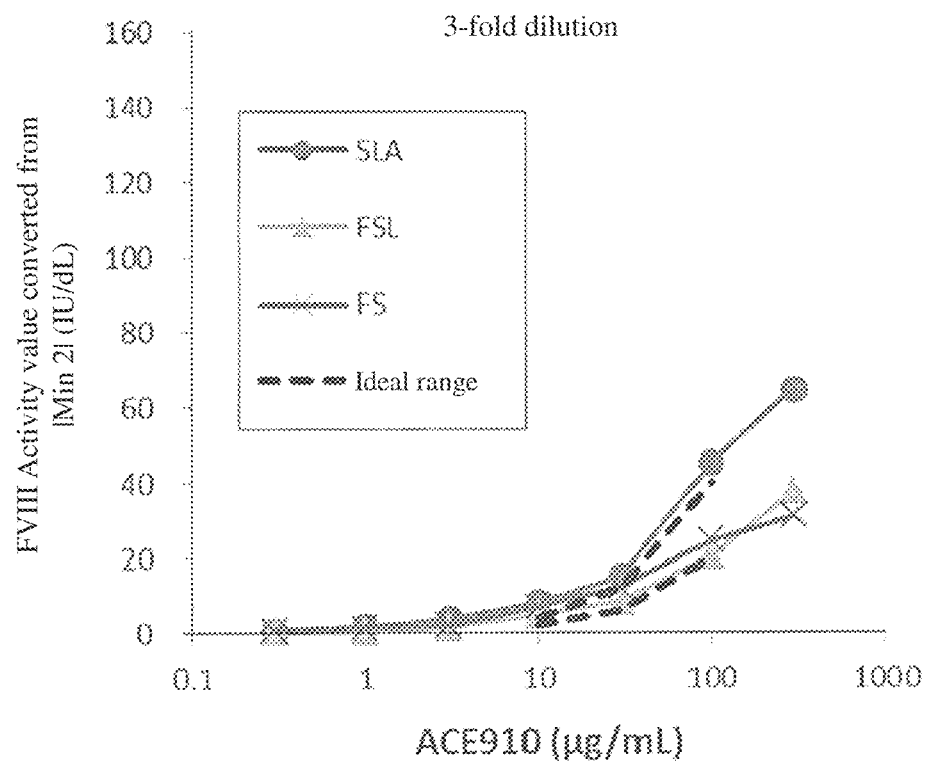

[Fig. 18D]
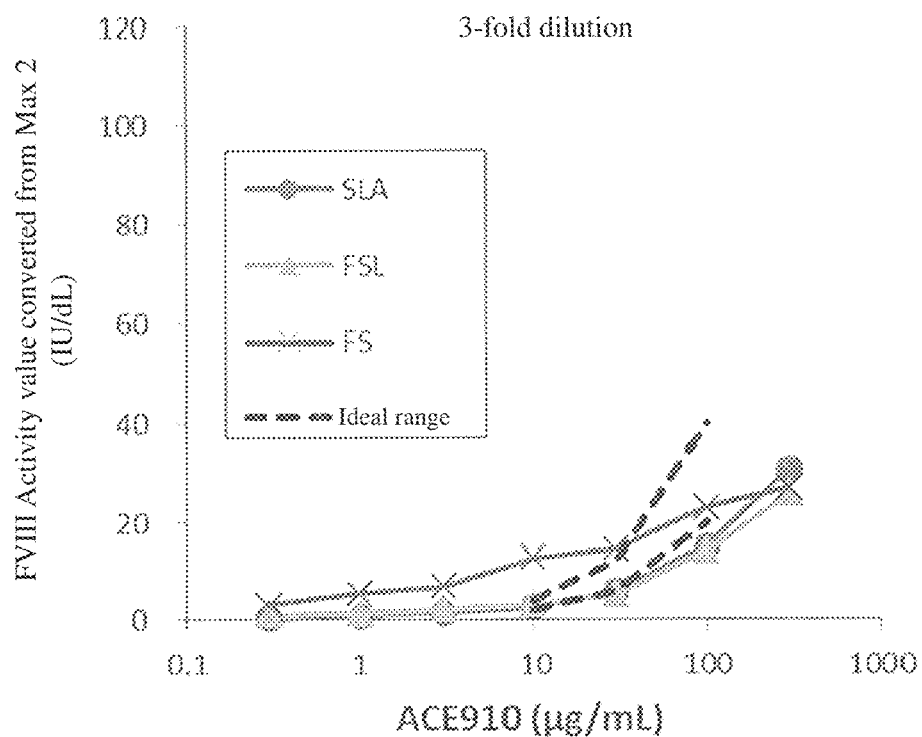
[Fig. 19A]
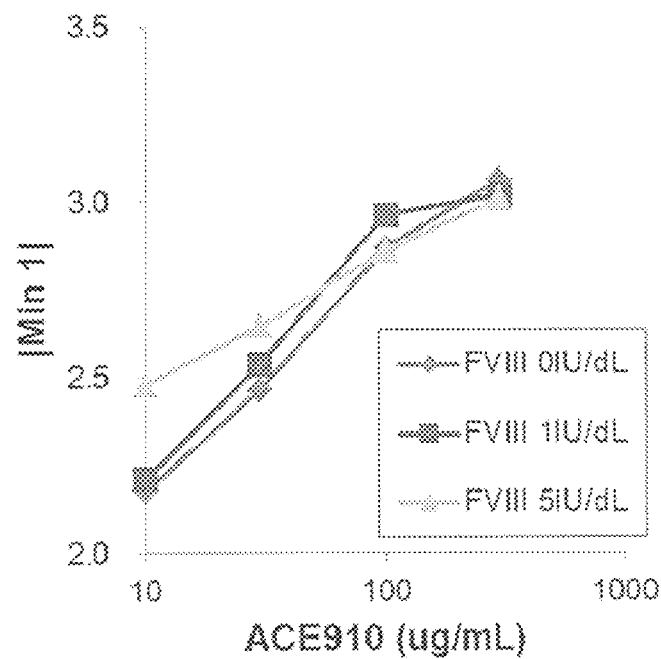

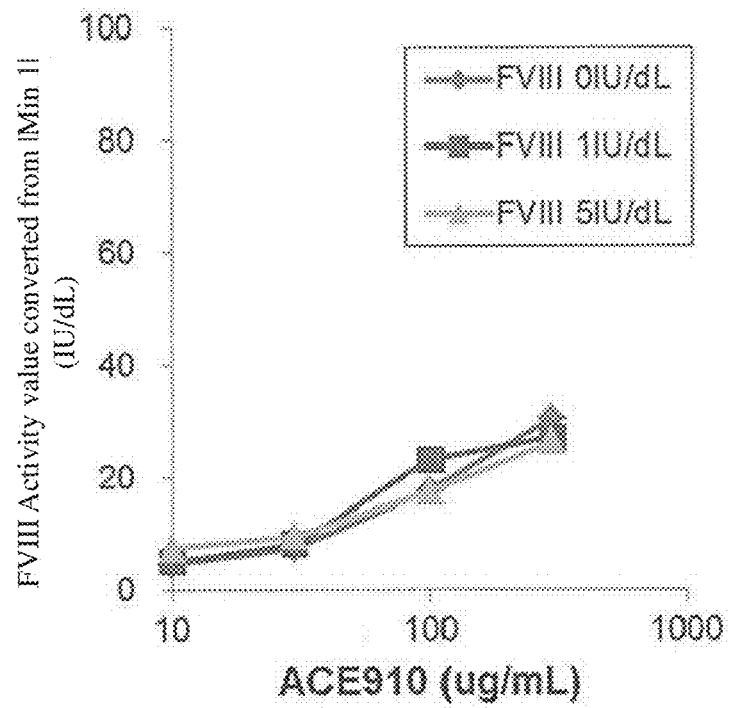
[Fig. 19B]
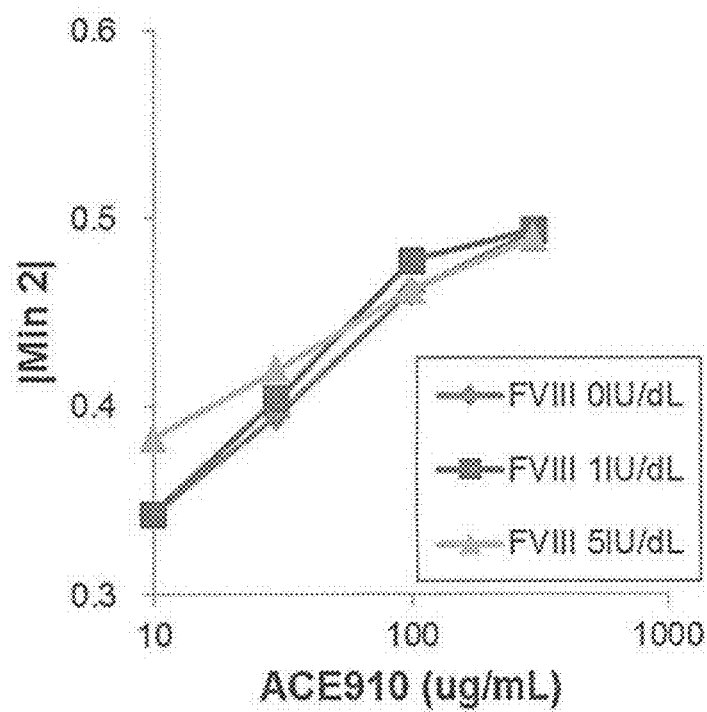
[Fig. 20A]

[Fig. 20B]
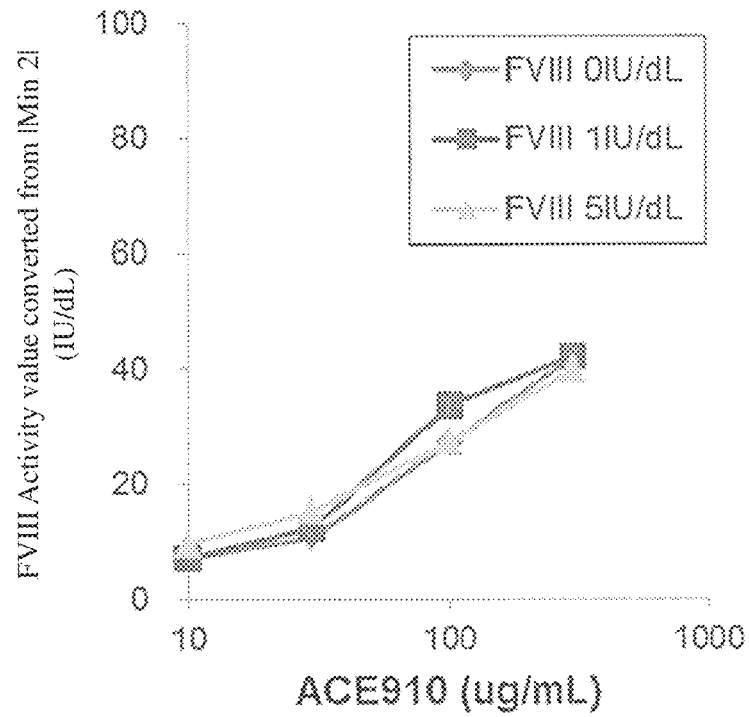
[Fig. 21A]
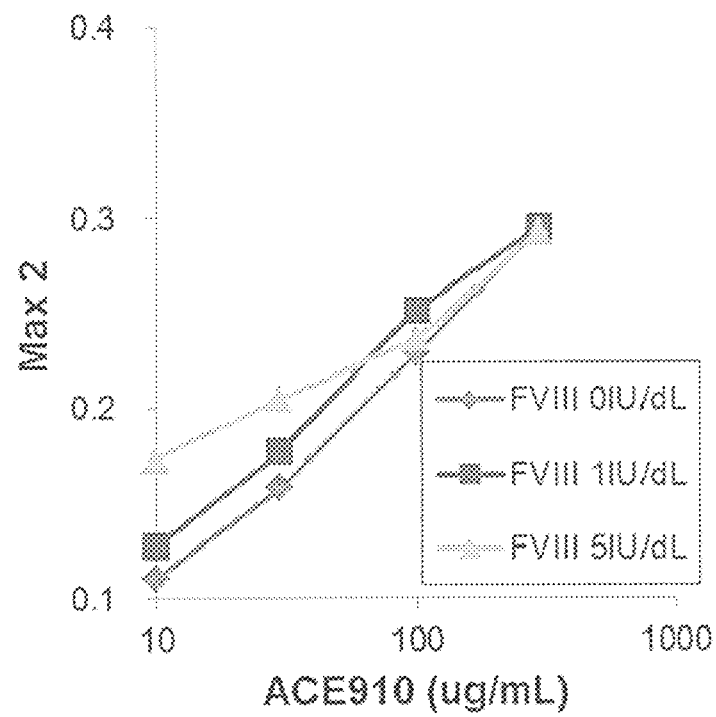

[Fig. 21B]
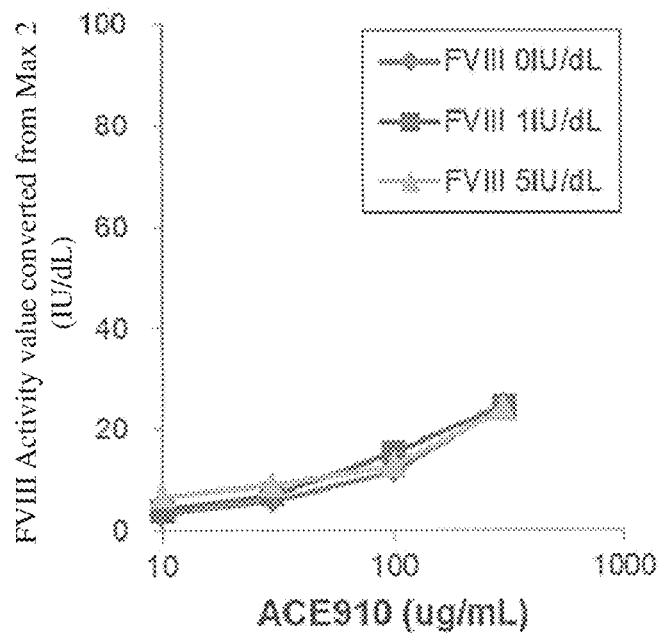
[Fig. 22A]
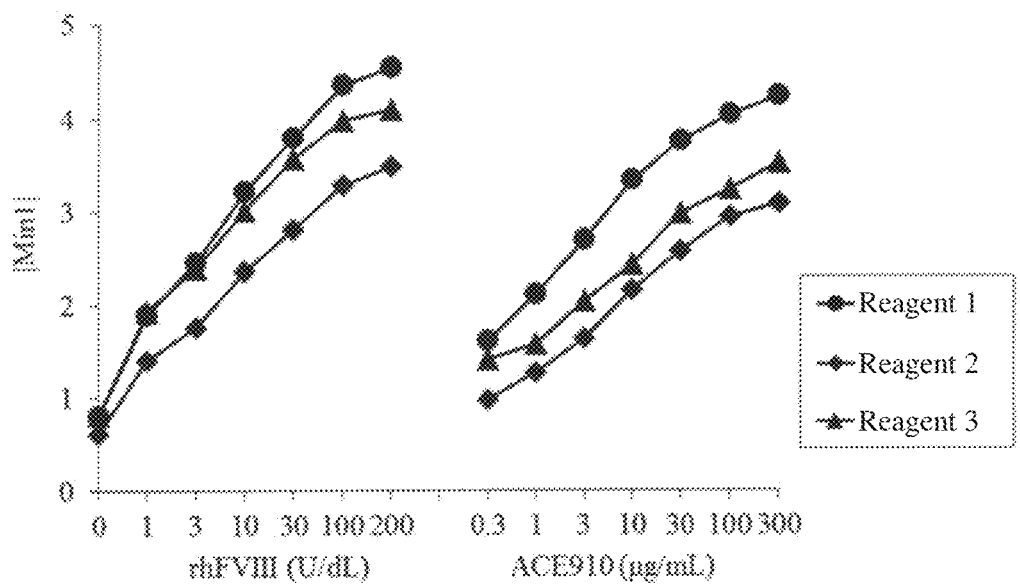

[Fig. 22B]
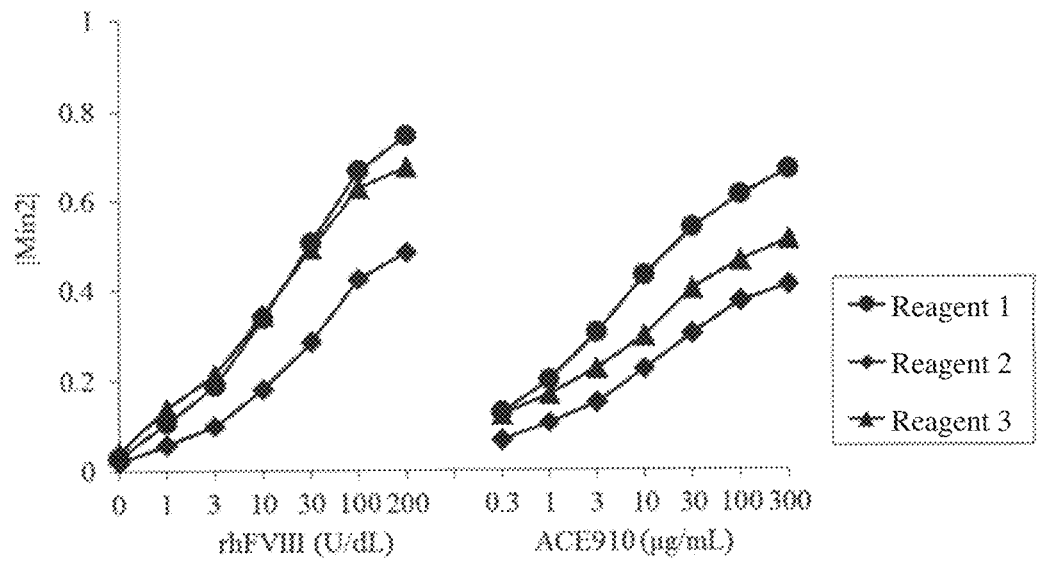
[Fig. 22C]
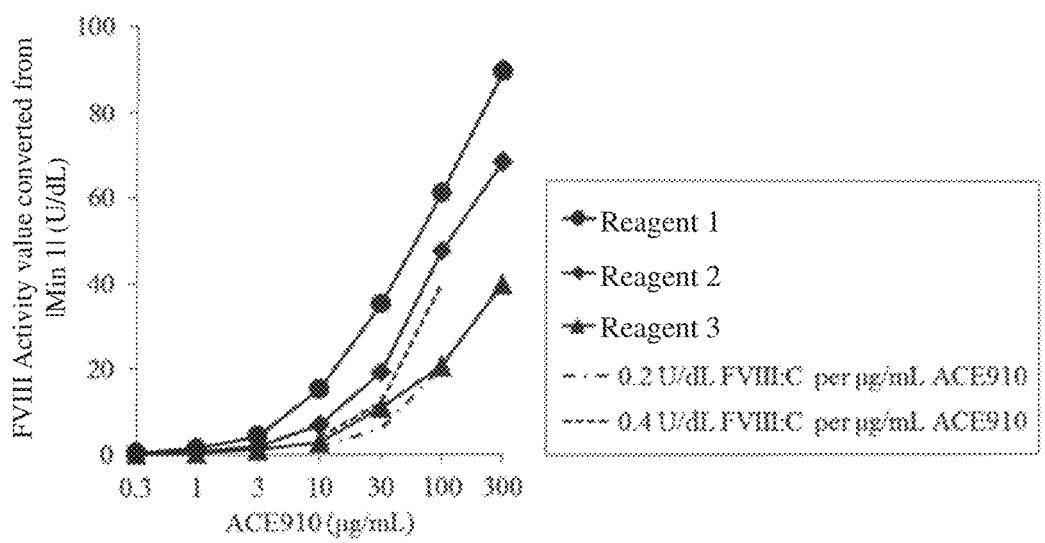

[Fig. 22D]
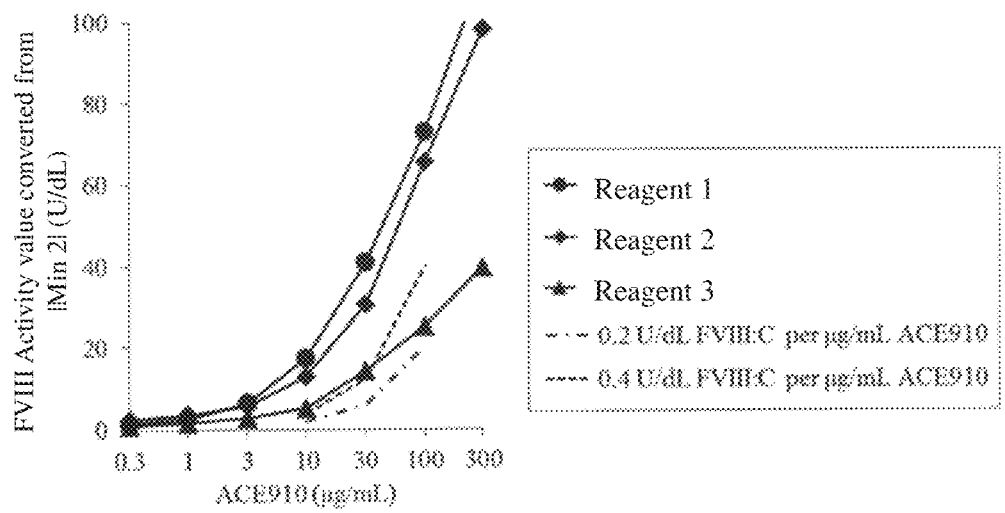
[Fig. 23A]
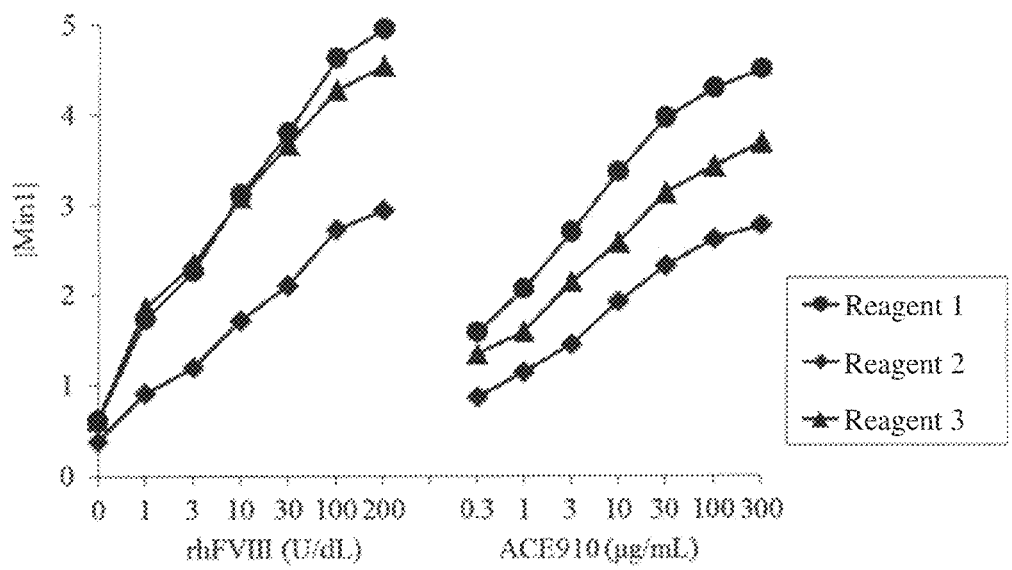

[Fig. 23B]
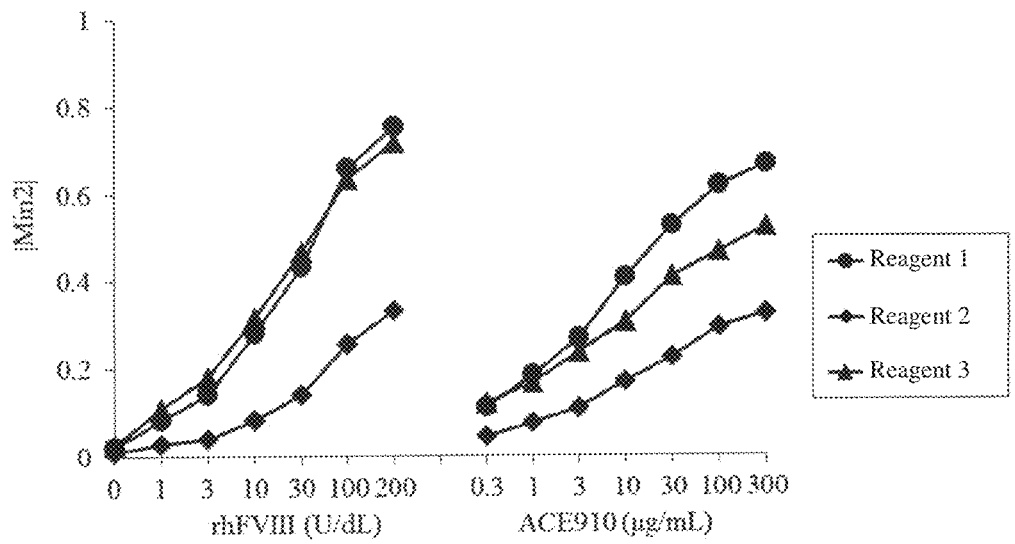
[Fig. 23C]
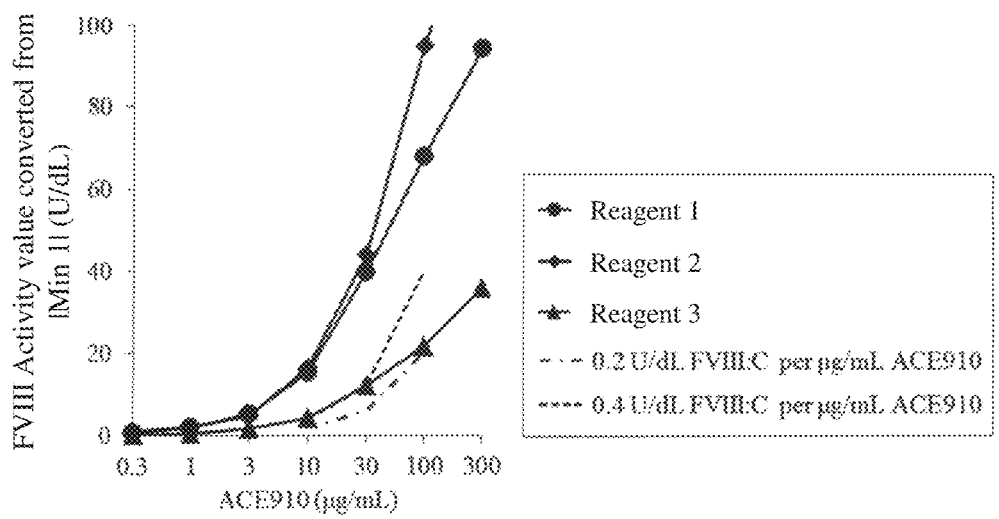

[Fig. 23D]
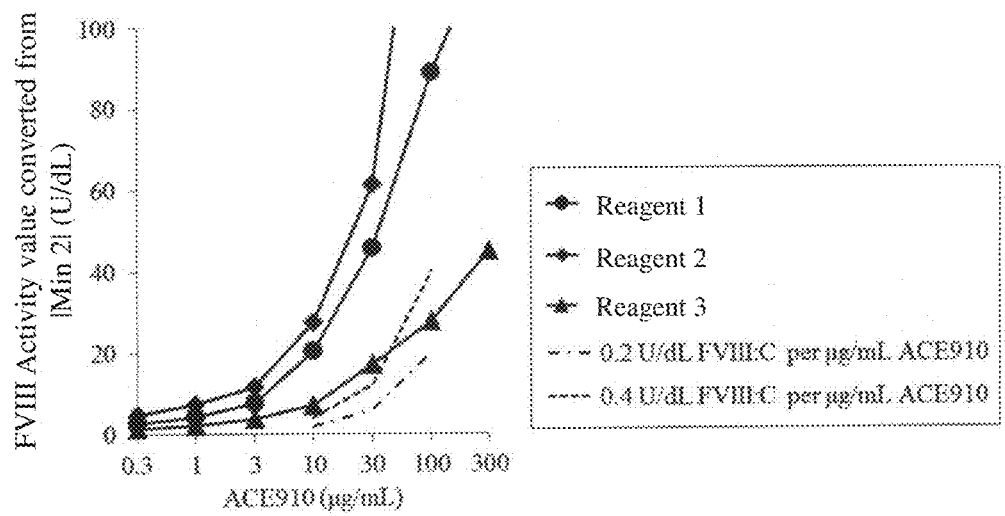
[Fig. 24A]
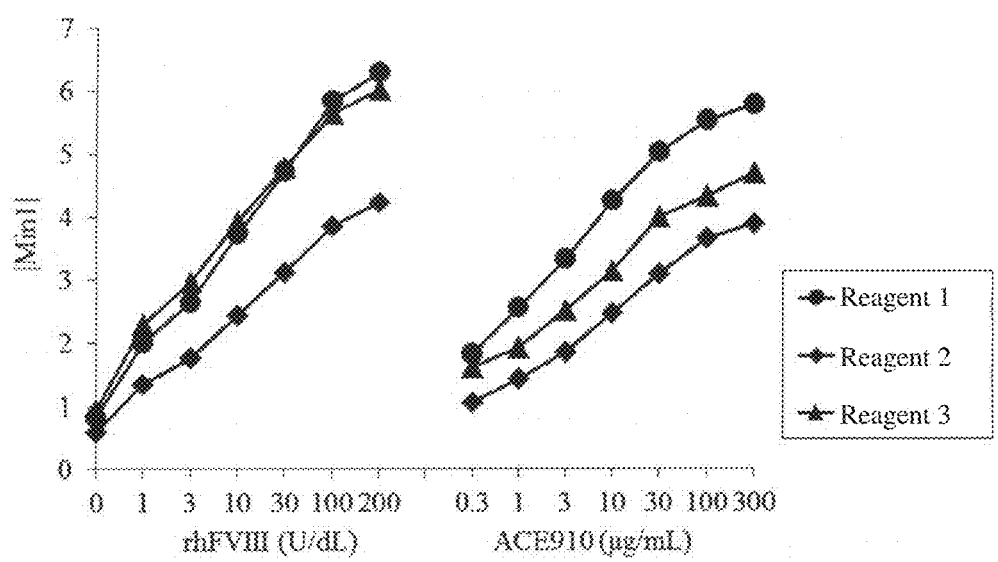

[Fig. 24B]
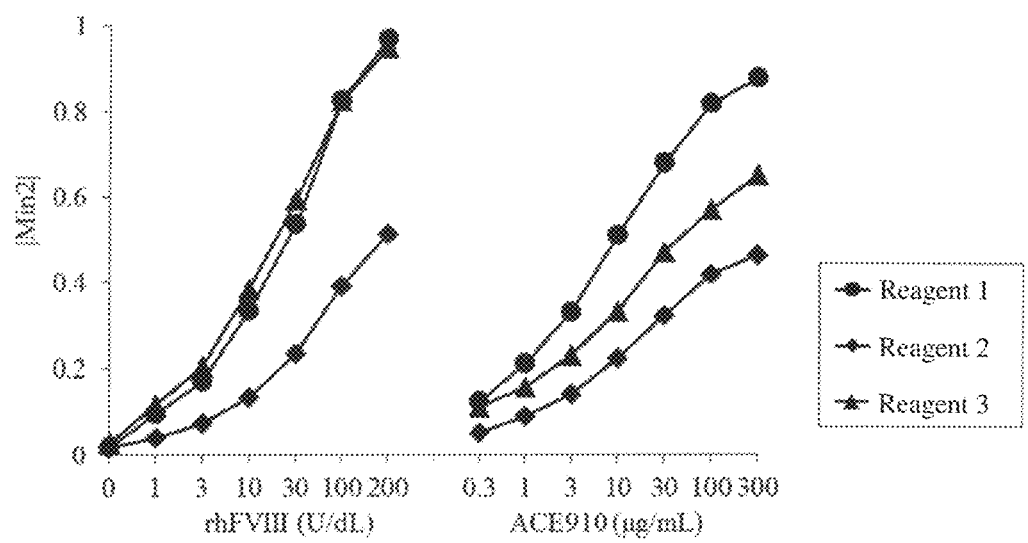
[Fig. 24C]
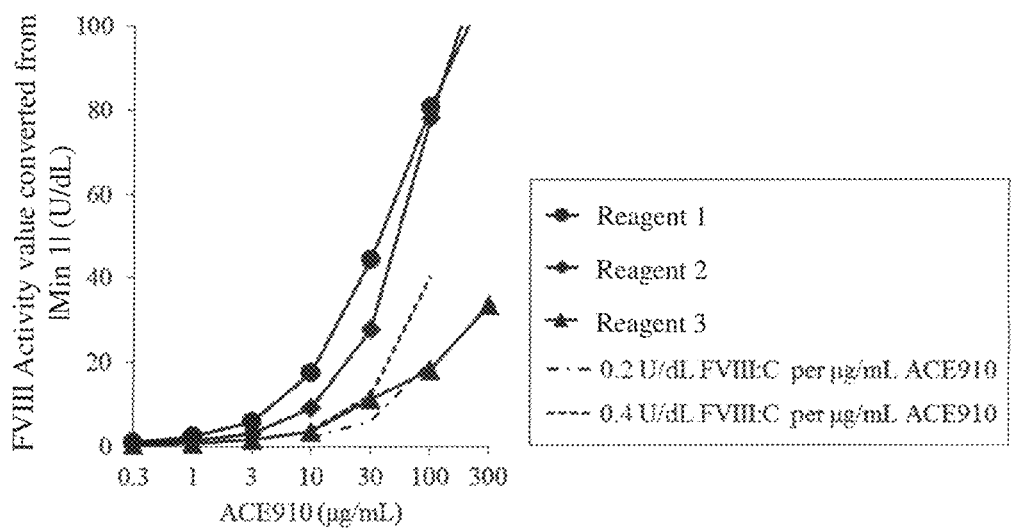

[Fig. 24D]
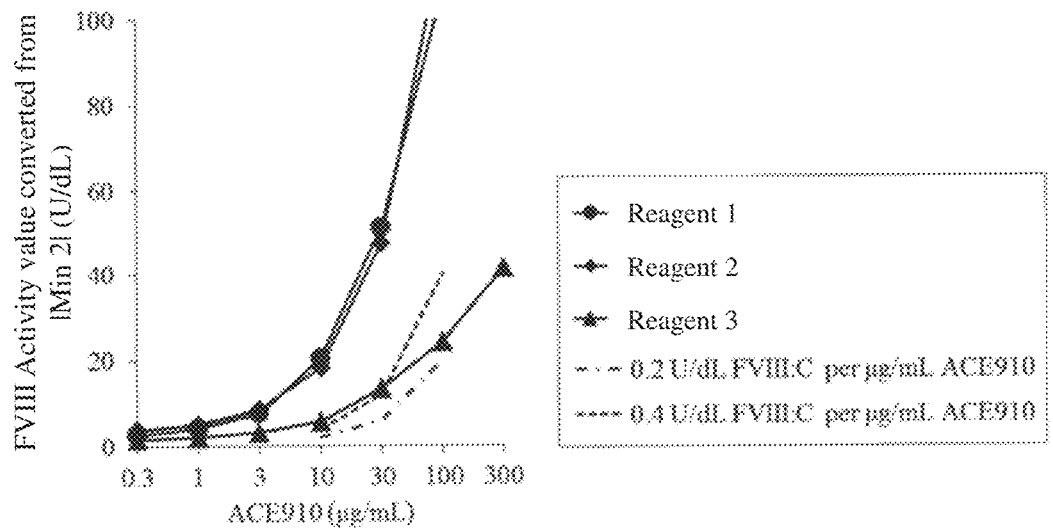
[Fig. 25A]
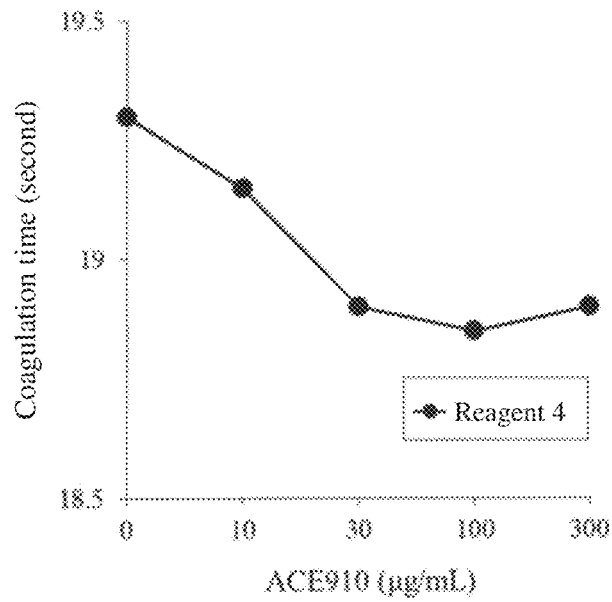

[Fig. 25B]
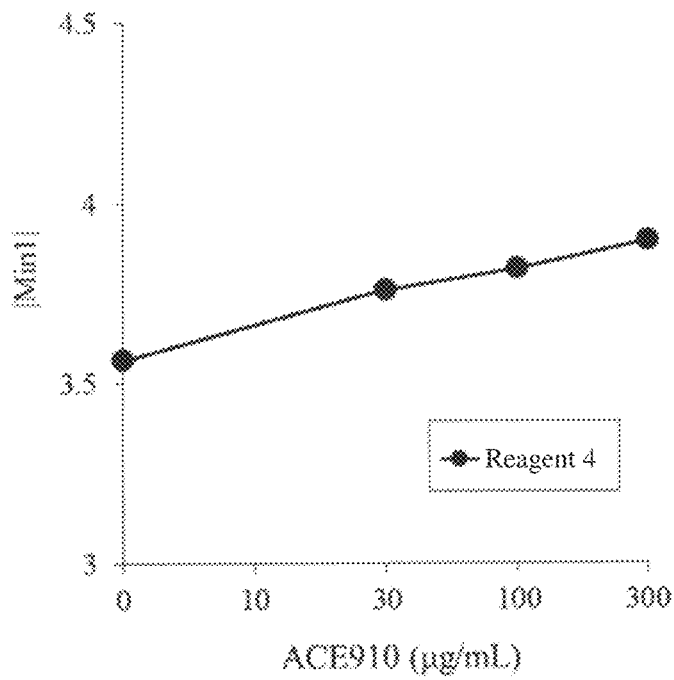
[Fig. 25C]
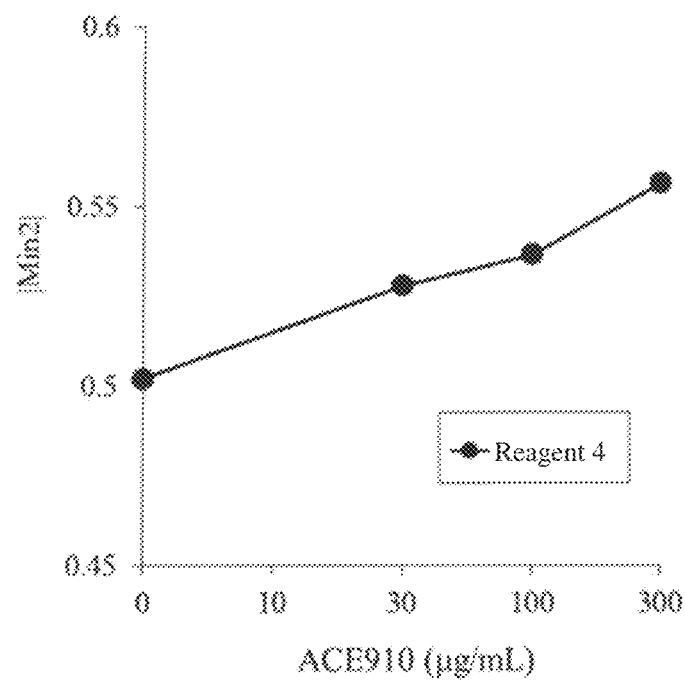

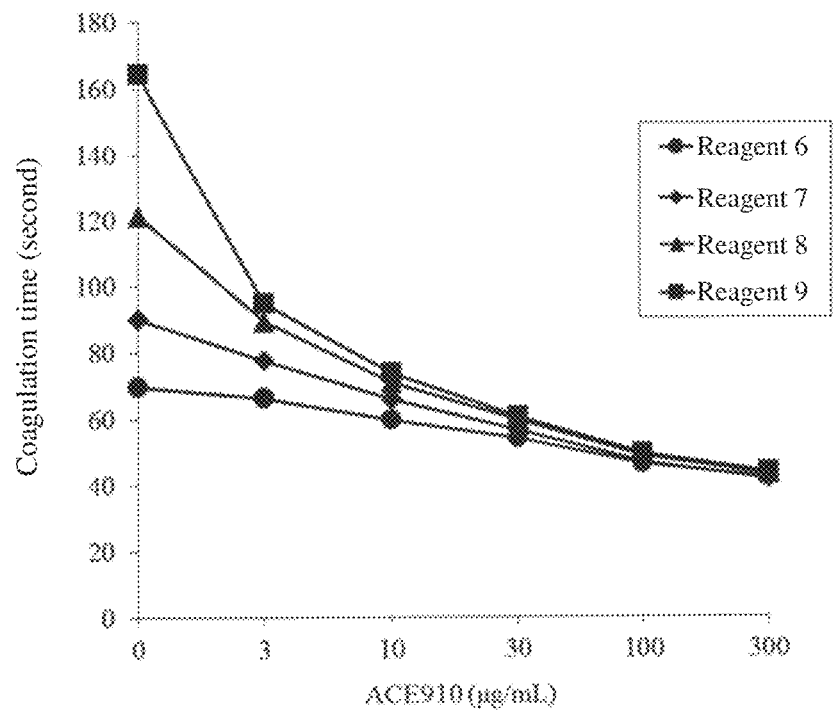
[Fig. 26A]
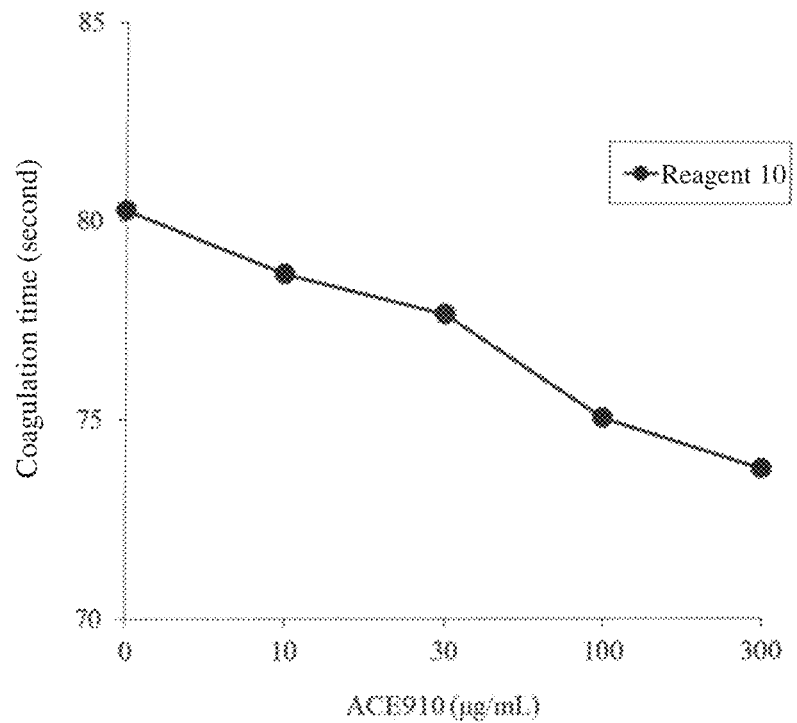
[Fig. 26B]

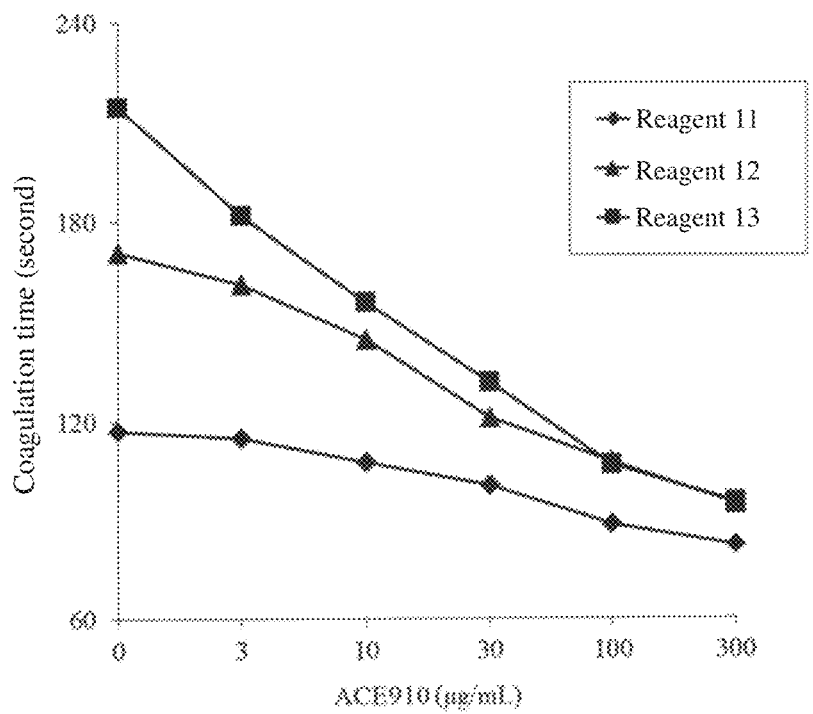
[Fig. 26C]
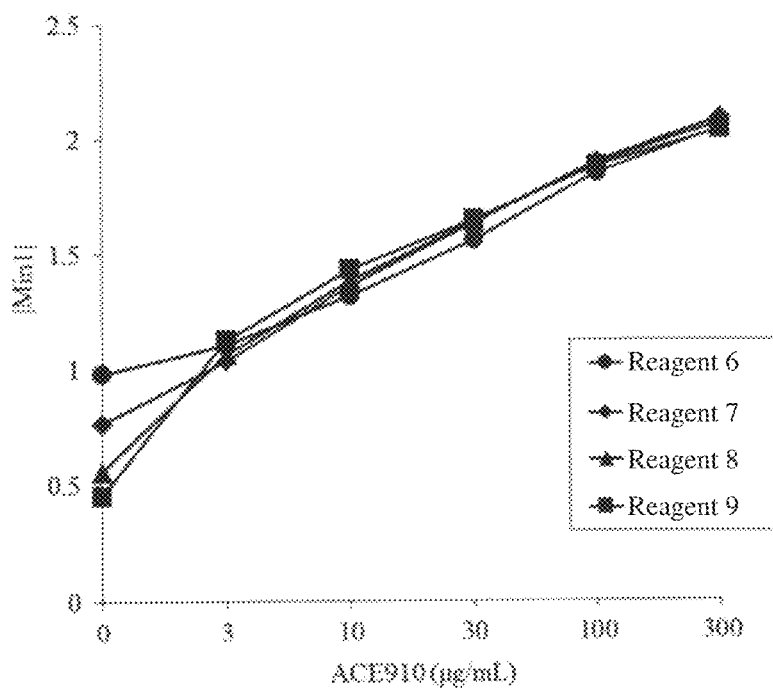
[Fig. 26D]

[Fig. 26E]
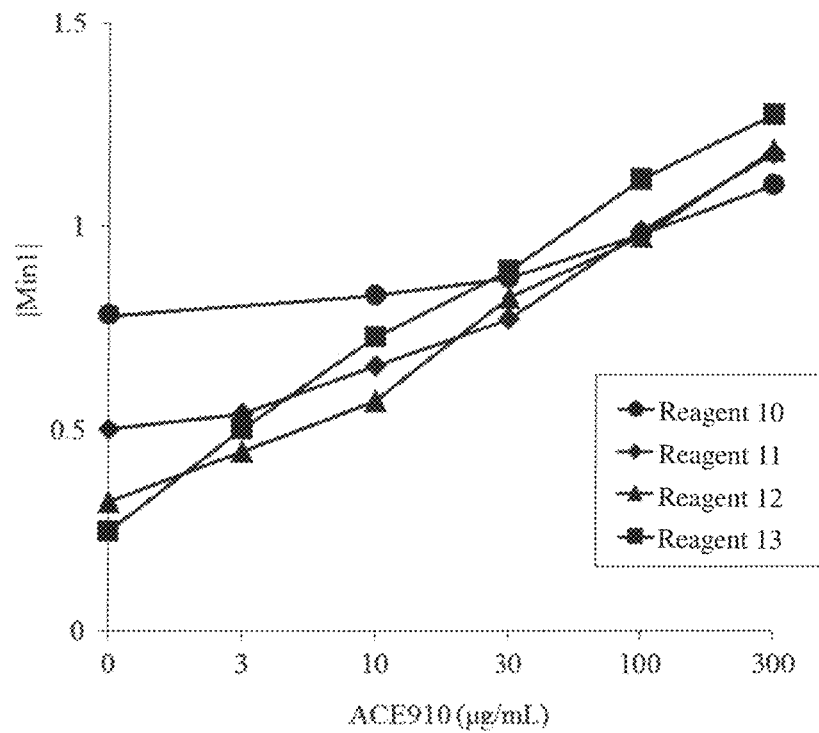
[Fig. 26F]
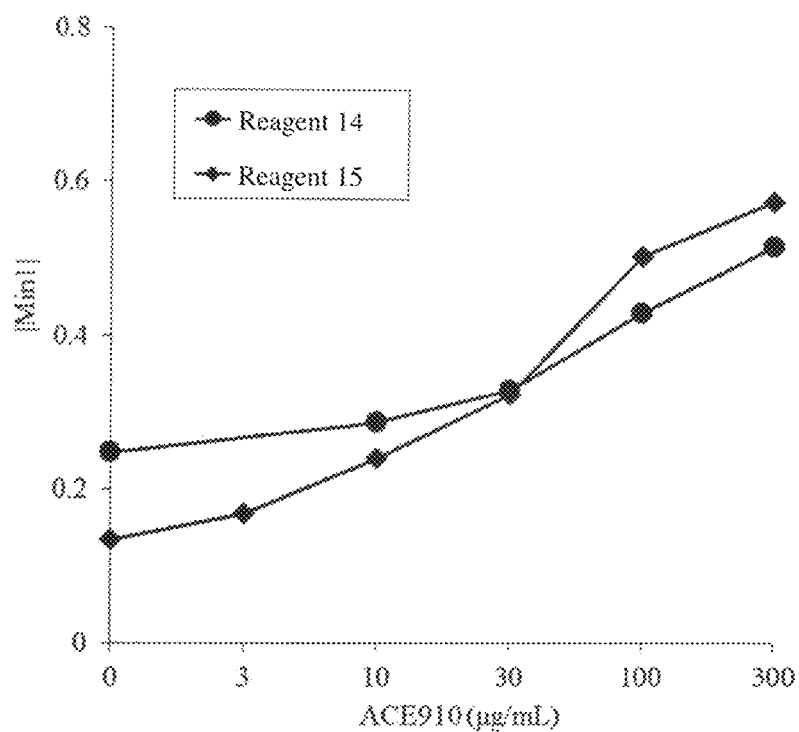

[Fig. 26G]
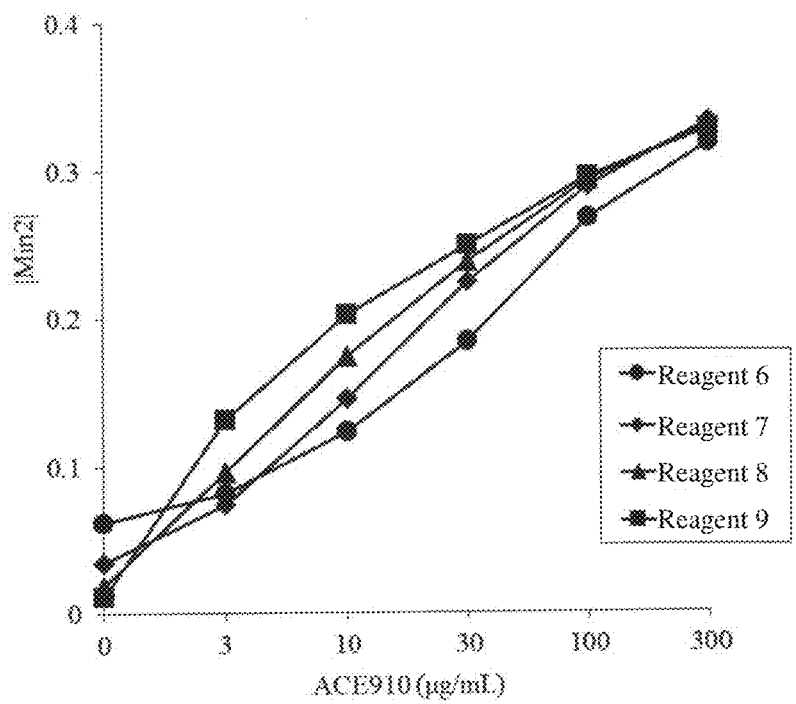
[Fig. 26H]
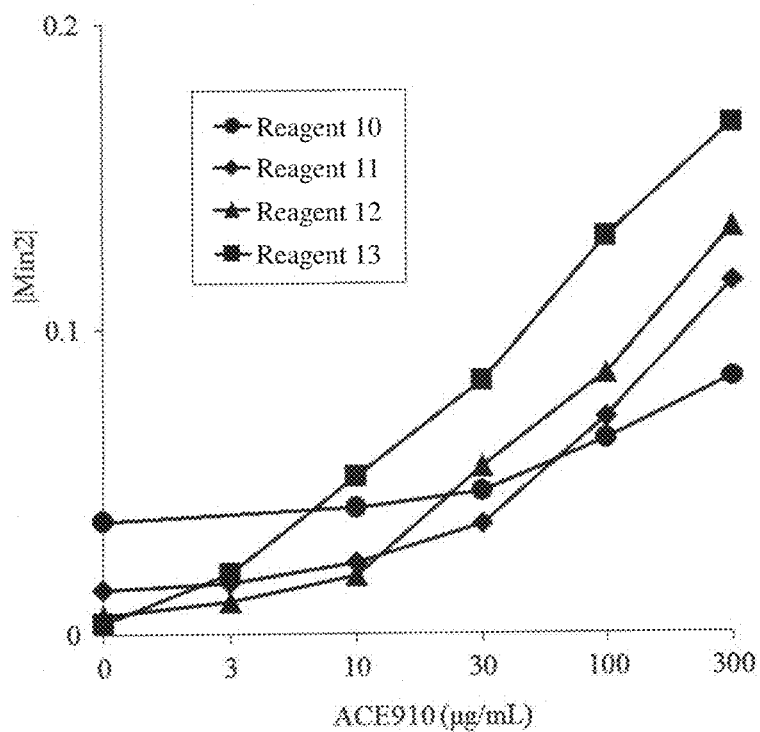

[Fig. 26I]
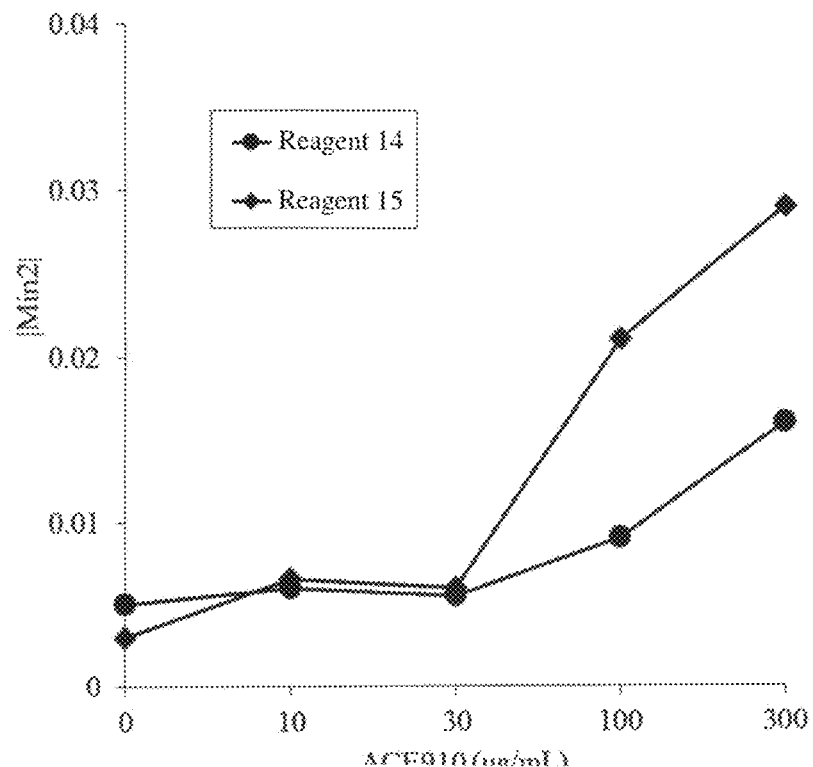
[Fig. 27A]
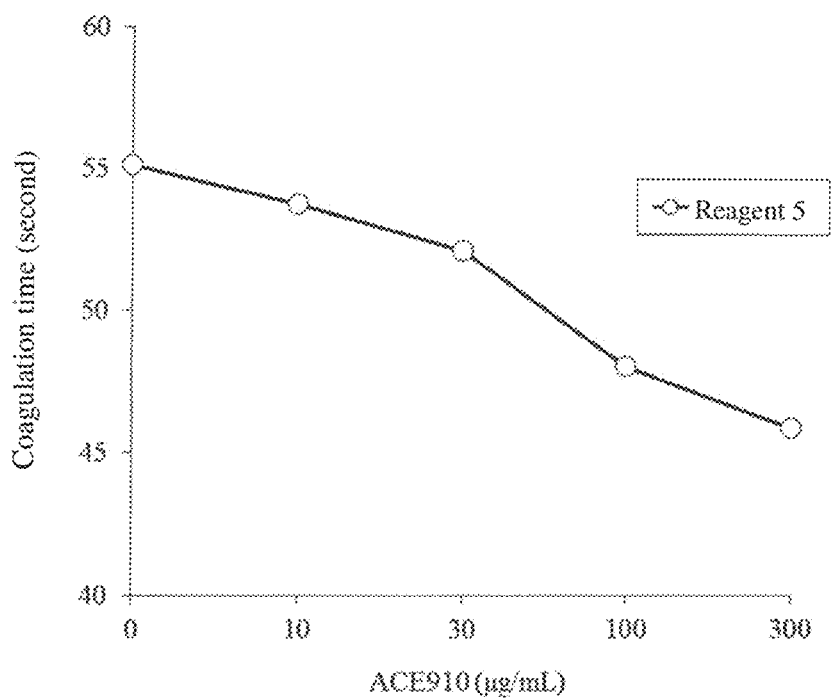

[Fig. 27B]
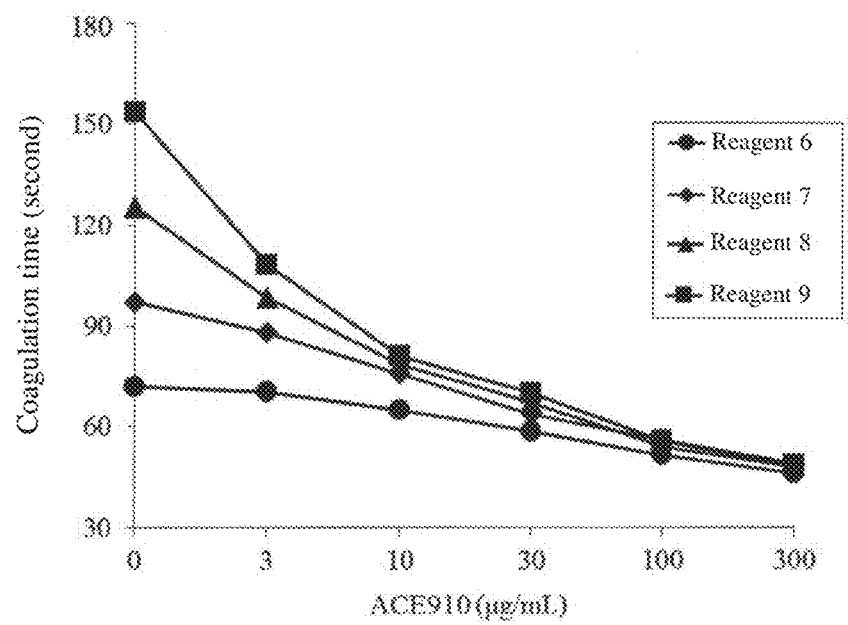
[Fig. 27C]
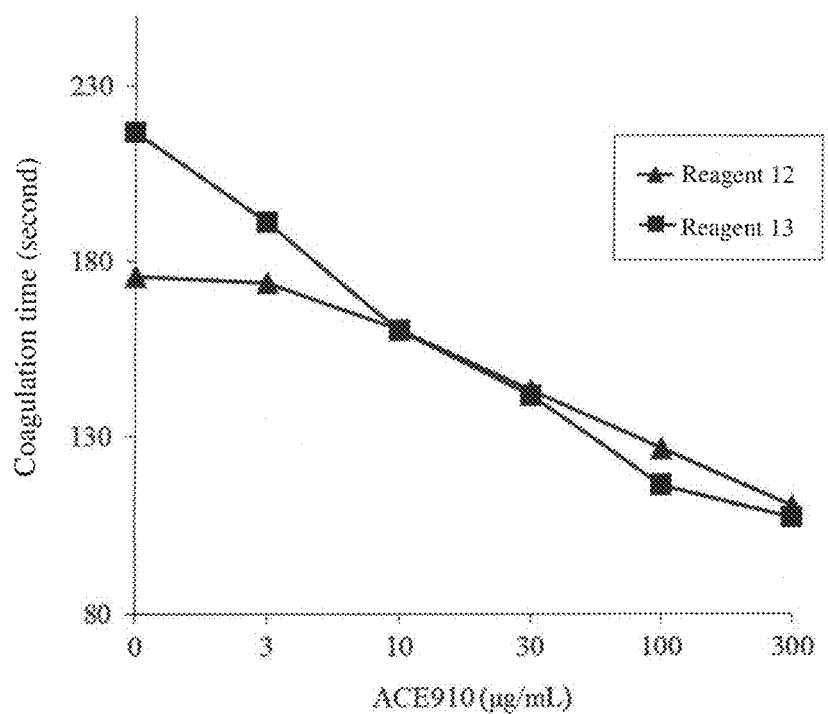

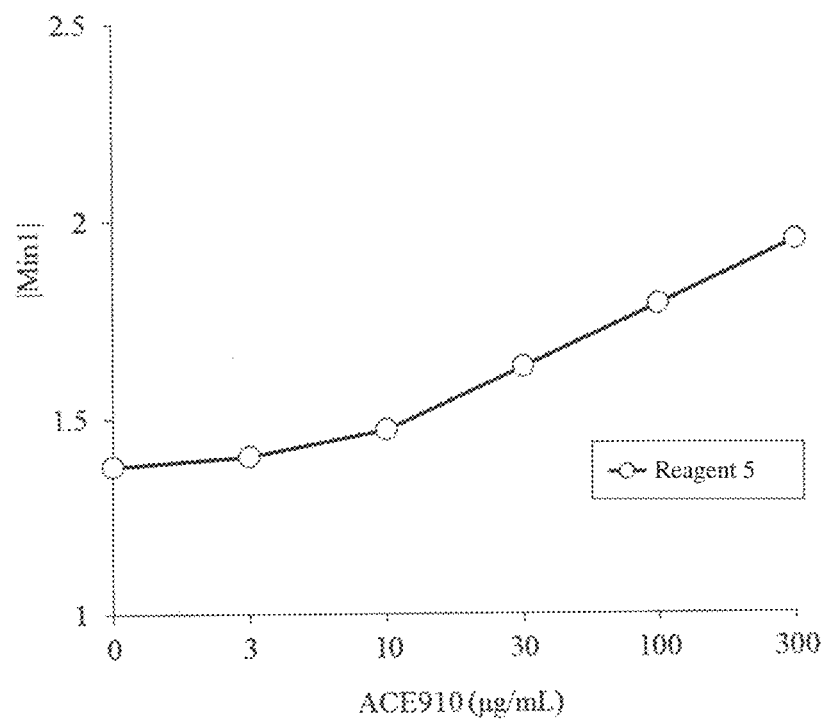
[Fig. 27D]
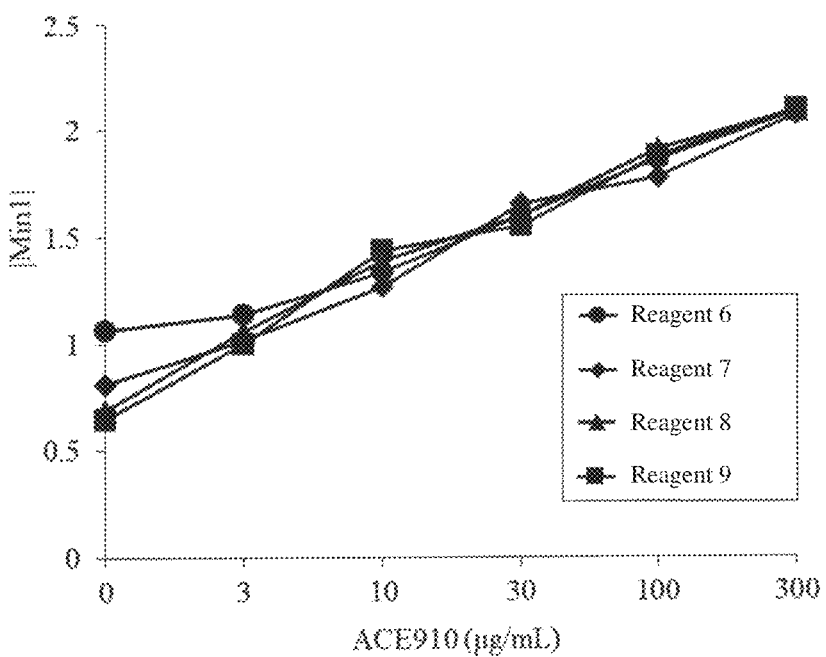
[Fig. 27E]

[Fig. 27F]
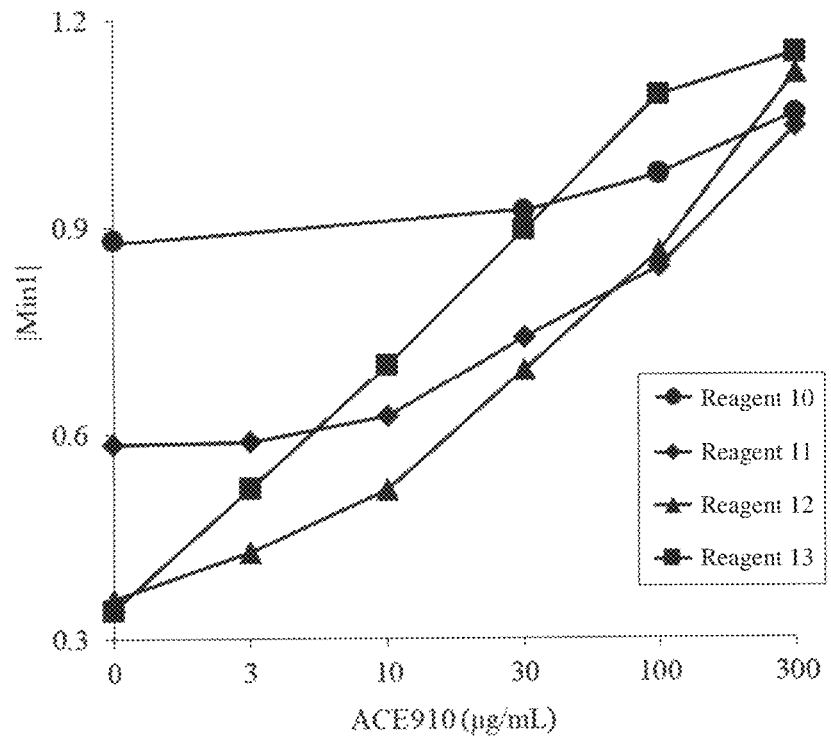
[Fig. 27G]
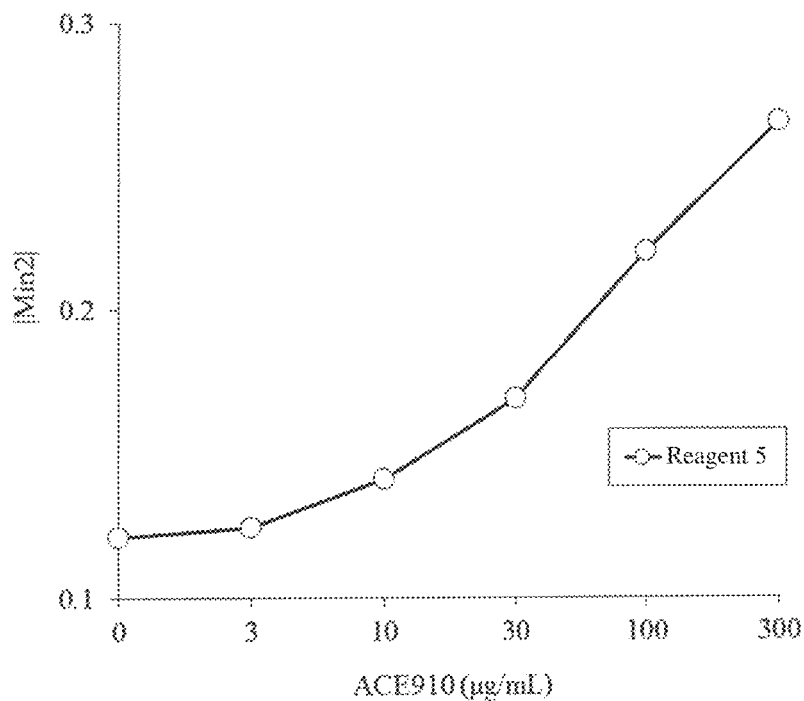

[Fig. 27H]
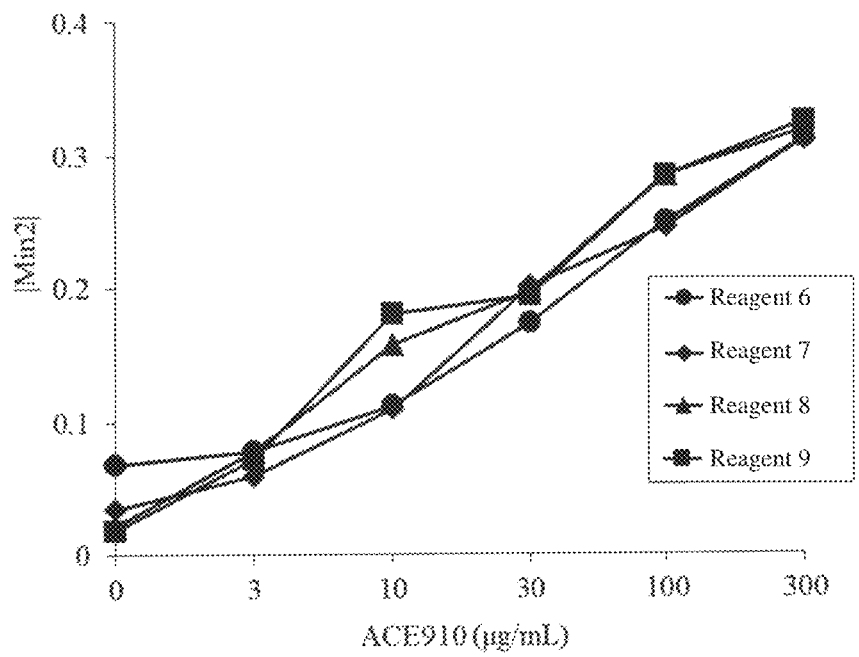
[Fig. 27I]
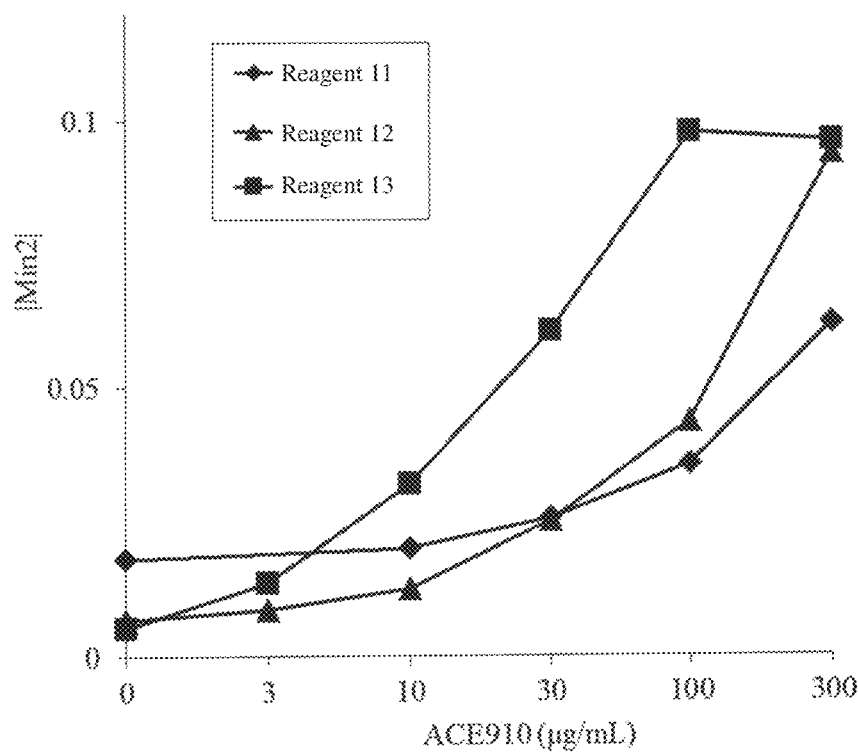

[Fig. 28]
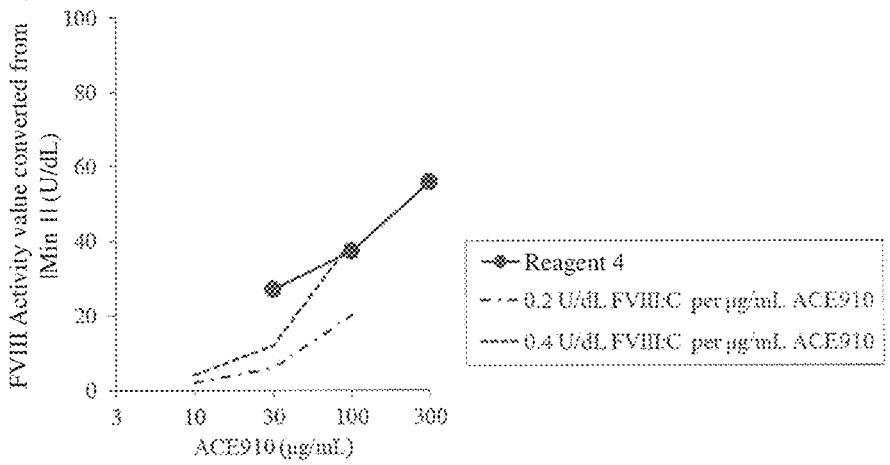
[Fig. 29]
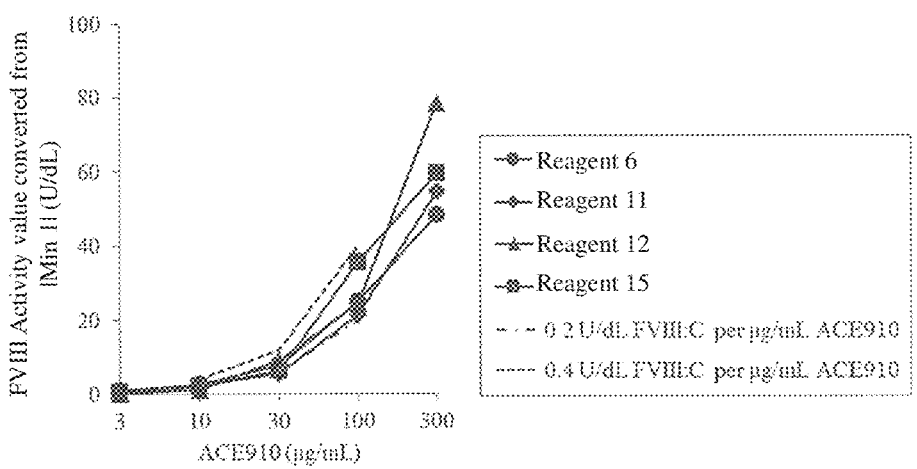
[Fig. 30A]
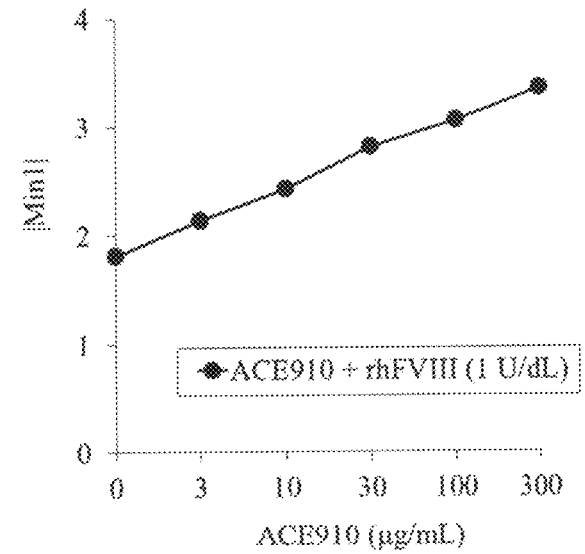

[Fig. 30B]
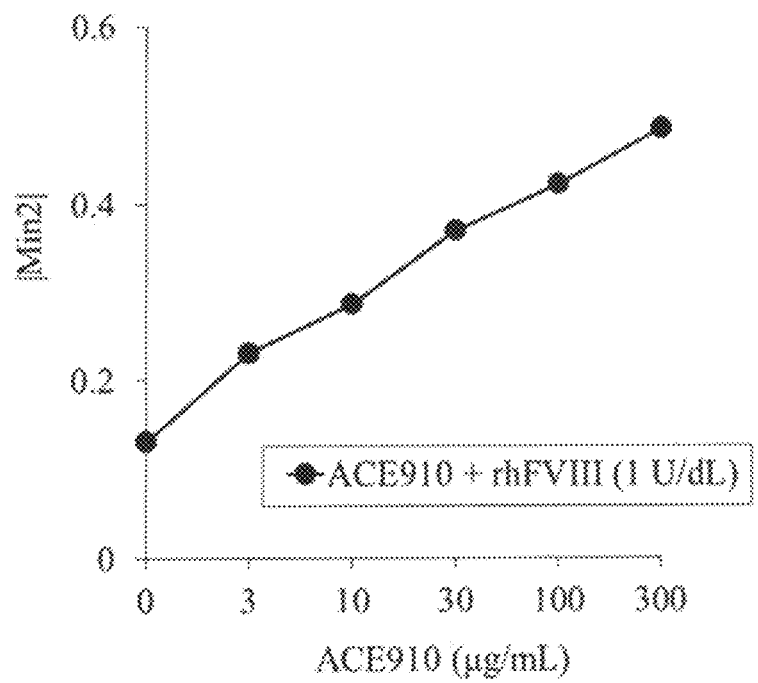
[Fig. 30C]
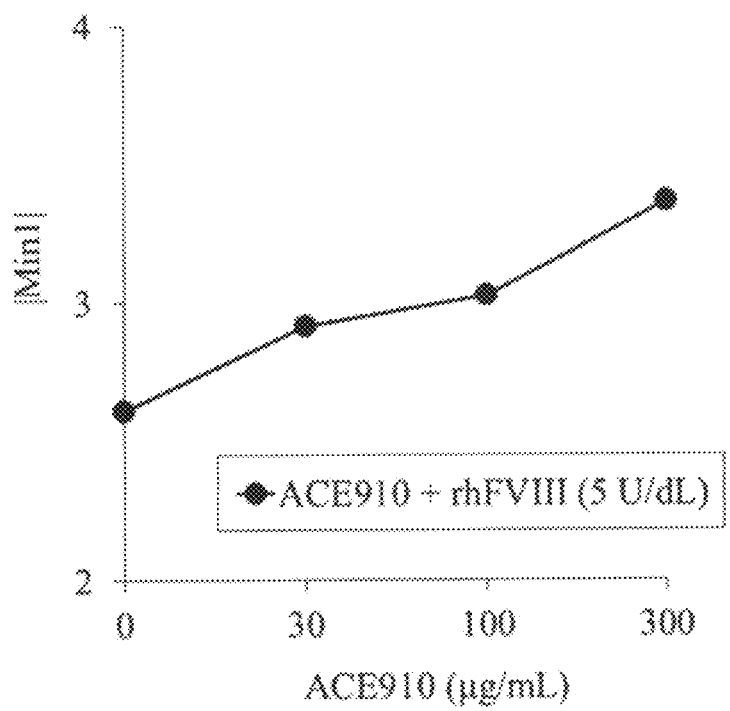

[Fig. 30D]
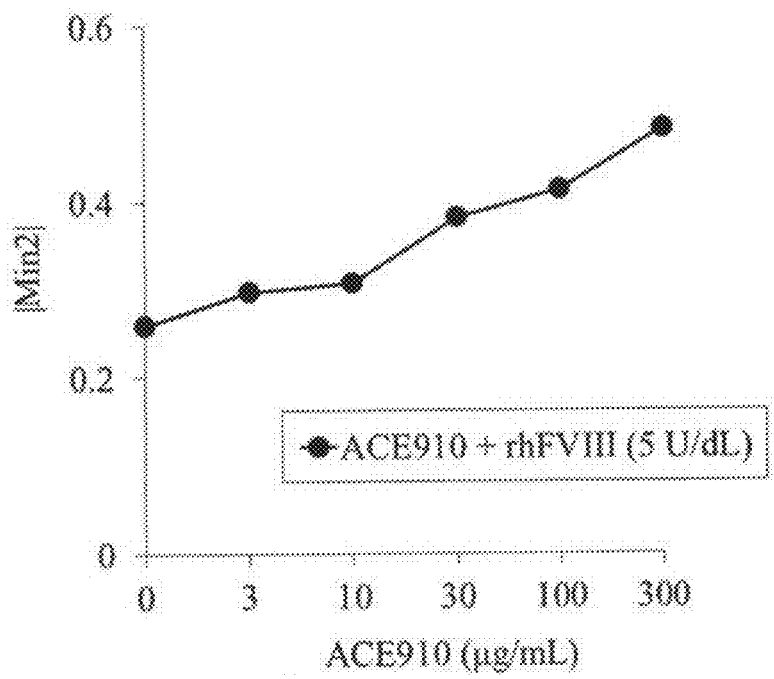
[Fig. 30E]
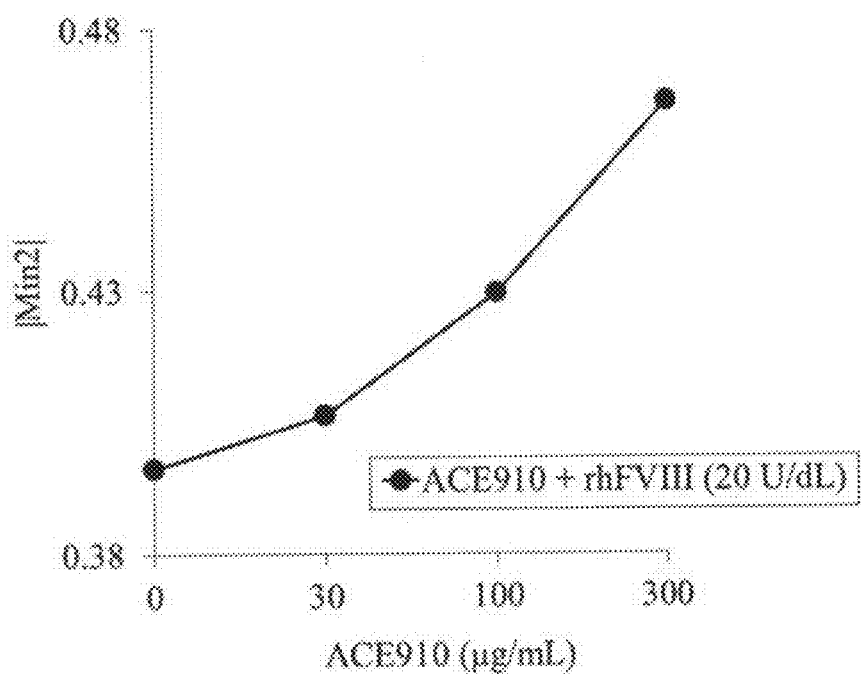

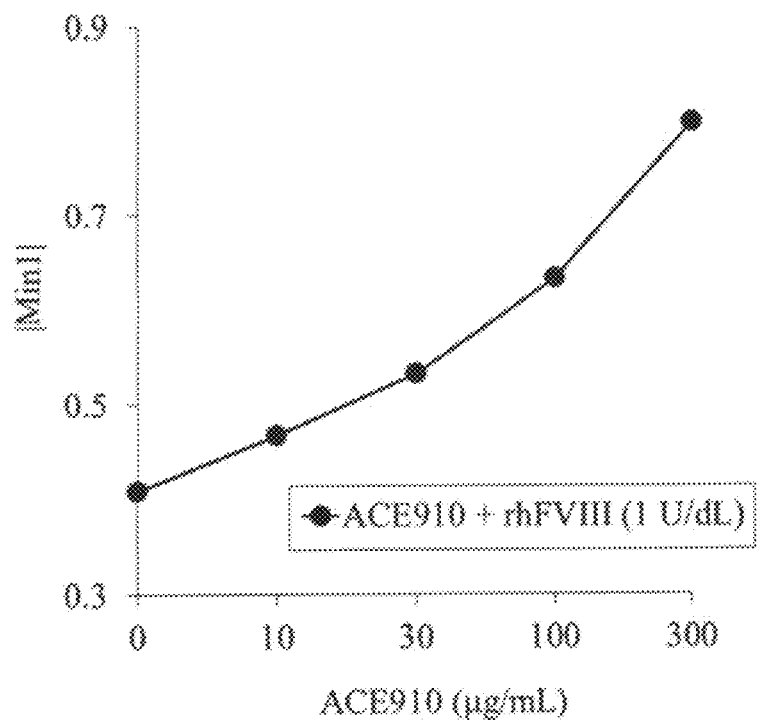
[Fig. 31A]
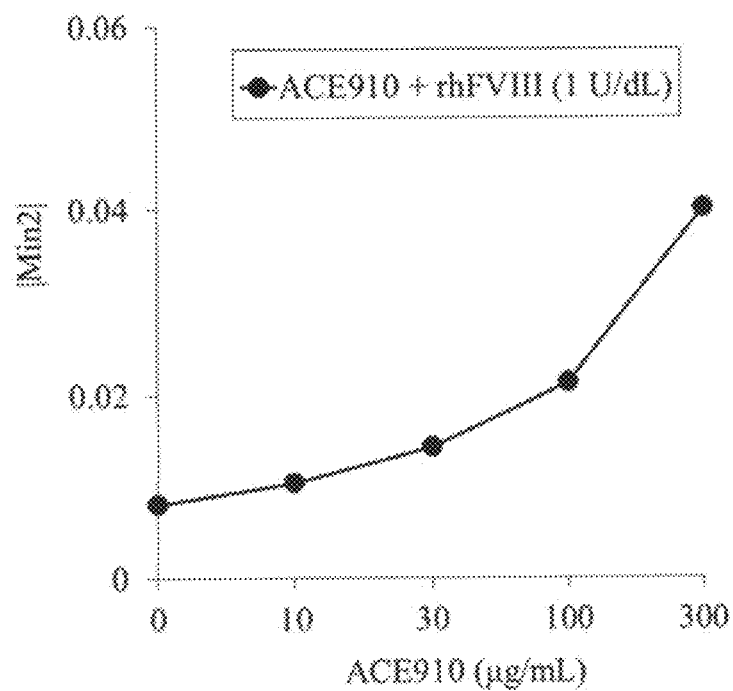
[Fig. 31B]

[Fig. 31C]
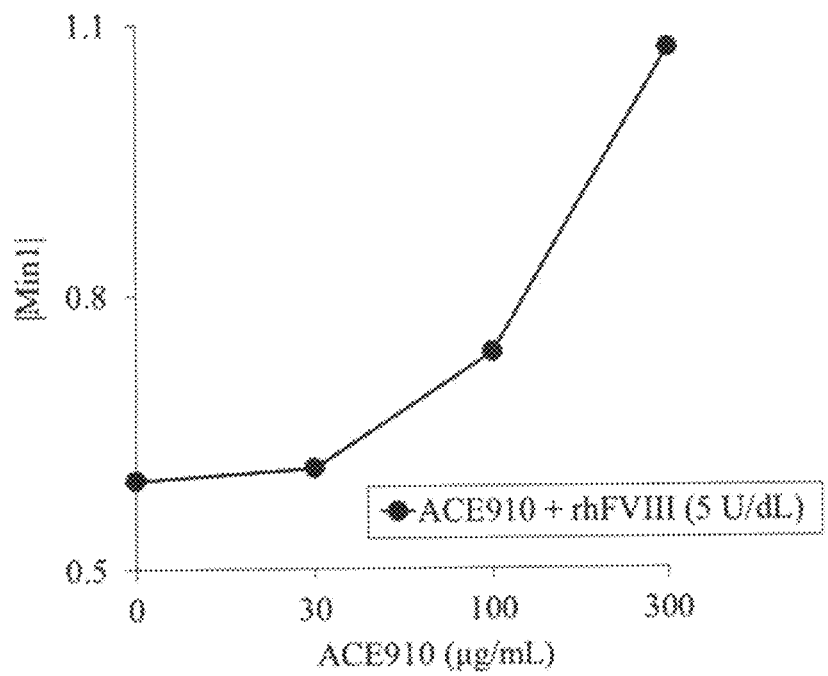
[Fig. 31D]
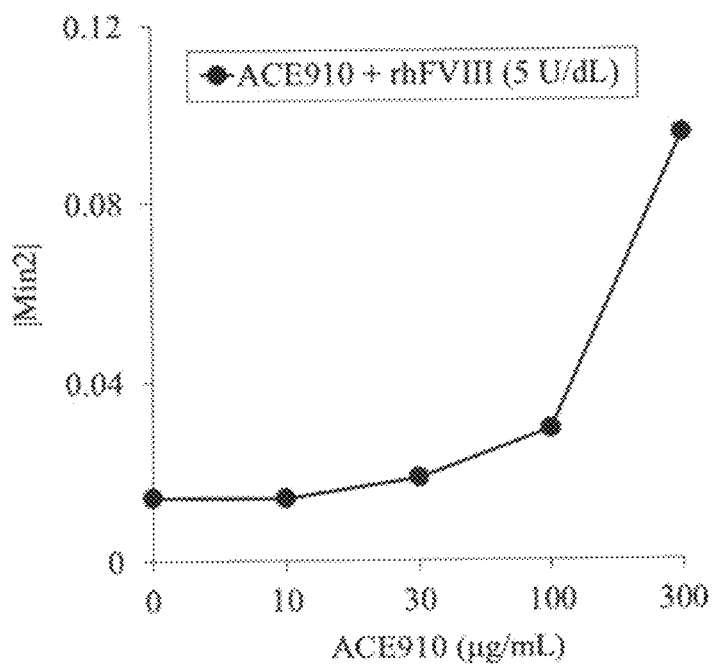

[Fig. 31E]
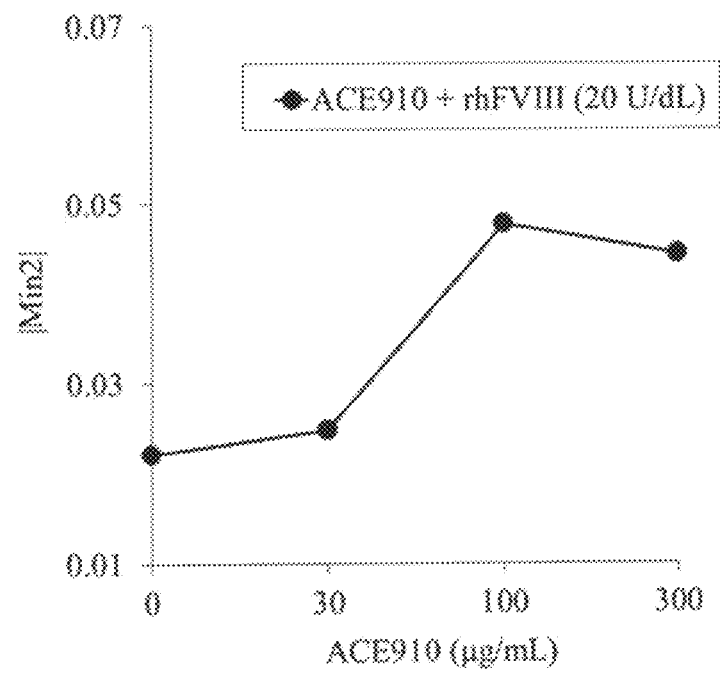
[Fig. 31F]
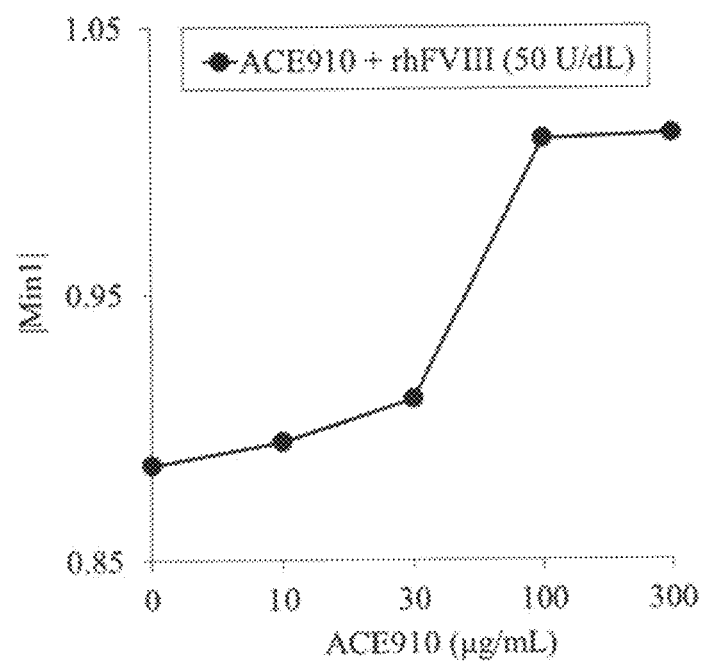

[Fig. 31G]
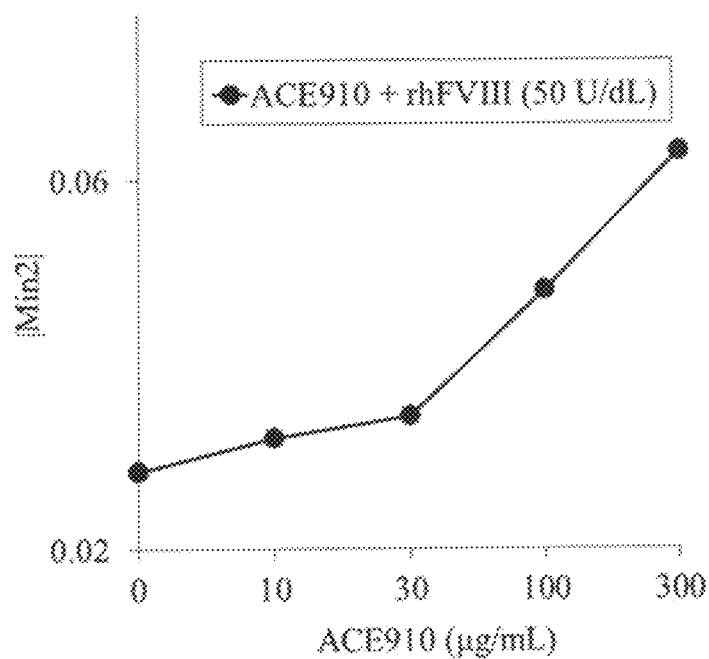
[Fig. 31H]
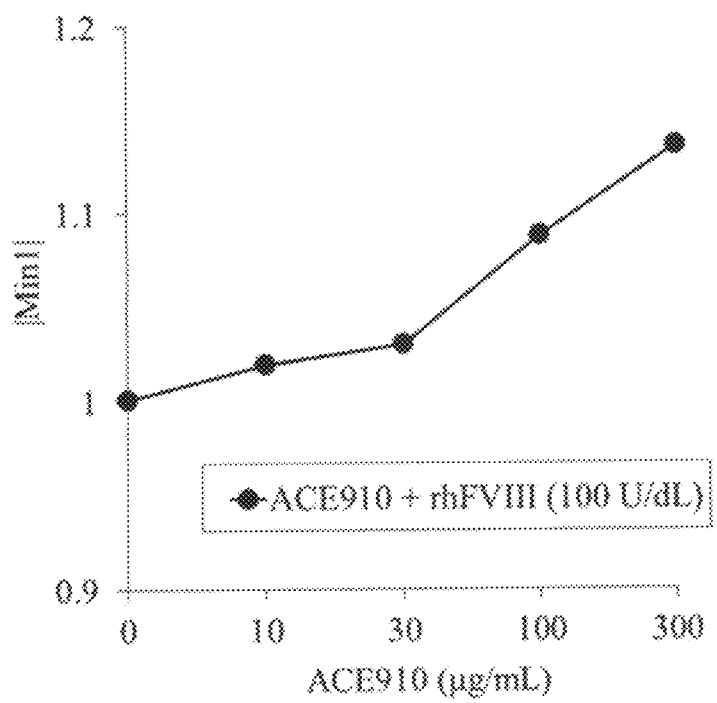

[Fig. 31I]
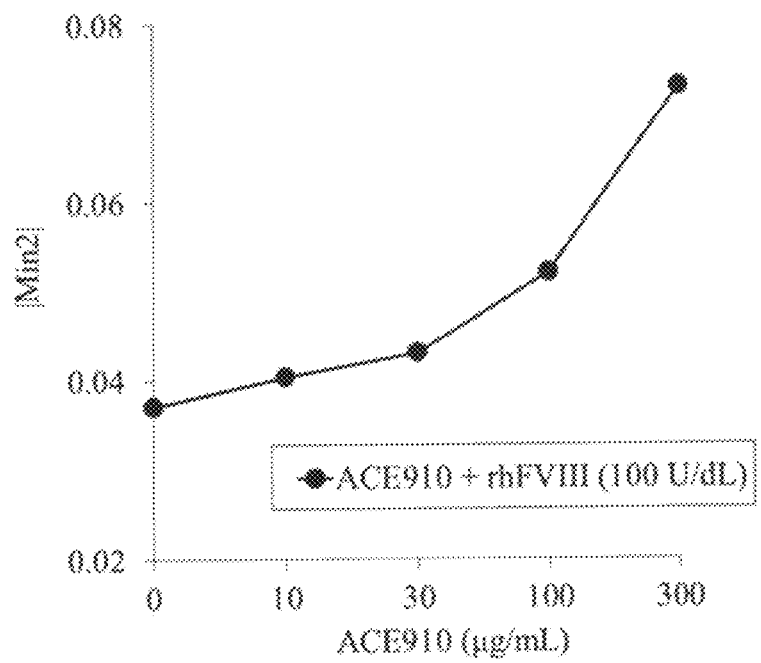
[Fig. 31J]
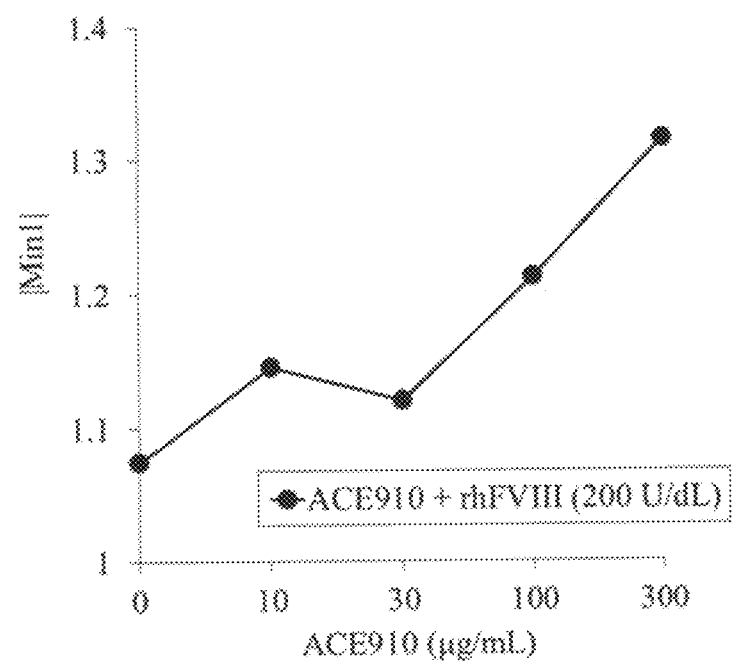

[Fig. 31K]
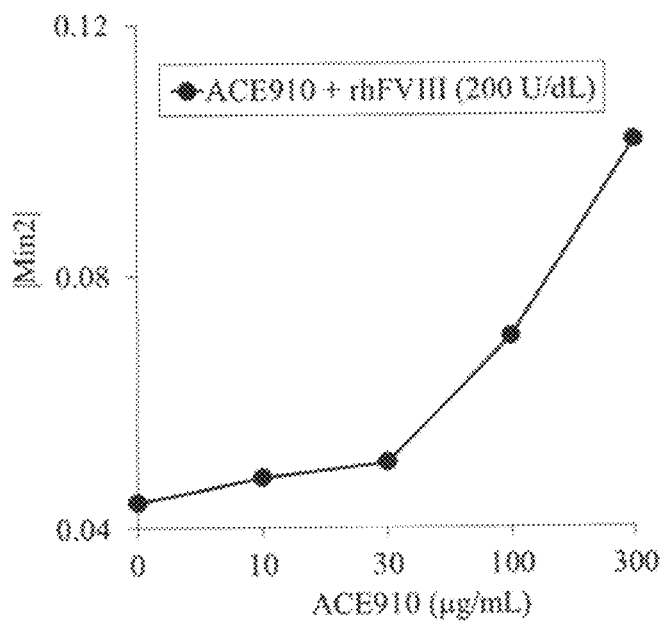
[Fig. 32A]
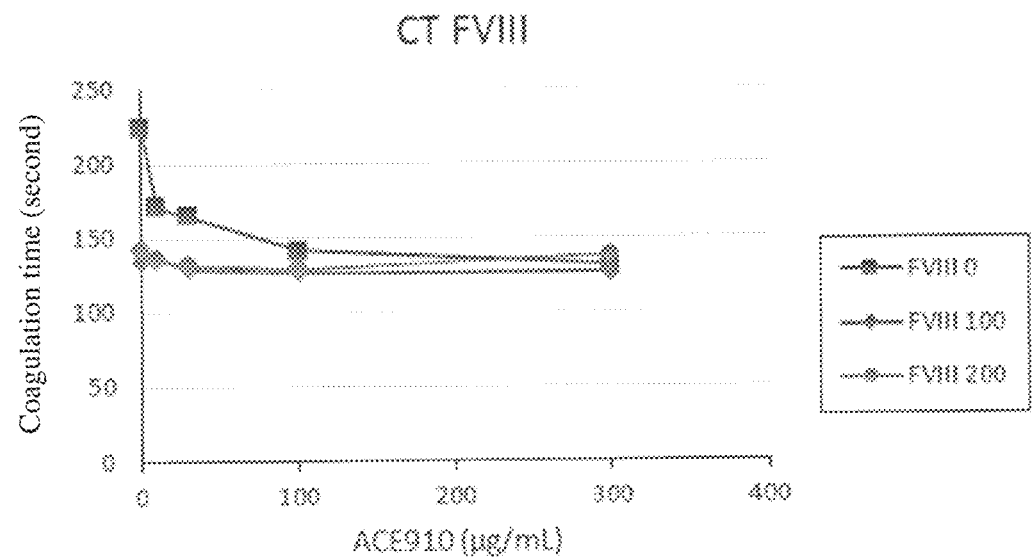

[Fig. 32B]
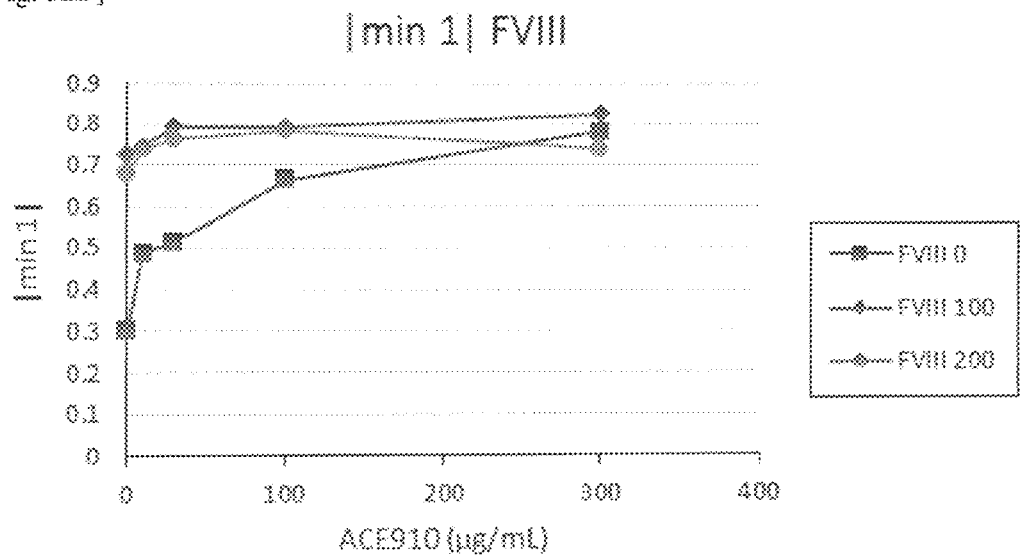
[Fig. 32C]
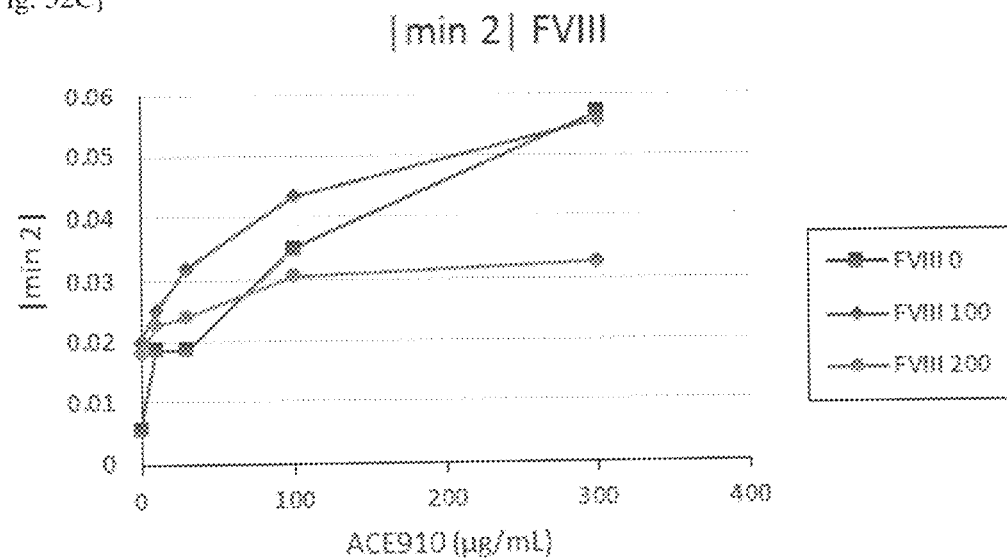

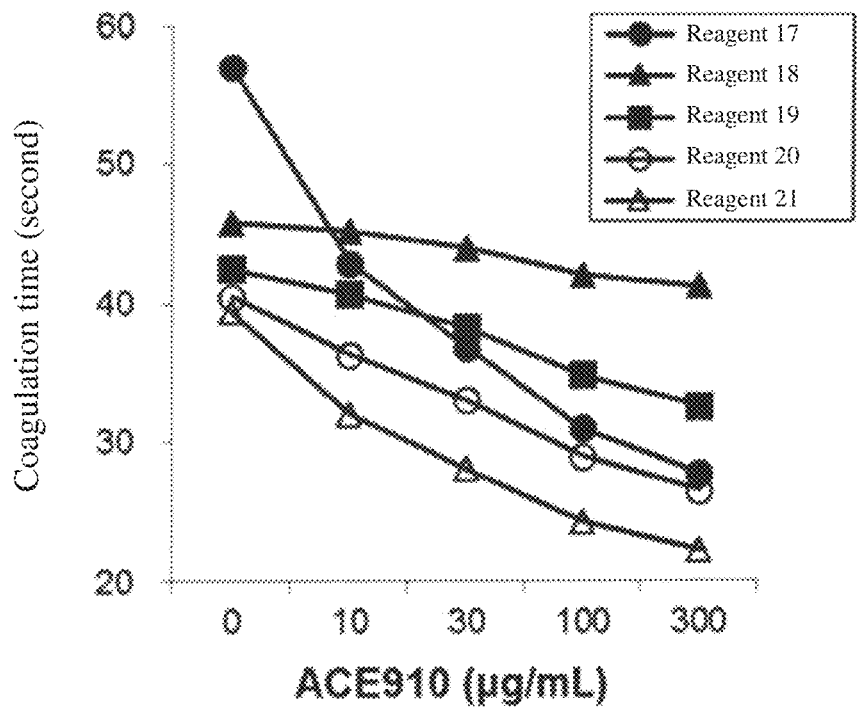
[Fig. 33A]
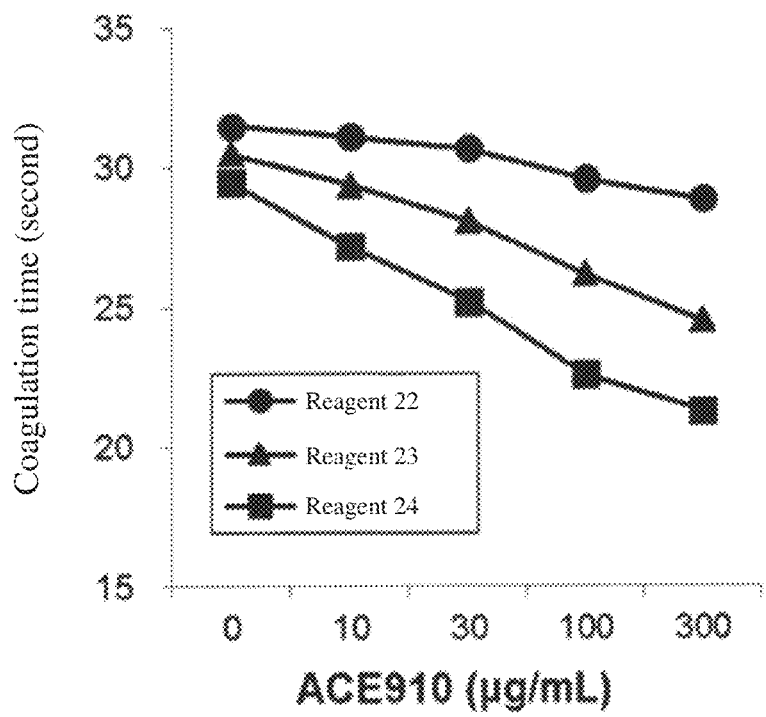
[Fig. 33B]

[Fig. 33C]
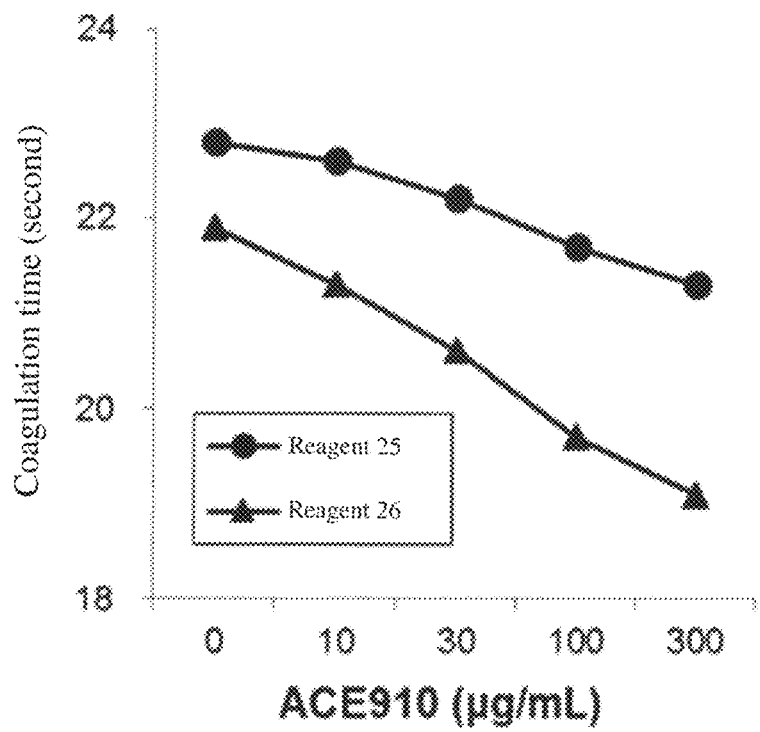
[Fig. 33D]
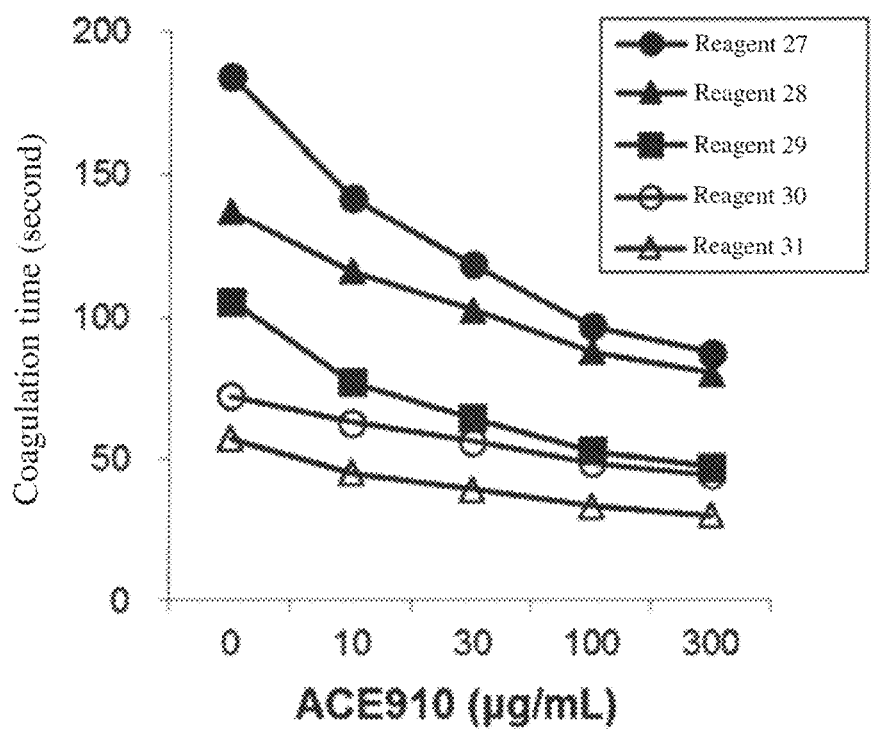

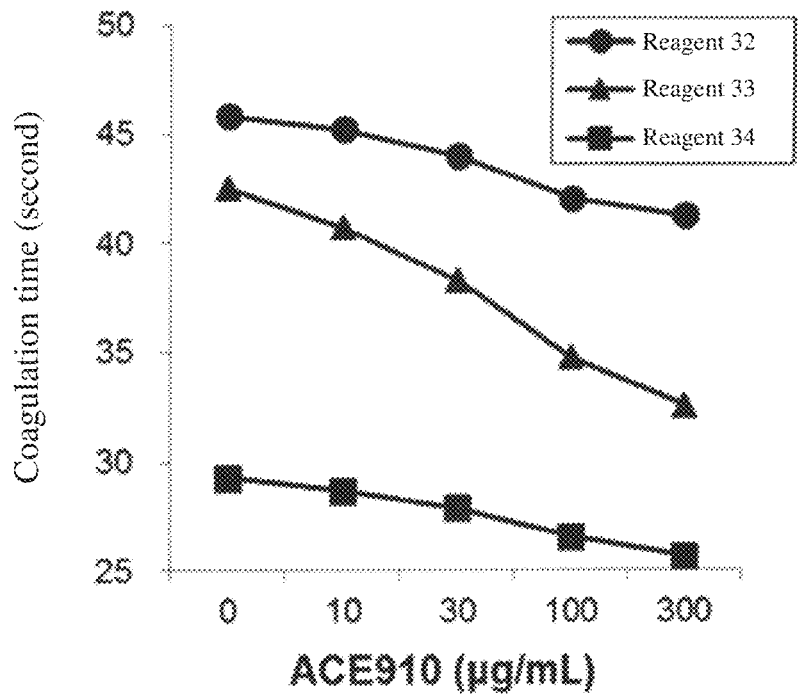
[Fig. 33E]
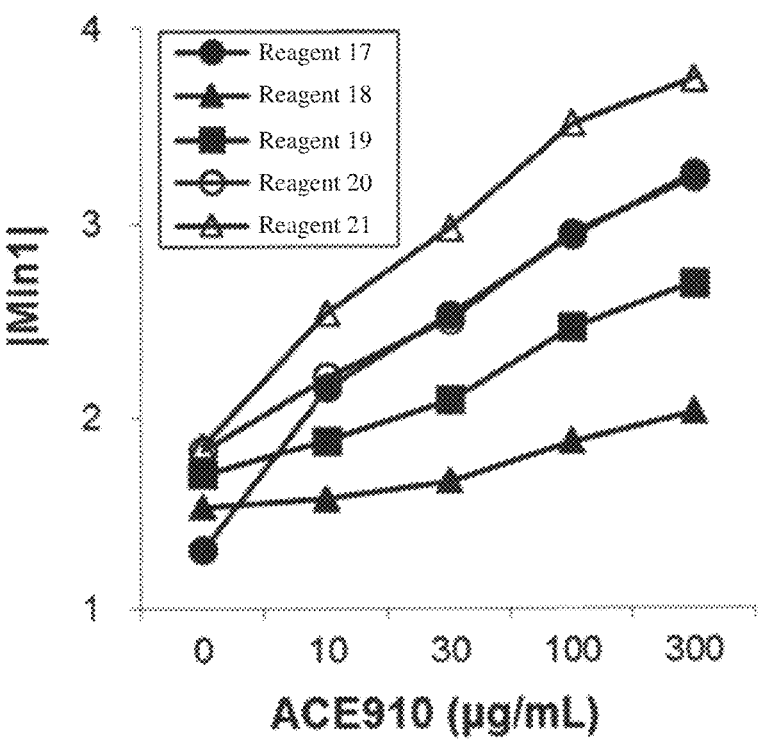
[Fig. 34A]

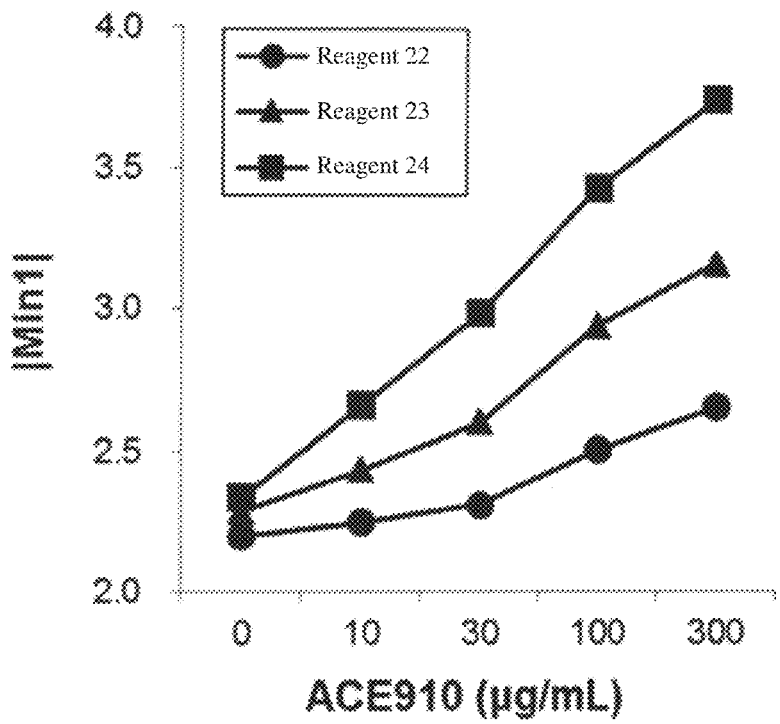
[Fig. 34B]
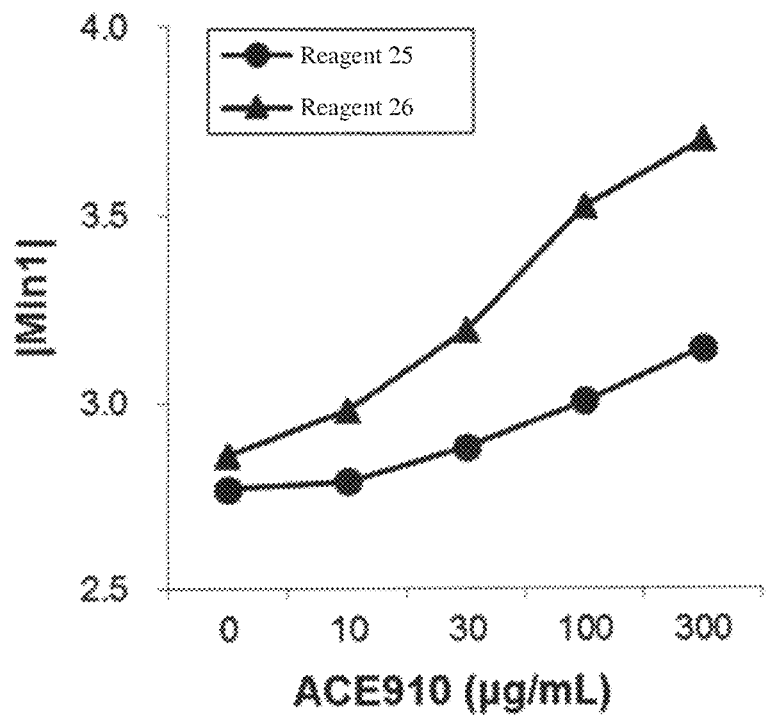
[Fig. 34C]

[Fig. 34D]
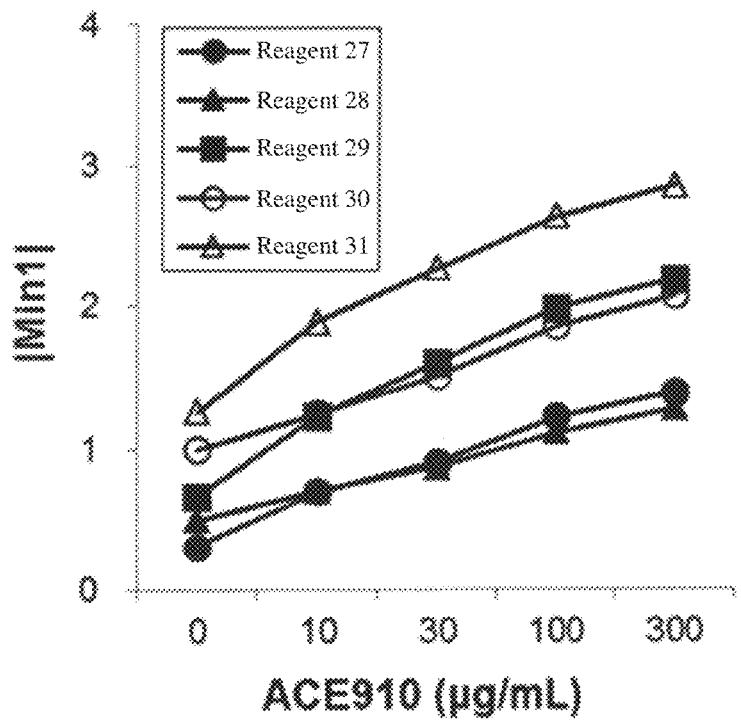
[Fig. 34E]
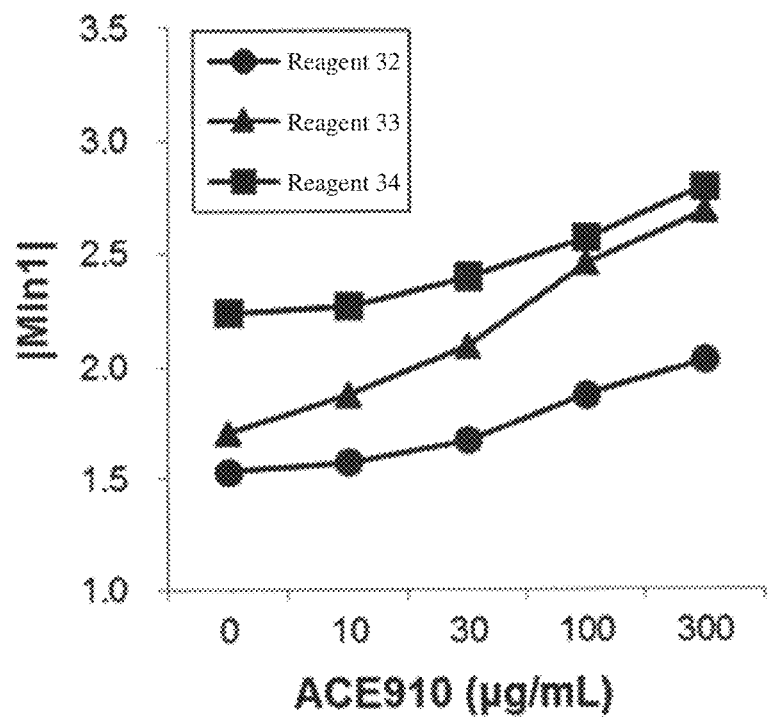

[Fig. 35A]
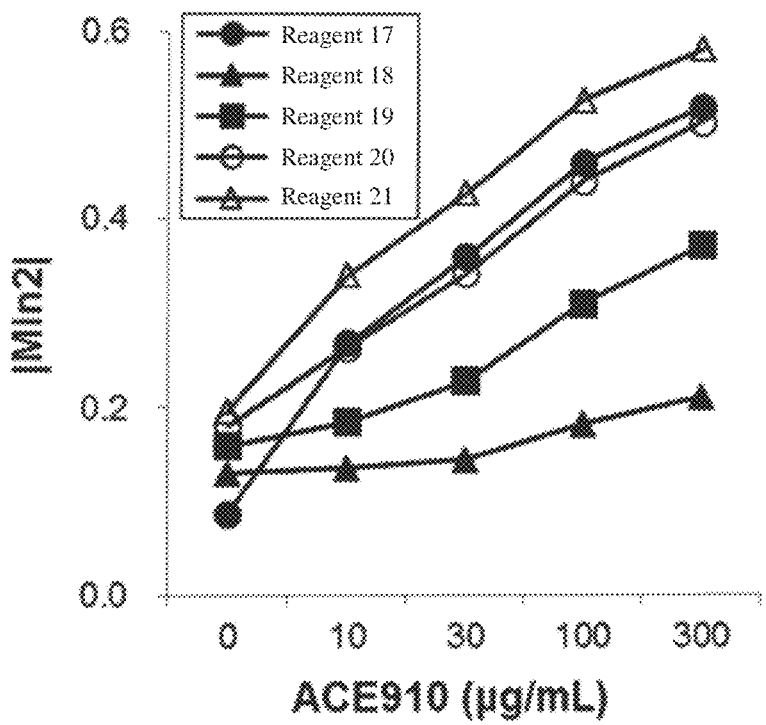
[Fig. 35B]
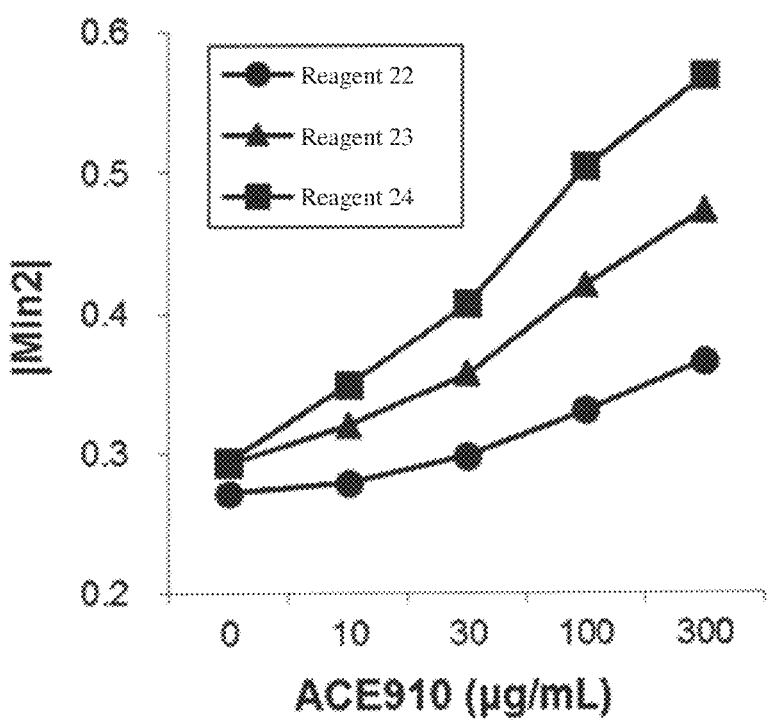

[Fig. 35C]
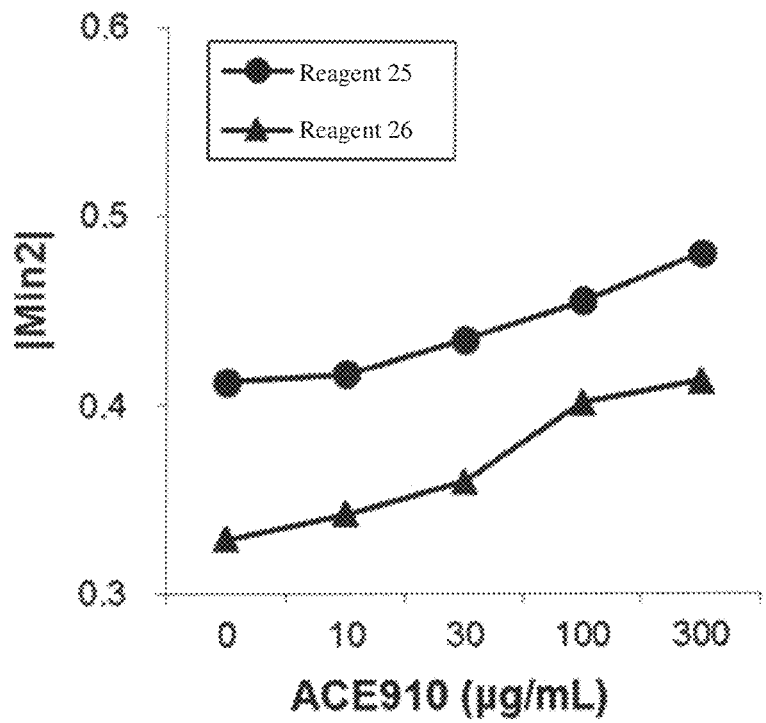
[Fig. 35D]
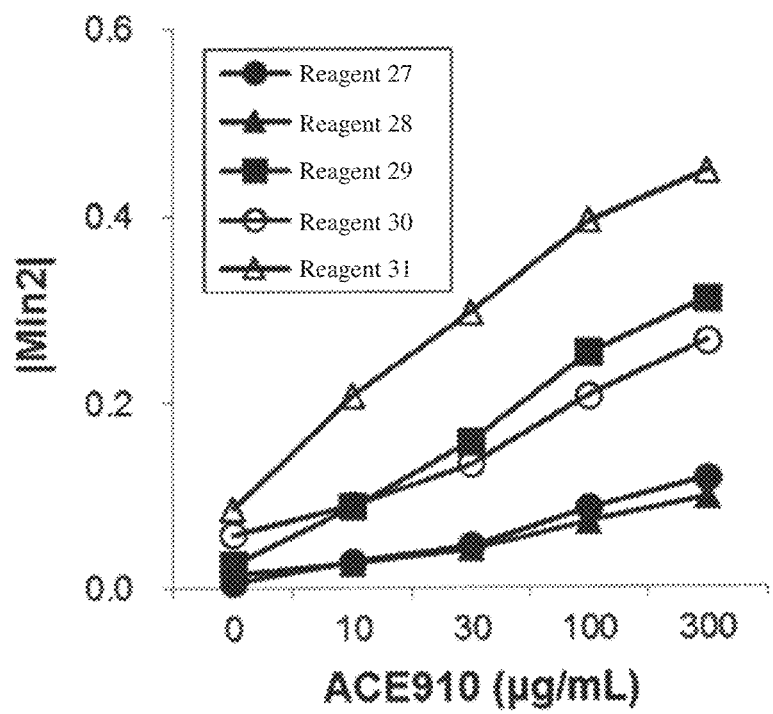

[Fig. 35E]
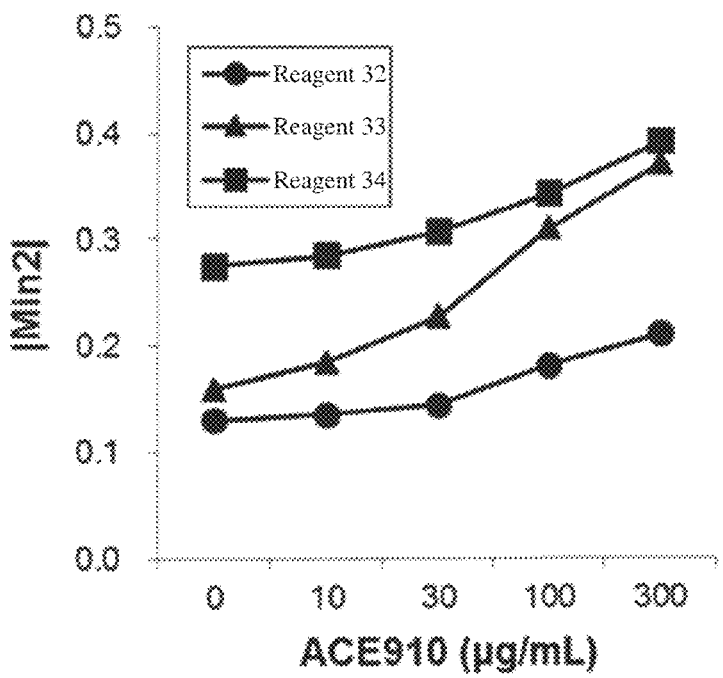
[Fig. 36A]
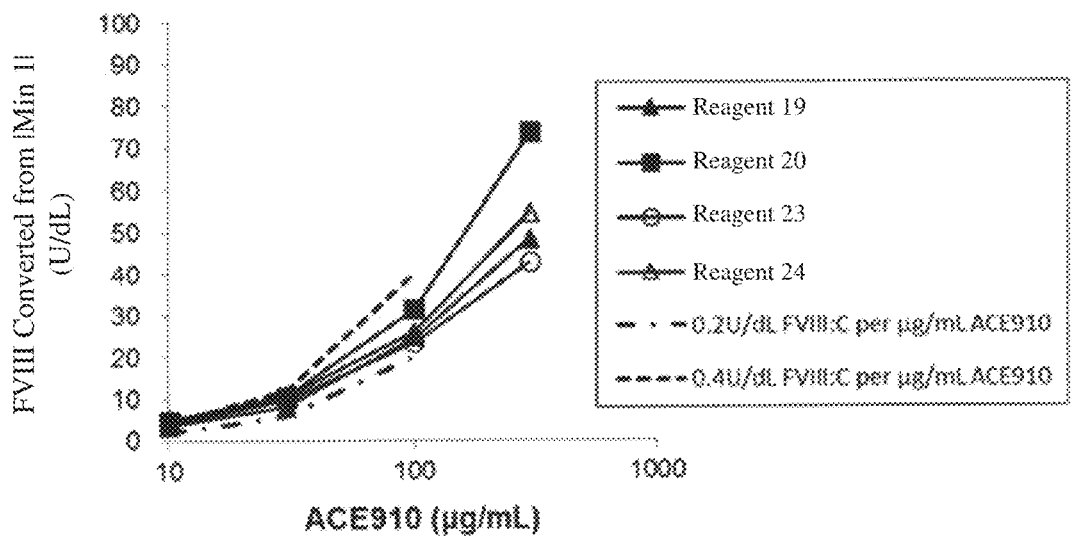

[Fig. 36B]
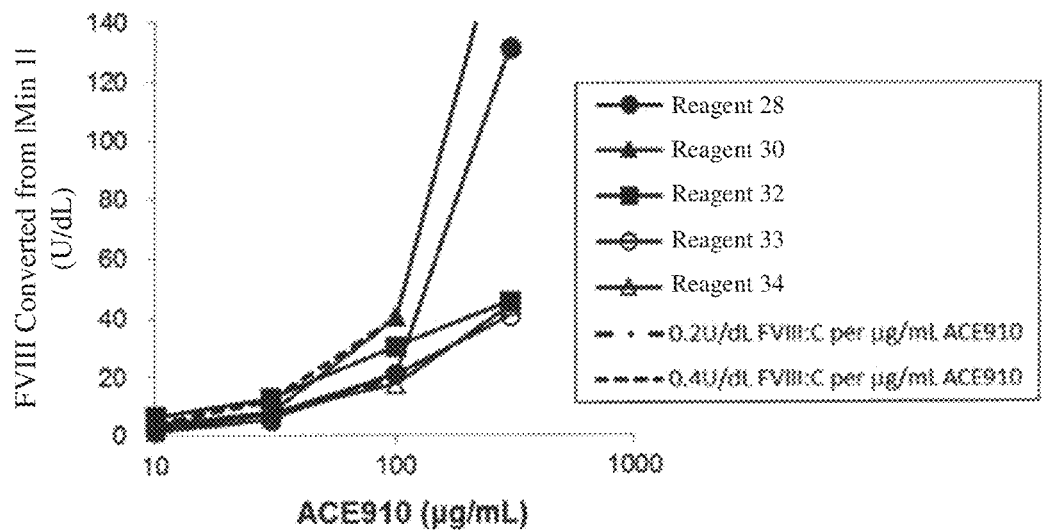
[Fig. 37A]
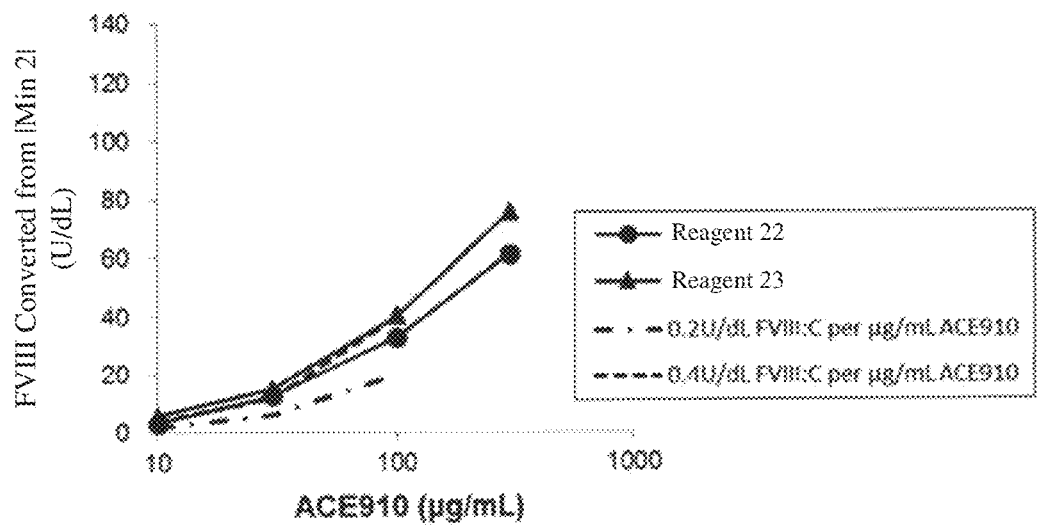

[Fig. 37B]
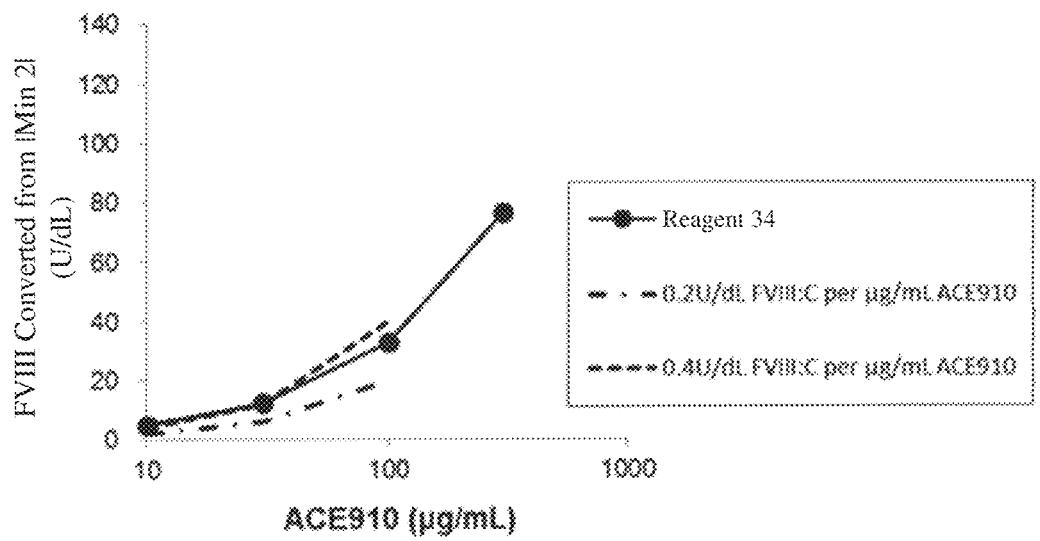
[Fig. 38A]
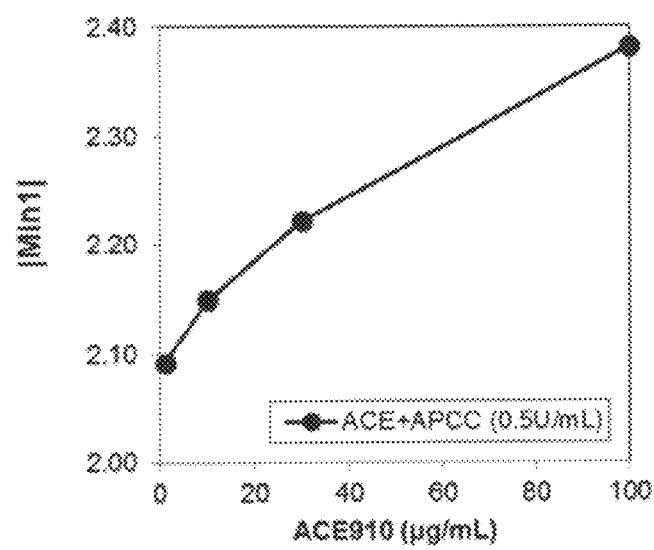

[Fig. 38B]
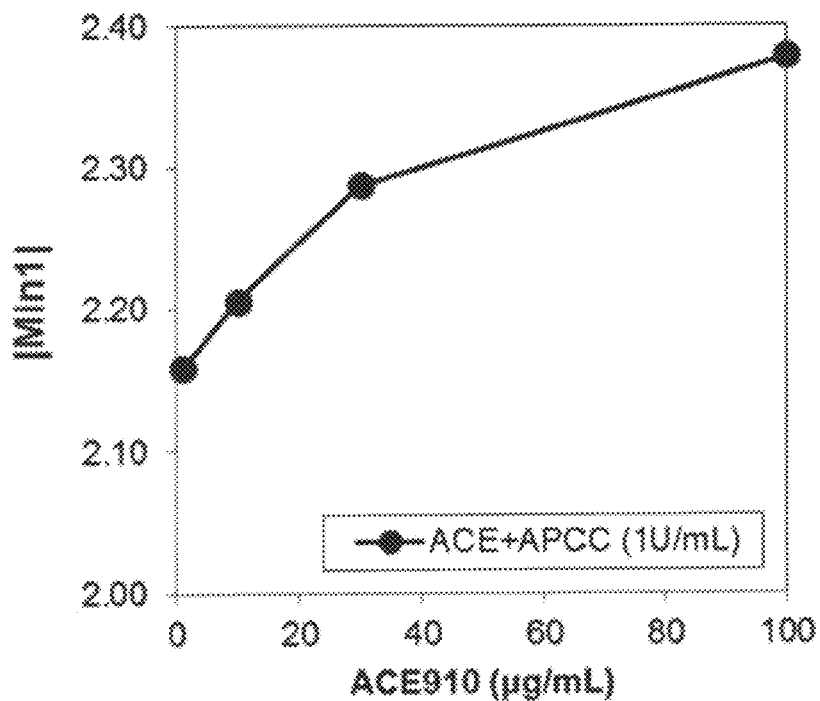
[Fig. 38C]
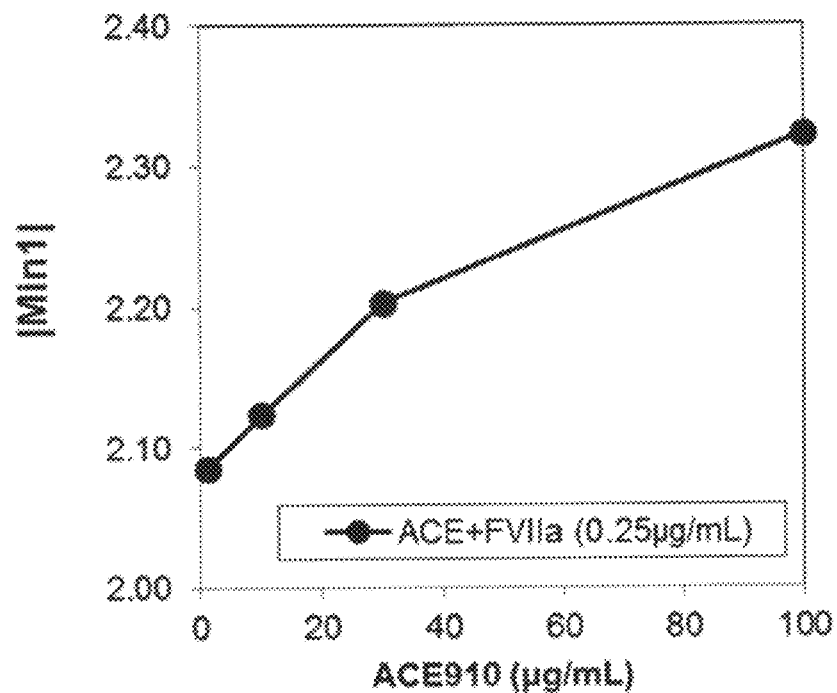

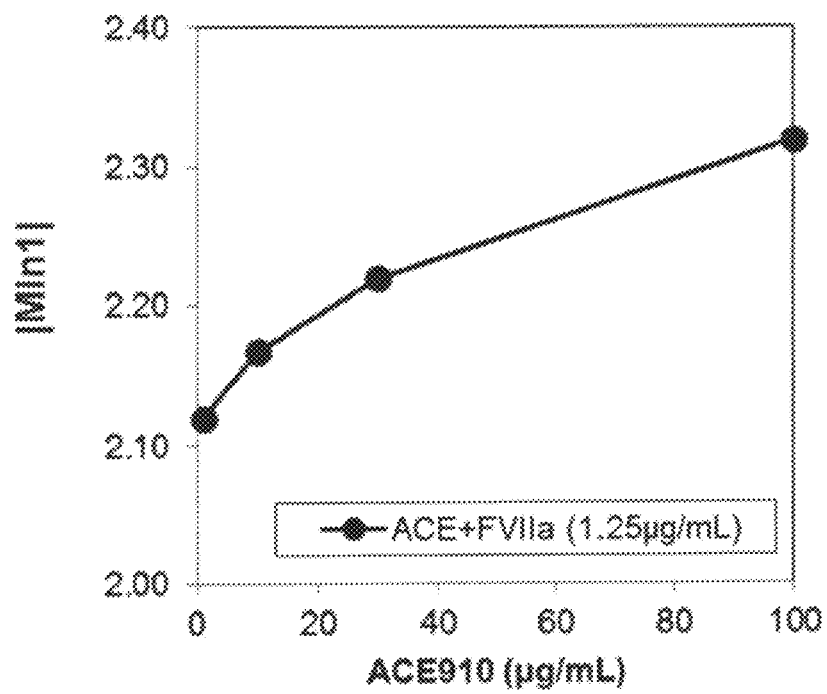
[Fig. 38D]
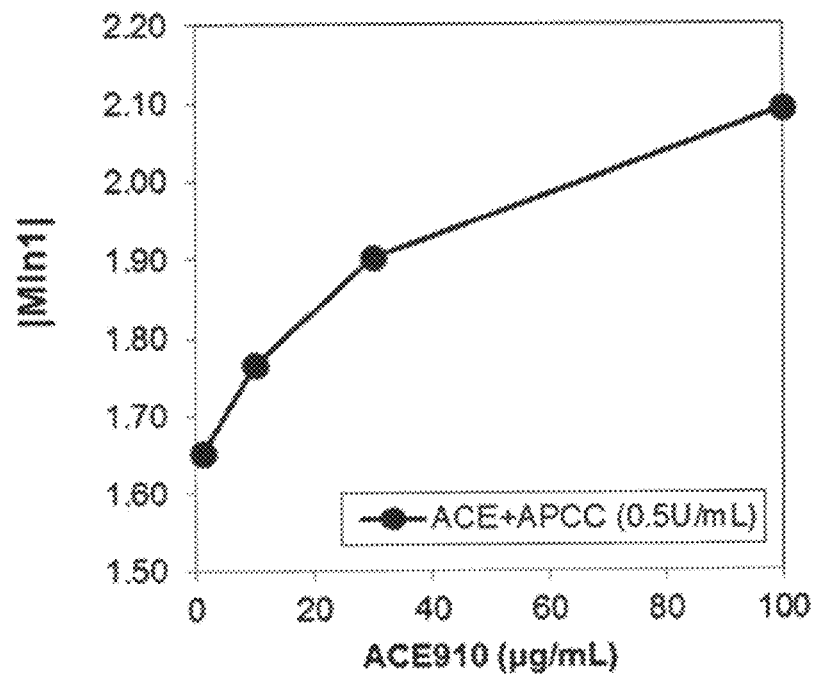
[Fig. 39A]

[Fig. 39B]
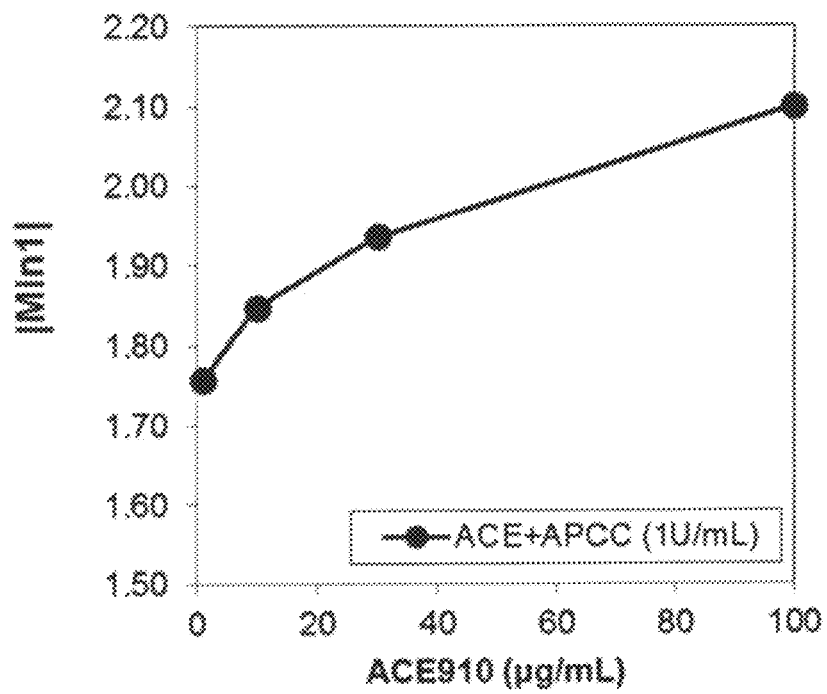
[Fig. 39C]
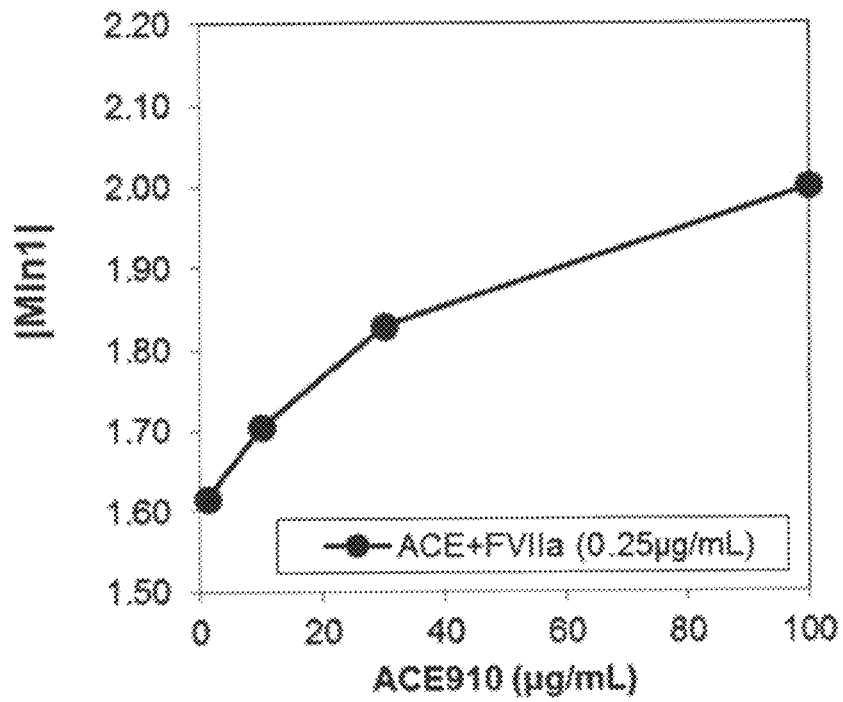

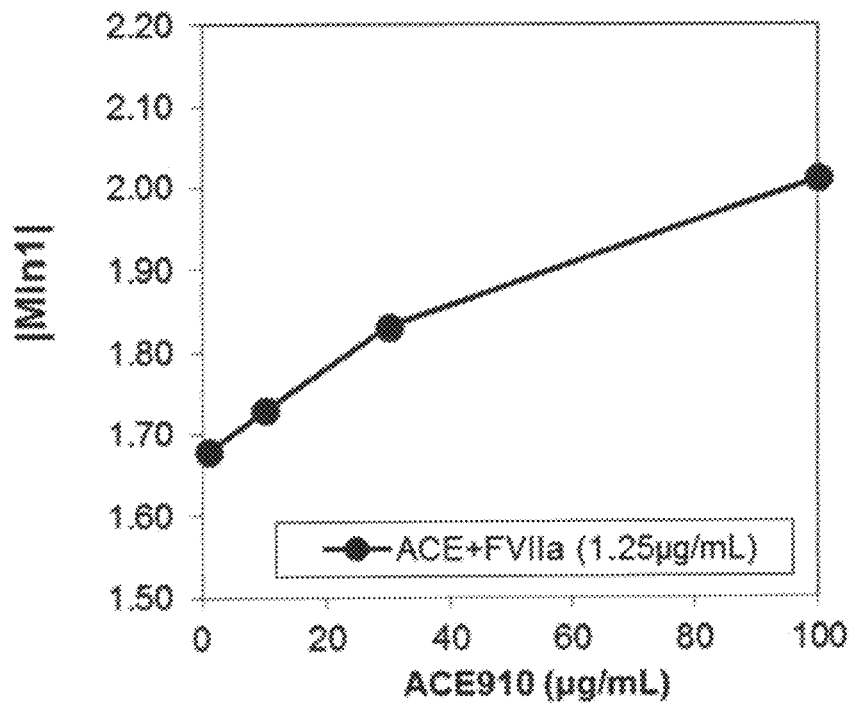
[Fig. 39D]
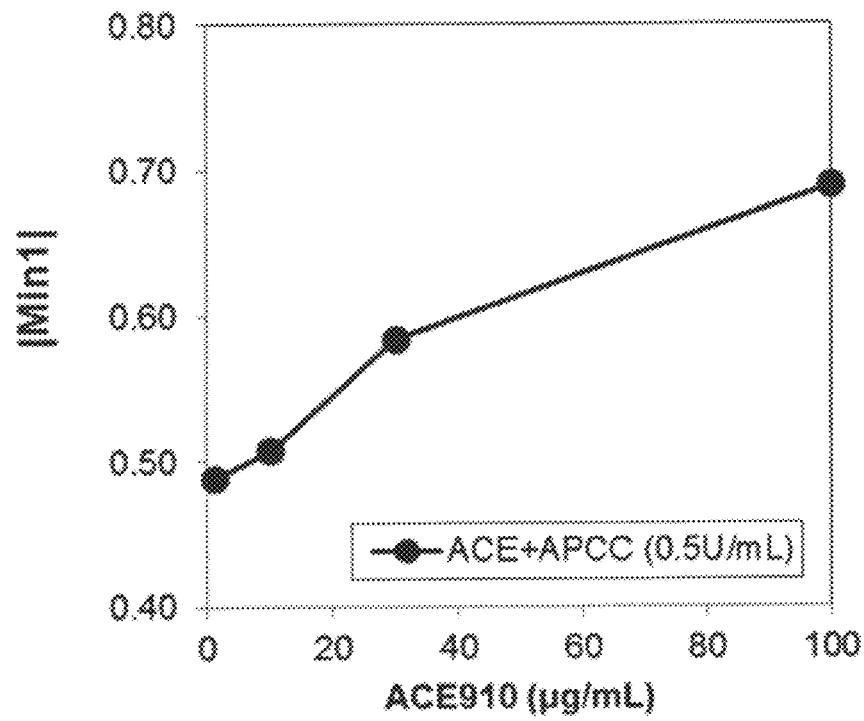
[Fig. 40A]

[Fig. 40B]
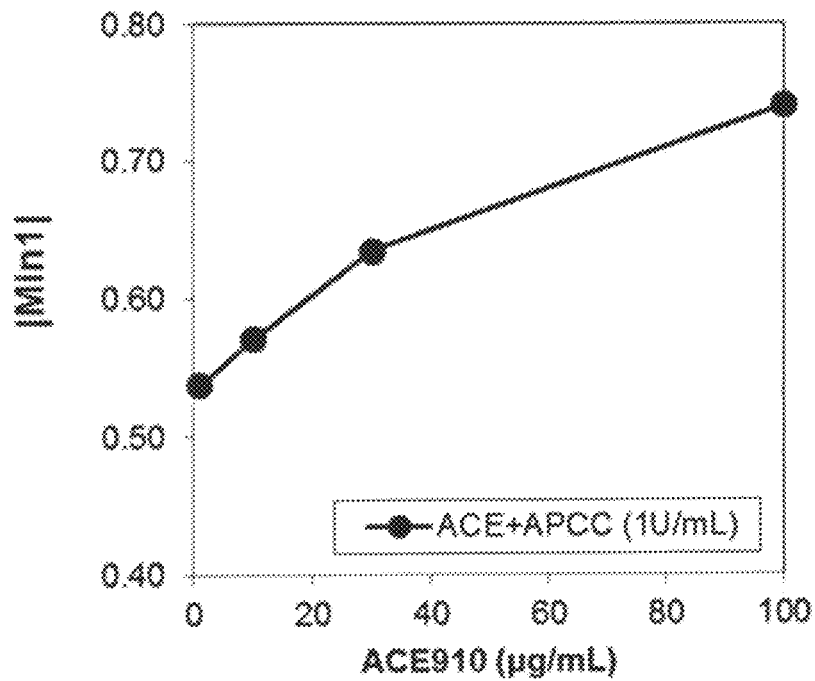
[Fig. 40C]
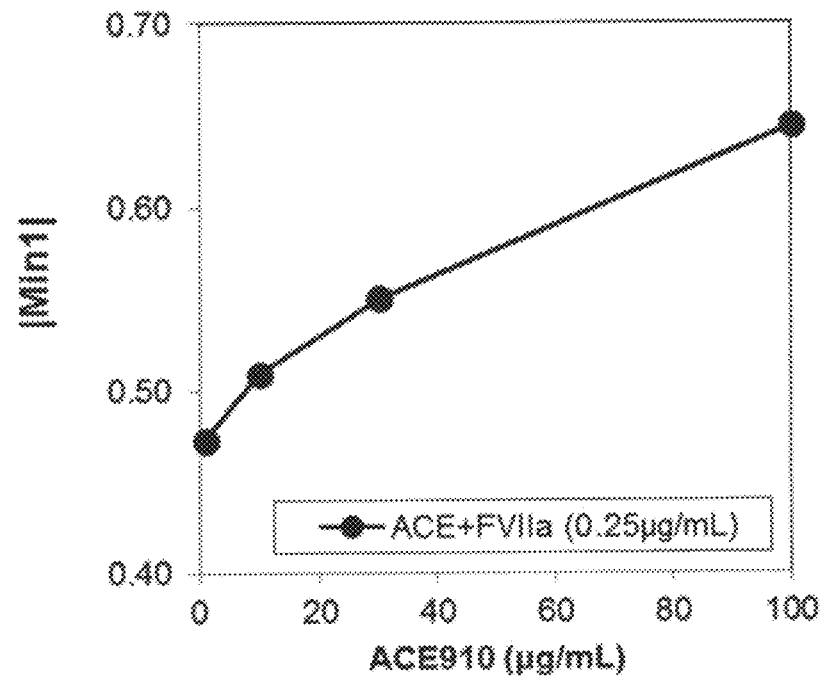

[Fig. 40D]
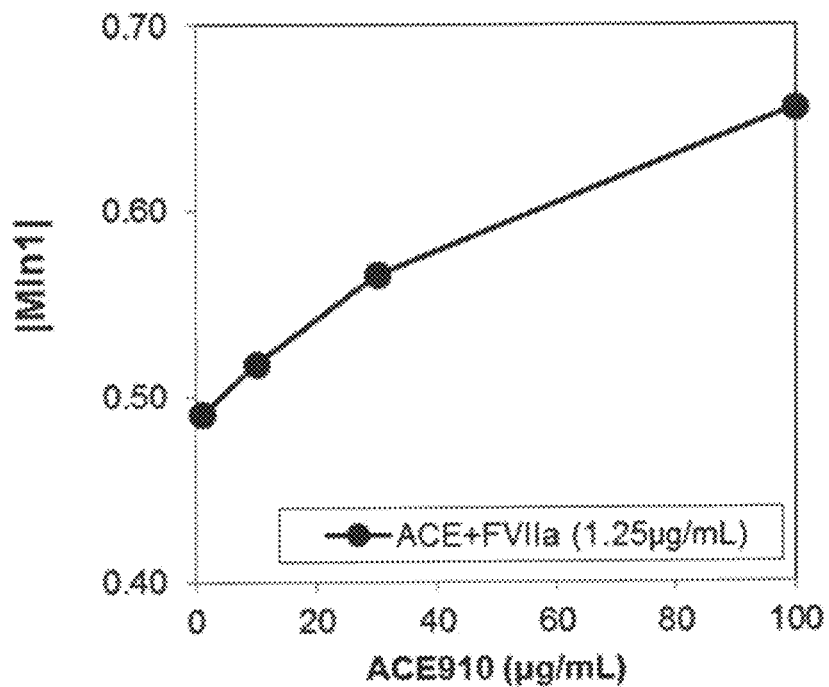
[Fig. 41A]
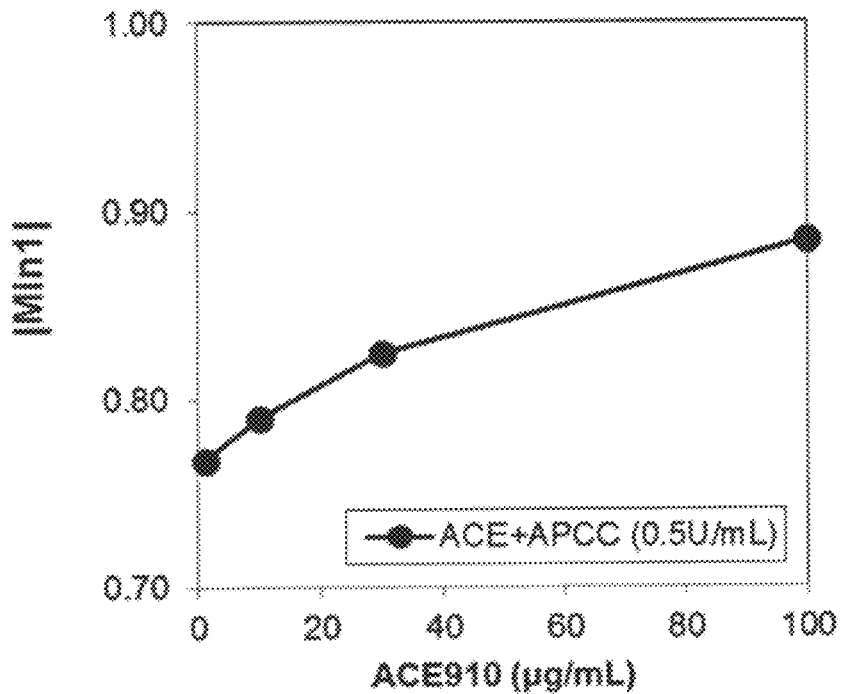

[Fig. 41B]
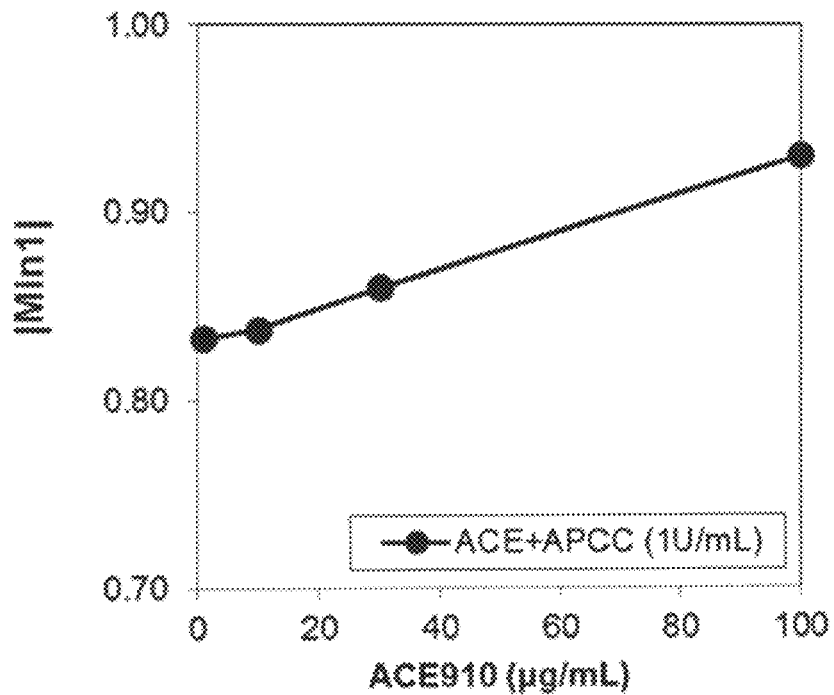
[Fig. 41C]
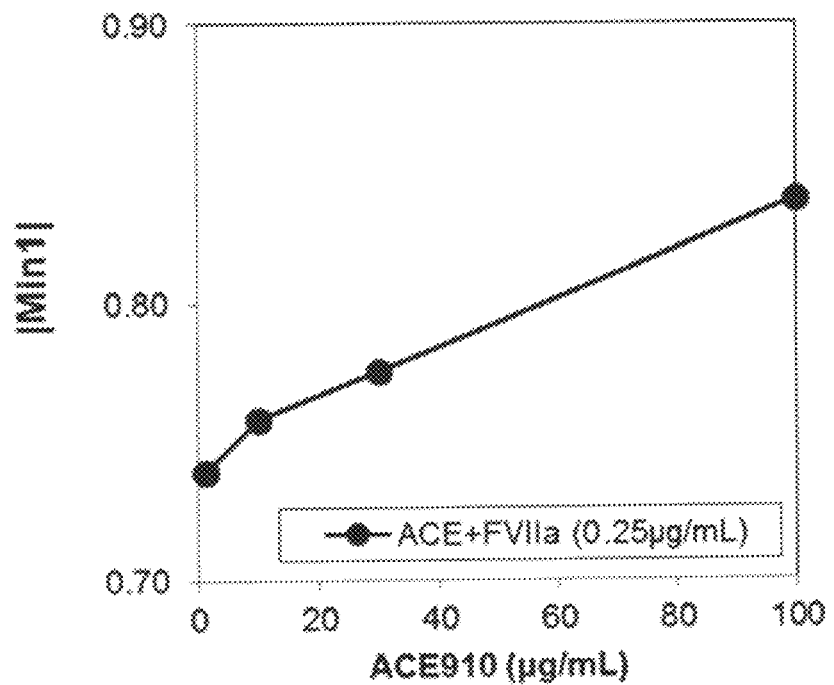

[Fig. 41D]
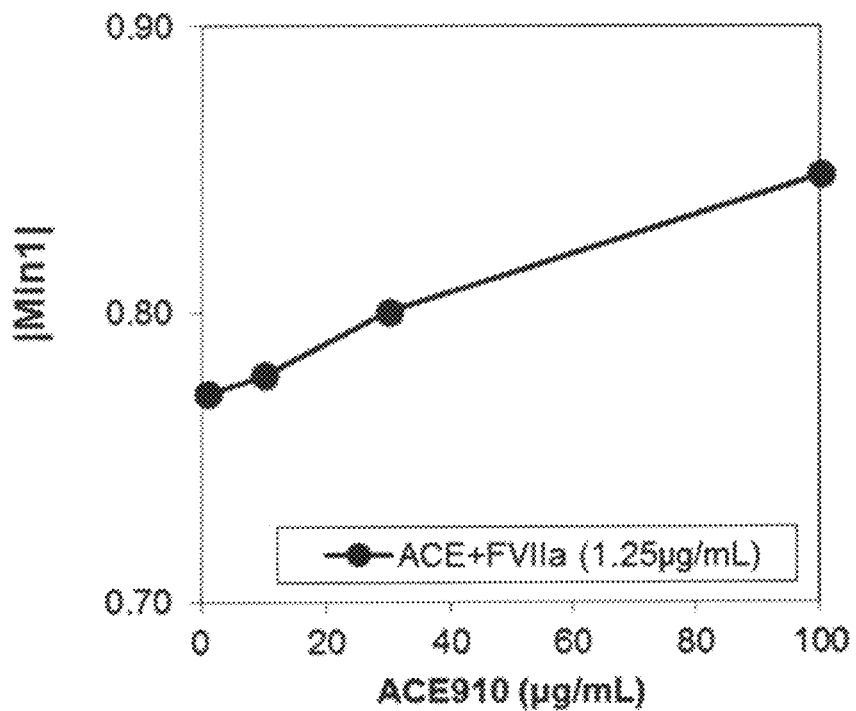
[Fig. 42A]
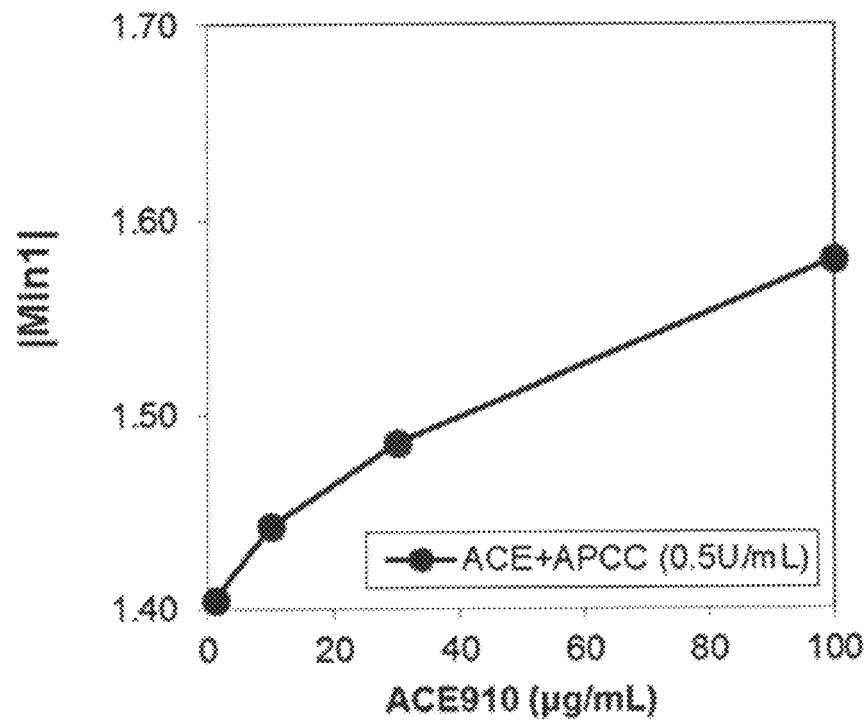

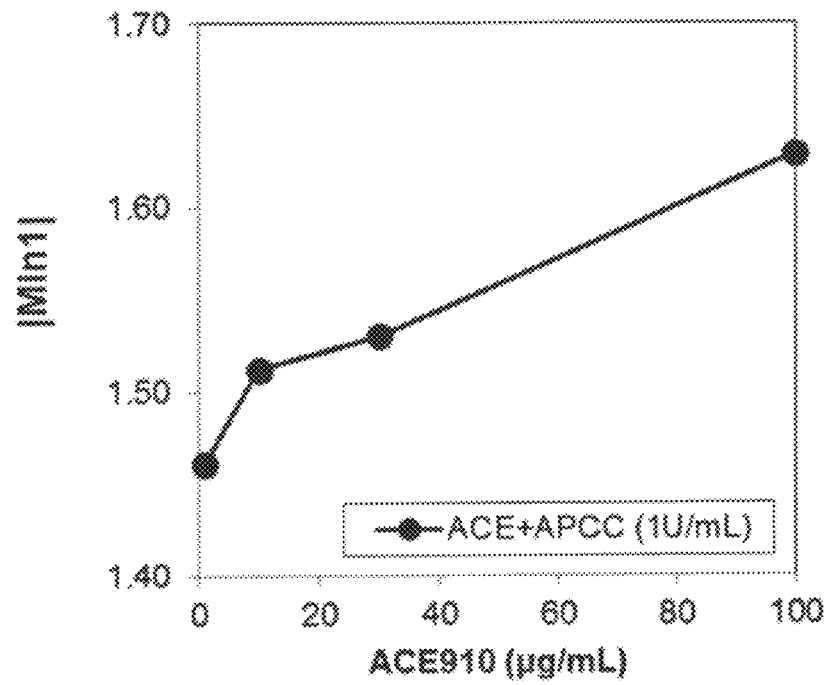
[Fig. 42B]
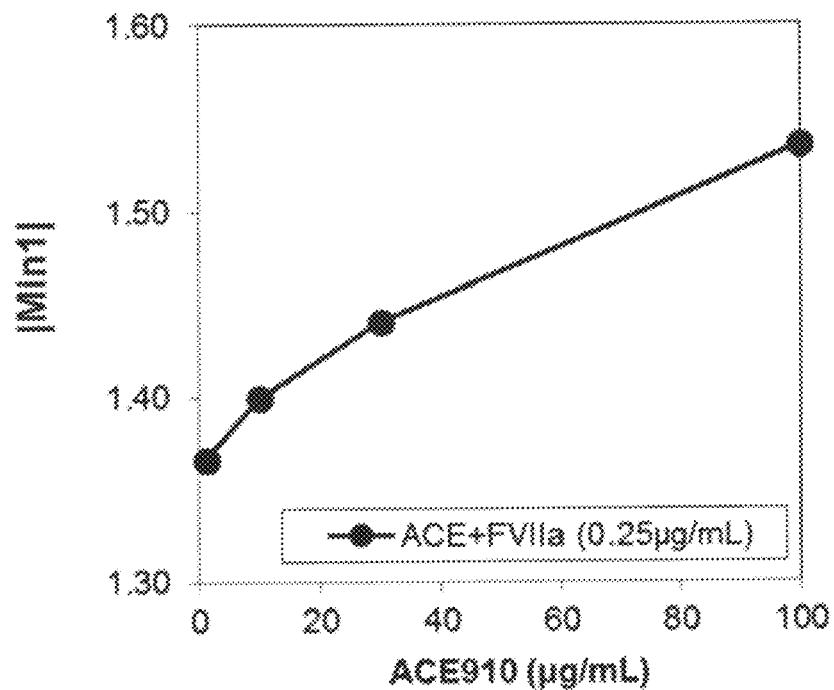
[Fig. 42C]

[Fig. 42D]
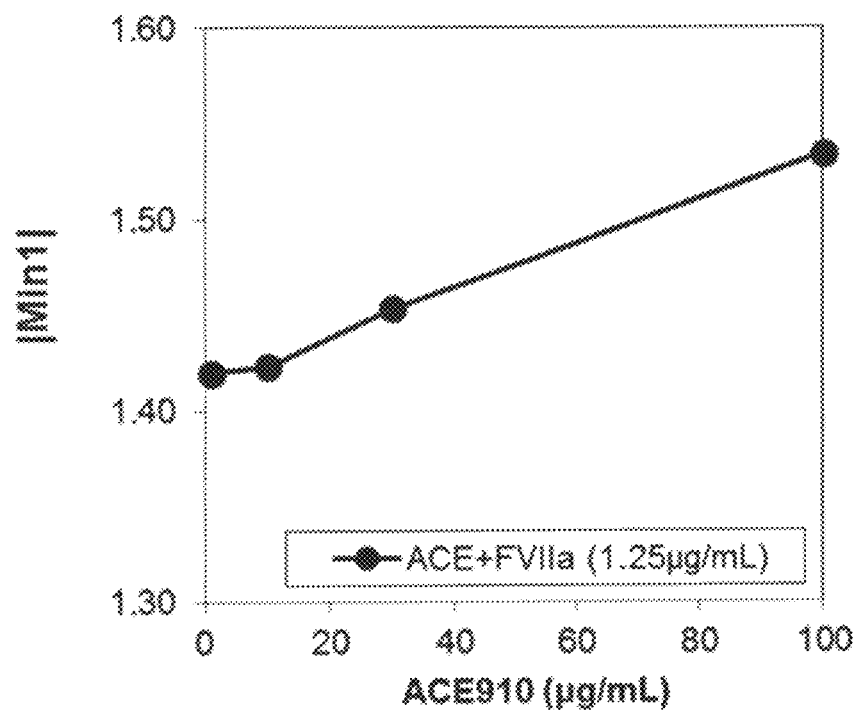
[Fig. 43A]
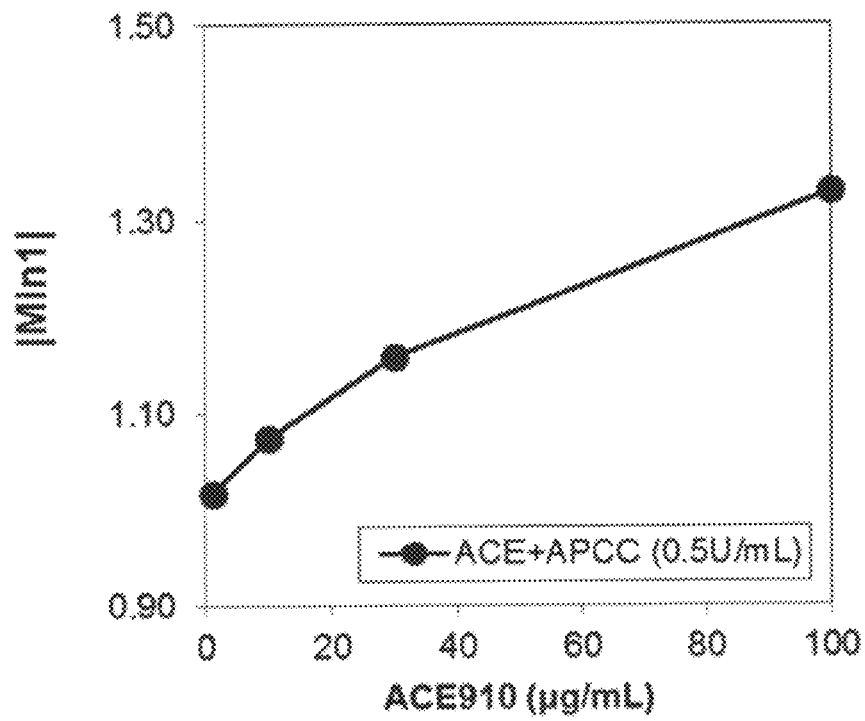

[Fig. 43B]
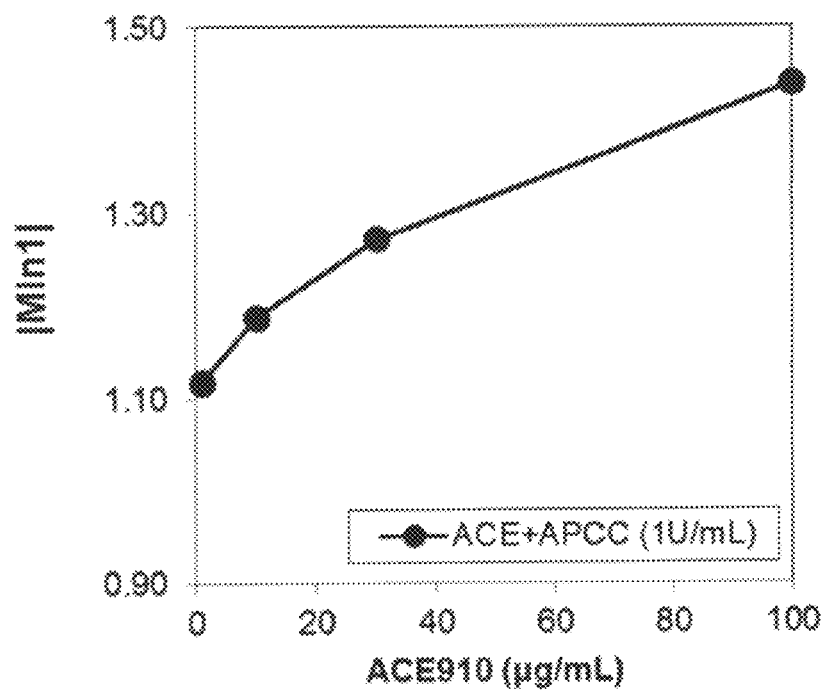
[Fig. 43C]
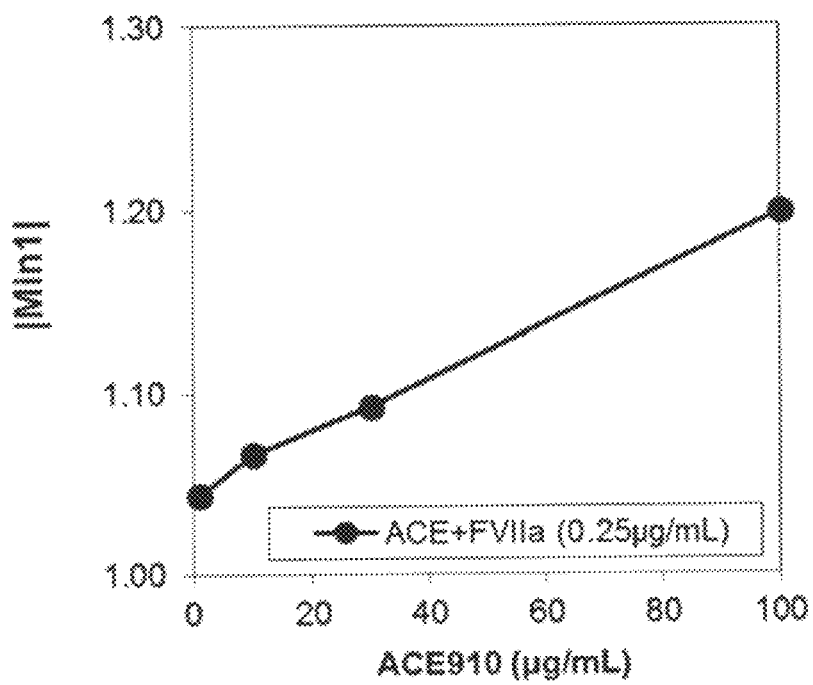

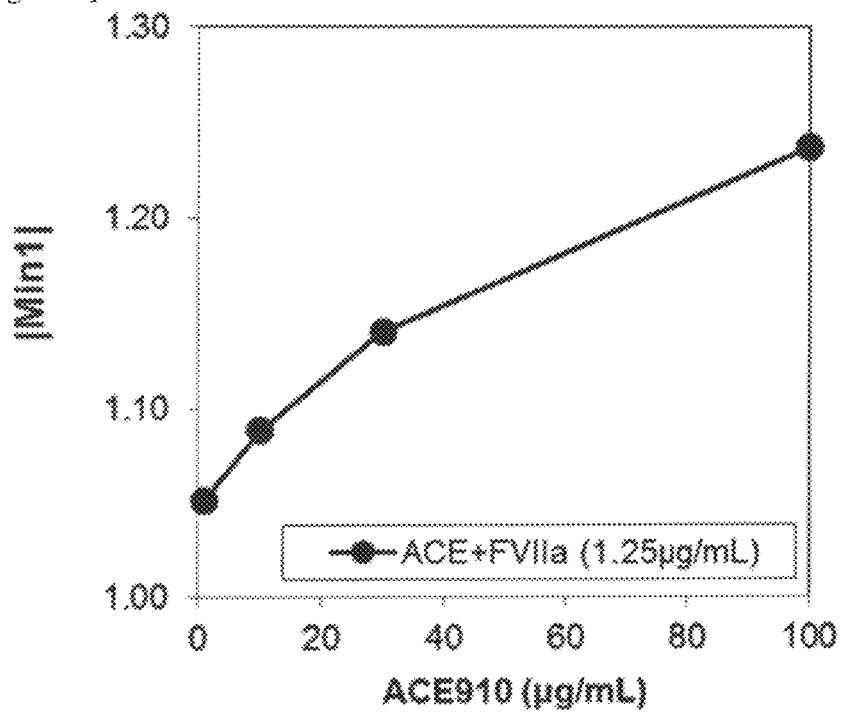
[Fig. 43D]
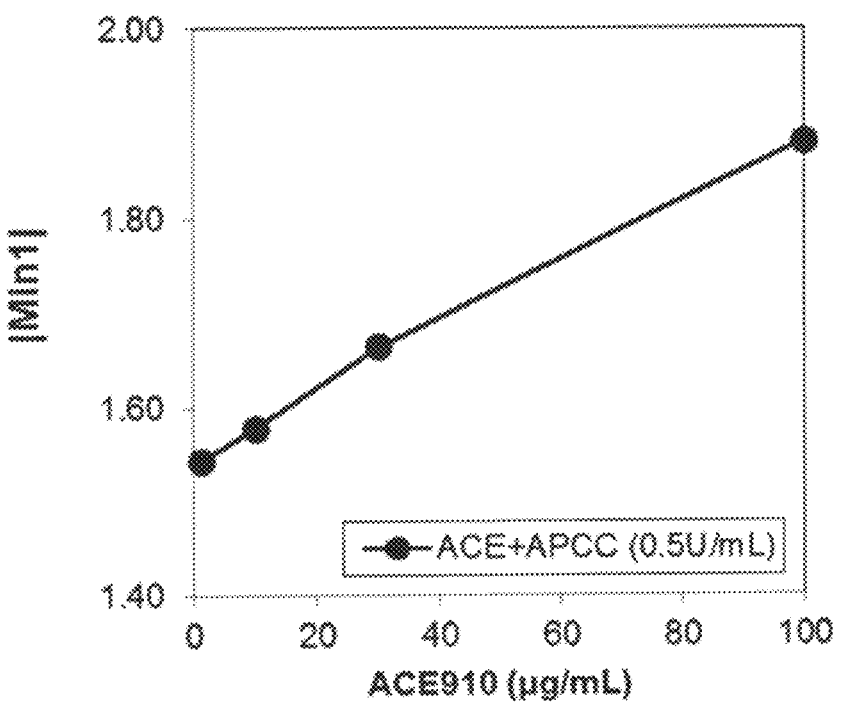
[Fig. 44A]

[Fig. 44B]
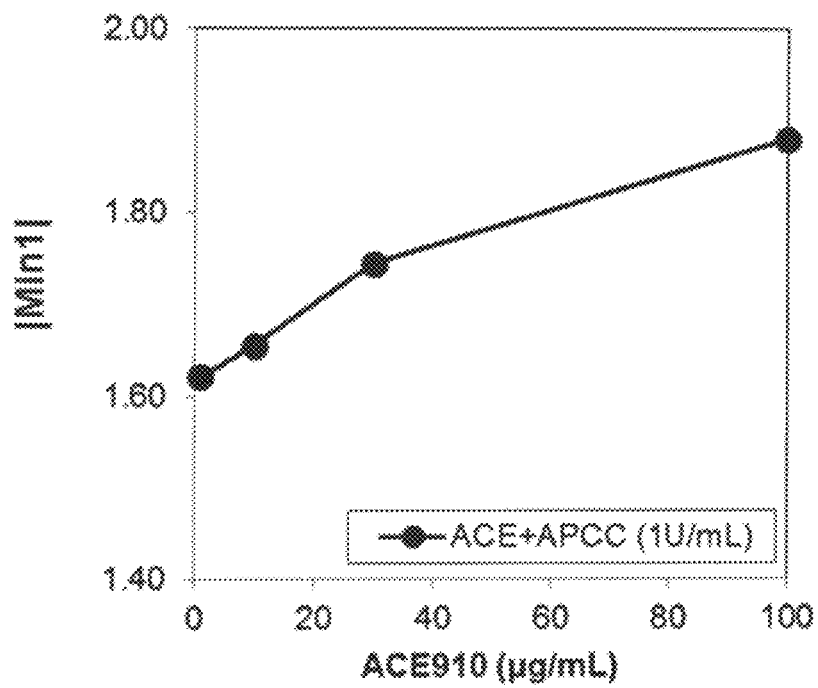
[Fig. 44C]
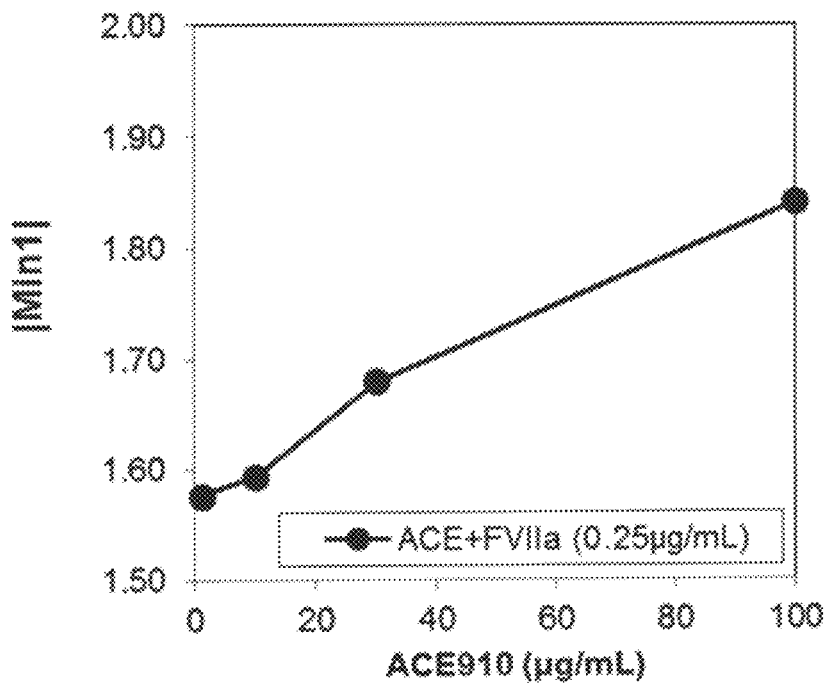

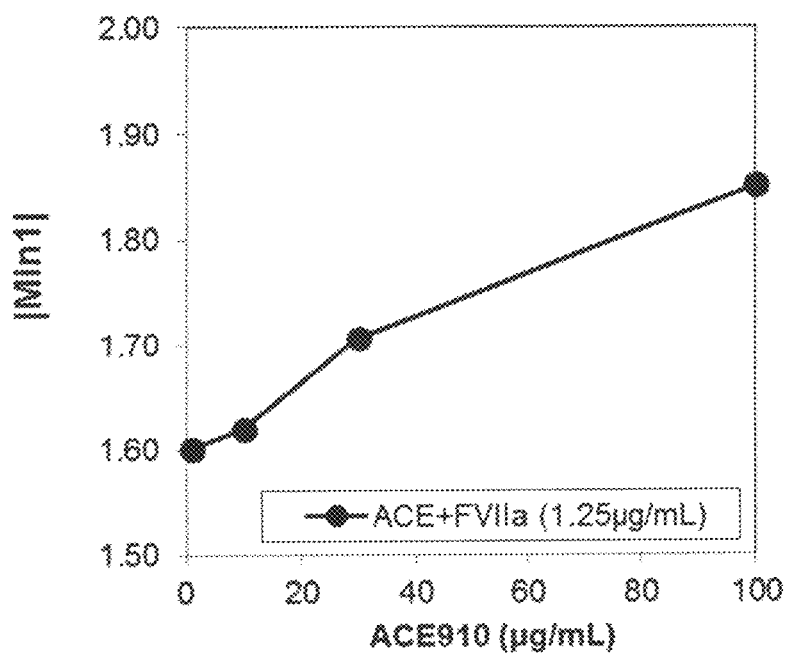
[Fig. 44D]

METHOD FOR EVALUATING COAGULATION ABILITY OF BLOOD SPECIMEN, AND REAGENT, REAGENT KIT AND DEVICE TO BE USED THEREIN

TECHNICAL FIELD

The present invention relates to a method for evaluating coagulability of a blood specimen obtained from a subject to whom a substance having a coagulation factor VIII-substituting activity is administered. The present invention also relates to a reagent for blood coagulation analysis, a reagent kit for blood coagulation analysis, and an apparatus for blood coagulation analysis. Furthermore, the present invention relates to an apparatus and computer program for evaluating coagulability of a blood specimen.

BACKGROUND ART

Hemophilia is a hemorrhagic disease caused by congenital defect or dysfunction of coagulation factor VIII (FVIII) or coagulation factor IX (FIX). Hemophilia is called hemophilia A when it is caused by FVIII and called hemophilia B when it is caused by FIX. In hemophilic patients, bleeding symptoms are found in deep tissues such as intraarticular tissues or intramuscular tissues, and intracranial hemorrhage also occurs in severe cases.

The severity of hemophilia is classified based on FVIII activity or FIX activity in the blood. Specifically, patients with an activity of less than 1% are classified as severe, patients with an activity of 1% or more and less than 5% are classified as moderate, and patients with an activity of 5% or more and less than 40% are classified as mild, based on the FVIII activity or FIX activity of a healthy subject as 100%. Patients with severe hemophilia present bleeding symptoms at a significantly higher frequency compared to moderate and mild patients. However, replacement therapy with FVIII or FIX can dramatically reduce the frequency of bleeding by maintaining FVIII activity or FIX activity in the patient's blood at 1% or more.

For replacement therapy, a coagulation factor preparation purified from plasma or prepared by genetic recombination technology is mainly used. In recent years, a bispecific antibody having a FVIII-substituting activity has been developed. This bispecific antibody substitutes for the function as a cofactor of activated coagulation factor VIII (FVIIIa). That is, this bispecific antibody can promote the activation of FX by FIXa by binding to both activated coagulation factor IX (FIXa) and coagulation factor X (FX). This promotes blood coagulation. Meanwhile, the process of blood coagulation promoted by the bispecific antibody does not require activation from FVIII to FVIIIa unlike the normal process by FVIII.

In replacement therapy using a coagulation factor preparation such as FVIII, the efficacy of the administered coagulation factor is monitored by activated partial thromboplastin time (APTT) measurement, coagulation waveform analysis, and the like. However, as described above, since blood coagulation by a bispecific antibody is different from normal blood coagulation by FVIII, it has been difficult to acquire data reflecting the actual efficacy of a bispecific antibody by the existing method for monitoring the efficacy of a coagulation factor preparation.

Under such circumstances, the present inventors have found so far that the efficacy of a substance having a FVIII-substituting activity can be evaluated with appropriate sensitivity using the thrombin generation amount in a blood specimen as an index (see Patent Literature 1). However, this method requires a special measuring equipment, so it has not been widely spread as a clinical test. In addition, the present inventors have found that the factor VIII-substituting activity of the bispecific antibody can be measured by coagulation waveform analysis using a commercially available APTT measuring reagent (see Non Patent Literature 1). However, with this method, the efficacy of the bispecific antibody could not be evaluated with appropriate sensitivity.

CITATIONS LISTS

Patent Literature

Patent Literature 1: WO 2014/050926

Non Patent Literature

Non Patent Literature 1: Matsumoto T. et al., A novel bispecific antibody (ACE910) againstcoagulation factors IXa and X improves procoagulant activity of patients with hemophilia A ex vivo to hemostatic level, ISTH, Abstract, OC 37.3. Jul. 2, 2013

Non Patent Literature 2: Muto A. et al., Anti-factor IXa/X bispecific antibody (ACE910): hemostatic potency against ongoing bleeds in a hemophilia A model and the possibility of routine supplementation, J Thromb Haemost. 2014 February; 12 (2): 206-13

SUMMARY OF INVENTION

Technical Problems

In order to use a substance having a FVIII-substituting activity such as the bispecific antibody for treatment of hemophilia or the like, it is important to establish a method capable of appropriately evaluating the efficacy of the substance. Accordingly, it is desirable to develop a means for appropriately evaluating coagulability of a blood specimen containing a substance having a FVIII-substituting activity. It is also desirable to develop a new means for evaluating the coagulability of a blood specimen. The present inventors have found conditions capable of appropriately evaluating coagulability of a blood specimen containing a substance having a FVIII-substituting activity, and a novel approach for evaluating the coagulability of a blood specimen, thereby the present invention has been completed.

Solutions to Problems

A first embodiment of the present invention provides a method for evaluating coagulability of a blood specimen. This method comprises the steps of preparing a measurement sample from a blood specimen obtained from a subject to whom a substance having a coagulation factor VIII-substituting activity is administered, a coagulation factor XII-activating agent, phospholipids, and a calcium ion-containing aqueous solution, irradiating the measurement sample with light to acquire optical information on the light amount from the measurement sample, acquiring at least one parameter on differentiation of coagulation waveform based on the acquired optical information, and evaluating coagulability of the blood specimen based on the value of the acquired parameter, wherein the final concentration of the factor XII-activating agent is 1 µM or more and 22 µM or less, and the final concentration of the phospholipids is 1.4 µM or more and 33 µM or less in the measurement sample, or the final concentration of the coagulation factor XII-activating agent is 1 µM or more and 2.9 µM or less, and the final concentration of the phospholipids is 1.4 µM or more and 43 µM or less in the measurement sample.

A second embodiment of the present invention provides a method for evaluating coagulability of a blood specimen. This method comprises the steps of preparing a measurement sample from a blood specimen obtained from a subject to whom a substance having a coagulation factor VIII-substituting activity is administered, a coagulation factor XII-activating agent, phospholipids, tissue factor, and a calcium ion-containing aqueous solution, irradiating the measurement sample with light to acquire optical information on the light amount from the measurement sample, and evaluating coagulability of the blood specimen based on the acquired optical information.

A third embodiment of the present invention provides a reagent for evaluating coagulability of a blood specimen obtained from a subject to whom a substance having a coagulation factor VIII-substituting activity is administered, containing a coagulation factor XII-activating agent at a concentration of 3 µM or more and 66 µM or less and phospholipids at a concentration of 4.2 µM or more and 99 µM or less, or containing a coagulation factor XII-activating agent at a concentration of 3 µM or more and 8.7 µM or less and phospholipids at a concentration of 4.2 µM or more and 129 µM or less.

A fourth embodiment of the present invention provides a reagent kit for evaluating coagulability of a blood specimen obtained from a subject to whom a substance having a coagulation factor VIII-substituting activity is administered, comprising a first reagent and a coagulation initiation reagent comprising a calcium ion-containing aqueous solution, wherein the first reagent contains a coagulation factor XII-activating agent at a concentration of 3 µM or more and 66 µM or less and phospholipids at a concentration of 4.2 µM or more and 99 µM or less, or the first reagent contains a coagulation factor XII-activating agent at a contains of 3 µM or more and 8.7 µM or less and phospholipids at a concentration of 4.2 µM or more and 129 µM or less.

A fifth embodiment of the present invention provides a reagent for evaluating coagulability of a blood specimen obtained from a subject to whom a substance having a coagulation factor VIII-substituting activity is administered, containing a coagulation factor XII-activating agent, phospholipids, and tissue factor.

A sixth embodiment of the present invention provides a reagent kit for evaluating coagulability of a blood specimen obtained from a subject to whom a substance having a coagulation factor VIII-substituting activity is administered, comprising a first reagent containing a coagulation factor XII-activating agent, phospholipids and tissue factor, and a coagulation initiation reagent comprising a calcium ion-containing aqueous solution.

A seventh embodiment of the present invention provides a reagent kit for evaluating coagulability of a blood specimen obtained from a subject to whom a substance having a coagulation factor VIII-substituting activity is administered, comprising a first reagent, a second reagent, and a coagulation initiation reagent comprising a calcium ion-containing aqueous solution, wherein the first reagent contains a coagulation factor XII-activating agent and phospholipids and the second reagent contains tissue factor, the first reagent contains a coagulation factor XII-activating agent and phospholipids and the second reagent contains tissue factor and phospholipids, or the first reagent contains a coagulation factor XII-activating agent and tissue factor and the second reagent contains phospholipids.

An eighth embodiment of the present invention provides a blood specimen analyzer. This analyzer comprises a measurement sample preparing section for preparing a measurement sample, an optical information acquiring section for irradiating the prepared measurement sample with light and acquiring optical information on the light amount from the measurement sample, and a control section, wherein the control section dilutes an activated partial thromboplastin time measuring reagent containing a coagulation factor XII-activating agent and phospholipids to a predetermined ratio with a diluent, and controls the measurement sample preparing section so as to prepare a measurement sample from the diluted reagent, a blood specimen obtained from a subject to whom a substance having a coagulation factor VIII-substituting activity is administered, and a calcium ion-containing aqueous solution, acquires at least one parameter on differentiation of coagulation waveform based on the optical information, and outputs reference information on coagulability of the blood specimen based on the value of the acquired parameter.

A ninth embodiment of the present invention provides a blood specimen analyzer. This analyzer comprises a measurement sample preparing section for preparing a measurement sample, an optical information acquiring section for irradiating the prepared measurement sample with light and acquiring optical information on the light amount from the measurement sample, and a control section, wherein the control section controls the measurement sample preparing section so as to prepare a measurement sample from a blood specimen obtained from a subject to whom a substance having a coagulation factor VIII-substituting activity is administered, a coagulation factor XII-activating agent, phospholipids, tissue factor, and a calcium ion-containing aqueous solution, and outputs reference information on coagulability of the blood specimen, based on the optical information.

A tenth embodiment of the present invention provides an apparatus for evaluating coagulability of a blood specimen, comprising a computer including a processor and a memory under control of the processor. In the above memory, a computer program for executing the computer the steps of acquiring optical information on the light amount from the measurement sample prepared from a blood specimen obtained from a subject to whom a substance having a coagulation factor VIII-substituting activity is administered, a coagulation factor XII-activating agent, phospholipids, and a calcium ion-containing aqueous solution, acquiring at least one parameter on differentiation of coagulation waveform based on the optical information, and outputting reference information on coagulability of the blood specimen based on the value of the acquired parameter is recorded.

An eleventh embodiment of the present invention provides a computer program for evaluating coagulability of a blood specimen, which is recorded on a computer readable medium. This computer program is characterized by executing the computer the steps of acquiring optical information on the light amount from the measurement sample prepared from a blood specimen obtained from a subject to whom a substance having a coagulation factor VIII-substituting activity is administered, a coagulation factor XII-activating agent, phospholipids, and a calcium ion-containing aqueous solution, acquiring at least one parameter on differentiation of coagulation waveform based on the optical information, and outputting reference information on coagulability of the blood specimen based on the value of the acquired parameter is recorded.

A twelfth embodiment of the present invention provides a reagent kit for evaluating coagulability of a blood specimen obtained from a subject to whom a substance having a coagulation factor VIII-substituting activity is administered, comprising a first reagent and a second reagent, wherein the first reagent contains a coagulation factor XII-activating agent and phospholipids and the second reagent contains tissue factor and calcium ions.

Advantageous Effects of Invention

According to the present invention, it is possible to appropriately evaluate coagulability of a blood specimen obtained from a subject to whom a substance having a factor VIII-substituting activity is administered.

BRIEF DESCRIPTION OF DRAWINGS

FIG. 1 is an example of a coagulation waveform of normal plasma and graphs of the first derivative and second derivative thereof.

FIG. 2 is a diagram showing an example of a reagent according to the present embodiment.

FIG. 3A is a view showing an example of a reagent kit according to the present embodiment.

FIG. 3B is a view showing an example of a reagent kit according to the present embodiment.

FIG. 4 is a perspective view showing the configuration of an appearance of a blood specimen analyzer.

FIG. 5 is a plan view of an inside of a measurement unit of the blood specimen analyzer when viewed from above.

FIG. 6 is a diagram showing the configuration of the measurement unit of the blood specimen analyzer.

FIG. 7 is a diagram showing the configuration of a lamp unit provided in the measurement device.

FIG. 8A is a diagram showing the configuration of a detecting section provided in the measurement device.

FIG. 8B is a diagram showing the configuration of a detecting section provided in the measurement device.

FIG. 8C is a diagram showing the configuration of a detecting section provided in the measurement device.

FIG. 8D is a diagram showing the configuration of a detecting section provided in the measurement device.

FIG. 9 is a diagram showing the functional configuration of a control device of the blood specimen analyzer.

FIG. 10 is a diagram showing the hardware configuration of a control device of the blood specimen analyzer.

FIG. 11 is a flowchart showing measurement processing of a blood specimen by the blood specimen analyzer.

FIG. 12 is a flowchart showing analysis processing of a blood specimen by the blood specimen analyzer.

FIG. 13 is a view showing an example of a screen for displaying an analysis result by the blood specimen analyzer.

FIG. 14A is graphs of coagulation times respectively obtained from blood specimens containing ACE910 and blood specimens containing rhFVIII.

FIG. 14B is graphs of FVIII activity values converted from coagulation times of blood specimens containing ACE910.

FIG. 15A is graphs of |Min 1| respectively obtained from blood specimens containing ACE910 and blood specimens containing rhFVIII.

FIG. 15B is graphs of FVIII activity values converted from |Min 1| of blood specimens containing ACE910.

FIG. 16A is graphs of |Min 2| respectively obtained from blood specimens containing ACE910 and blood specimens containing rhFVIII.

FIG. 16B is graphs of FVIII activity values converted from |Min 2| of blood specimens containing ACE910.

FIG. 17A is graphs of Max 2 respectively obtained from blood specimens containing ACE910 and blood specimens containing rhFVIII.

FIG. 17B is graphs of FVIII activity values converted from Max 2 of blood specimens containing ACE910.

FIG. 18A is graphs of FVIII activity values converted from coagulation times of blood specimens containing ACE910, obtained with a 3-fold diluted APTT measuring reagent.

FIG. 18B is graphs of FVIII activity values converted from |Min 1| of blood specimens containing ACE910, obtained with a 3-fold diluted APTT measuring reagent.

FIG. 18C is graphs of FVIII activity values converted from |Min 2| of blood specimens containing ACE910, obtained with a 3-fold diluted APTT measuring reagent.

FIG. 18D is graphs of FVIII activity values converted from Max 2 of blood specimens containing ACE910, obtained with a 3-fold diluted APTT measuring reagent.

FIG. 19A is graphs of |Min 1| obtained from blood specimens containing ACE910 and rhFVIII.

FIG. 19B is graphs of FVIII activity values converted from |Min 1| of blood specimens containing ACE910 and rhFVIII.

FIG. 20A is graphs of |Min 2| obtained from blood specimens containing ACE910 and rhFVIII.

FIG. 20B is graphs of FVIII activity values converted from |Min 2| of blood specimens containing ACE910 and rhFVIII.

FIG. 21A is graphs of Max 2 obtained from blood specimens containing ACE910 and rhFVIII.

FIG. 21B is graphs of FVIII activity values converted from Max 2 of blood specimens containing ACE910 and rhFVIII.

FIG. 22A is graphs showing |Min 1| obtained from human FVIII-deficient plasma (Lot No. 899-3062) respectively containing ACE910 and rhFVIII, using reagents 1 to 3 for blood coagulation analysis.

FIG. 22B is graphs showing |Min 2| obtained from human FVIII-deficient plasma (Lot No. 899-3062) respectively containing ACE910 and rhFVIII, using reagents 1 to 3 for blood coagulation analysis.

FIG. 22C is graphs showing FVIII activity values converted from |Min 1| obtained from human FVIII-deficient plasma (Lot No. 899-3062) containing ACE910, using reagents 1 to 3 for blood coagulation analysis.

FIG. 22D is graphs showing FVIII activity values converted from |Min 2| obtained from human FVIII-deficient plasma (Lot No. 899-3062) containing ACE910, using reagents 1 to 3 for blood coagulation analysis.

FIG. 23A is graphs showing |Min 1| obtained from human FVIII-deficient plasma (Lot No. 895-2757) respectively containing ACE910 and rhFVIII, using reagents 1 to 3 for blood coagulation analysis.

FIG. 23B is graphs showing |Min 2| obtained from human FVIII-deficient plasma (Lot No. 895-2757) respectively containing ACE910 and rhFVIII, using reagents 1 to 3 for blood coagulation analysis.

FIG. 23C is graphs showing FVIII activity values converted from |Min 1| obtained from human FVIII-deficient plasma (Lot No. 895-2757) containing ACE910, using reagents 1 to 3 for blood coagulation analysis.

FIG. 23D is graphs showing FVIII activity values converted from |Min 2| obtained from human FVIII-deficient plasma (Lot No. 895-2757) containing ACE910, using reagents 1 to 3 for blood coagulation analysis.

FIG. 24A is graphs showing |Min 1| obtained from human FVIII-deficient plasma (Lot No. 899-2847) respectively containing ACE910 and rhFVIII, using reagents 1 to 3 for blood coagulation analysis.

FIG. 24B is graphs showing |Min 2| obtained from human FVIII-deficient plasma (Lot No. 899-2847) respectively containing ACE910 and rhFVIII, using reagents 1 to 3 for blood coagulation analysis.

FIG. 24C is graphs showing FVIII activity values converted from |Min 1| obtained from human FVIII-deficient plasma (Lot No. 899-2847) containing ACE910, using reagents 1 to 3 for blood coagulation analysis.

FIG. 24D is graphs showing FVIII activity values converted from |Min 2| obtained from human FVIII-deficient plasma (Lot No. 899-2847) containing ACE910, using reagents 1 to 3 for blood coagulation analysis.

FIG. 25A is a graph showing coagulation time obtained from human FVIII-deficient plasma (Lot No. 899-3394) containing ACE910, using reagent 4 for blood coagulation analysis.

FIG. 25B is a graph showing |Min 1| obtained from human FVIII-deficient plasma (Lot No. 899-3394) containing ACE910, using reagent 4 for blood coagulation analysis.

FIG. 25C is a graph showing |Min 2| obtained from human FVIII-deficient plasma (Lot No. 899-3394) containing ACE910, using reagent 4 for blood coagulation analysis.

FIG. 26A is graphs showing coagulation time obtained from human FVIII-deficient plasma (Lot No. 899-3062) containing ACE910, using reagents 6 to 9 for blood coagulation analysis.

FIG. 26B is a graph showing coagulation time obtained from human FVIII-deficient plasma (Lot No. 899-3062) containing ACE910, using reagent 10 for blood coagulation analysis.

FIG. 26C is graphs showing coagulation time obtained from human FVIII-deficient plasma (Lot No. 899-3062) containing ACE910, using reagents 11 to 13 for blood coagulation analysis.

FIG. 26D is graphs showing |Min 1| obtained from human FVIII-deficient plasma (Lot No. 899-3062) containing ACE910, using reagents 6 to 9 for blood coagulation analysis.

FIG. 26E is graphs showing |Min 1| obtained from human FVIII-deficient plasma (Lot No. 899-3062) containing ACE910, using reagents 10 to 13 for blood coagulation analysis.

FIG. 26F is graphs showing |Min 1| obtained from human FVIII-deficient plasma (Lot No. 899-3062) containing ACE910, using reagents 14 and 15 for blood coagulation analysis.

FIG. 26G is graphs showing |Min 2| obtained from human FVIII-deficient plasma (Lot No. 899-3062) containing ACE910, using reagents 6 to 9 for blood coagulation analysis.

FIG. 26H is graphs showing |Min 2| obtained from human FVIII-deficient plasma (Lot No. 899-3062) containing ACE910, using reagents 10 to 13 for blood coagulation analysis.

FIG. 26I is graphs showing |Min 2| obtained from human FVIII-deficient plasma (Lot No. 899-3062) containing ACE910, using reagents 14 and 15 for blood coagulation analysis.

FIG. 27A is a graph showing coagulation time obtained from human FVIII-deficient plasma (Lot No. 899-3394) containing ACE910, using reagent 5 for blood coagulation analysis.

FIG. 27B is graphs showing coagulation time obtained from human FVIII-deficient plasma (Lot No. 899-3394) containing ACE910, using reagents 6 to 9 for blood coagulation analysis.

FIG. 27C is graphs showing coagulation time obtained from human FVIII-deficient plasma (Lot No. 899-3394) containing ACE910, using reagents 12 and 13 for blood coagulation analysis.

FIG. 27D is a graph showing |Min 1| obtained from human FVIII-deficient plasma (Lot No. 899-3394) containing ACE910, using reagent 5 for blood coagulation analysis.

FIG. 27E is graphs showing |Min 1| obtained from human FVIII-deficient plasma (Lot No. 899-3394) containing ACE910, using reagents 6 to 9 for blood coagulation analysis.

FIG. 27F is graphs showing |Min 1| obtained from human FVIII-deficient plasma (Lot No. 899-3394) containing ACE910, using reagents 10 to 13 for blood coagulation analysis.

FIG. 27G is a graph showing |Min 2| obtained from human FVIII-deficient plasma (Lot No. 899-3394) containing ACE910, using reagent 5 for blood coagulation analysis.

FIG. 27H is graphs showing |Min 2| obtained from human FVIII-deficient plasma (Lot No. 899-3394) containing ACE910, using reagents 6 to 9 for blood coagulation analysis.

FIG. 27I is graphs showing |Min 2| obtained from human FVIII-deficient plasma (Lot No. 899-3394) containing ACE910, using reagents 11 to 13 for blood coagulation analysis.

FIG. 28 is a graph showing FVIII activity values converted from |Min 1| obtained from human FVIII-deficient plasma (Lot No. 899-3394) containing ACE910, using reagent 4 for blood coagulation analysis.

FIG. 29 is graphs showing FVIII activity values converted from |Min 1| obtained from human FVIII-deficient plasma (Lot No. 899-3062) containing ACE910, using reagent 6, 11, 12 or 15 for blood coagulation analysis.

FIG. 30A is a graph showing |Min 1| obtained from human FVIII-deficient plasma (Lot No. 899-3062) containing ACE910 added with rhFVIII at a concentration of 1 U/dL, using reagent 3 for blood coagulation analysis.

FIG. 30B is a graph showing |Min 2| obtained from human FVIII-deficient plasma (Lot No. 899-3062) containing ACE910 added with rhFVIII at a concentration of 1 U/dL, using reagent 3 for blood coagulation analysis.

FIG. 30C is a graph showing |Min 1| obtained from human FVIII-deficient plasma (Lot No. 899-3062) containing ACE910 added with rhFVIII at a concentration of 5 U/dL, using reagent 3 for blood coagulation analysis.

FIG. 30D is a graph showing |Min 2| obtained from human FVIII-deficient plasma (Lot No. 899-3062) containing ACE910 added with rhFVIII at a concentration of 5 U/dL, using reagent 3 for blood coagulation analysis.

FIG. 30E is a graph showing |Min 2| obtained from human FVIII-deficient plasma (Lot No. 899-3062) containing ACE910 added with rhFVIII at a concentration of 20 U/dL, using reagent 3 for blood coagulation analysis.

FIG. 31A is a graph showing |Min 1| obtained from human FVIII-deficient plasma (Lot No. 899-3394) containing ACE910 added with rhFVIII at a concentration of 1 U/dL, using reagent 12 for blood coagulation analysis.

FIG. 31B is a graph showing |Min 2| obtained from human FVIII-deficient plasma (Lot No. 899-3394) containing ACE910 added with rhFVIII at a concentration of 1 U/dL, using reagent 12 for blood coagulation analysis.

FIG. 31C is a graph showing |Min 1| obtained from human FVIII-deficient plasma (Lot No. 899-3394) containing ACE910 added with rhFVIII at a concentration of 5 U/dL, using reagent 12 for blood coagulation analysis.

FIG. 31D is a graph showing |Min 2| obtained from human FVIII-deficient plasma (Lot No. 899-3394) containing ACE910 added with rhFVIII at a concentration of 5 U/dL, using reagent 12 for blood coagulation analysis.

FIG. 31E is a graph showing |Min 2| obtained from human FVIII-deficient plasma (Lot No. 899-3394) containing ACE910 added with rhFVIII at a concentration of 20 U/dL, using reagent 12 for blood coagulation analysis.

FIG. 31F is a graph showing |Min 1| obtained from human FVIII-deficient plasma (Lot No. 899-3394) containing ACE910 added with rhFVIII at a concentration of 50 U/dL, using reagent 12 for blood coagulation analysis.

FIG. 31G is a graph showing |Min 2| obtained from human FVIII-deficient plasma (Lot No. 899-3394) containing ACE910 added with rhFVIII at a concentration of 50 U/dL, using reagent 12 for blood coagulation analysis.

FIG. 31H is a graph showing |Min 1| obtained from human FVIII-deficient plasma (Lot No. 899-3394) containing ACE910 added with rhFVIII at a concentration of 100 U/dL, using reagent 12 for blood coagulation analysis.

FIG. 31I is a graph showing |Min 2| obtained from human FVIII-deficient plasma (Lot No. 899-3394) containing ACE910 added with rhFVIII at a concentration of 100 U/dL, using reagent 12 for blood coagulation analysis.

FIG. 31J is a graph showing |Min 1| obtained from human FVIII-deficient plasma (Lot No. 899-3394) containing ACE910 added with rhFVIII at a concentration of 200 U/dL, using reagent 12 for blood coagulation analysis.

FIG. 31K is a graph showing |Min 2| obtained from human FVIII-deficient plasma (Lot No. 899-3394) containing ACE910 added with rhFVIII at a concentration of 200 U/dL, using reagent 12 for blood coagulation analysis.

FIG. 32A is a graph showing coagulation time obtained from human FVIII-deficient plasma containing ACE910 added with rhFVIII at a concentration of 0 U/dL (not added), 100 U/dL, or 200 U/dL, using reagent 16 for blood coagulation analysis.

FIG. 32B is a graph showing |Min 1| obtained from human FVIII-deficient plasma containing ACE910 added with rhFVIII at a concentration of 0 U/dL (not added), 100 U/dL, or 200 U/dL, using reagent 16 for blood coagulation analysis.

FIG. 32C is a graph showing |Min 2| obtained from human FVIII-deficient plasma containing ACE910 added with rhFVIII at a concentration of 0 U/dL (not added), 100 U/dL, or 200 U/dL, using reagent 16 for blood coagulation analysis.

FIG. 33A is graphs showing coagulation time obtained from human FVIII-deficient plasma containing ACE910, using reagent kits 17 to 21 for blood coagulation analysis.

FIG. 33B is graphs showing coagulation time obtained from human FVIII-deficient plasma containing ACE910, using reagent kits 22 to 24 for blood coagulation analysis.

FIG. 33C is graphs showing coagulation time obtained from human FVIII-deficient plasma containing ACE910, using reagent kits 25 and 26 for blood coagulation analysis.

FIG. 33D is graphs showing coagulation time obtained from human FVIII-deficient plasma containing ACE910, using reagent kits 27 to 31 for blood coagulation analysis.

FIG. 33E is graphs showing coagulation time obtained from human FVIII-deficient plasma containing ACE910, using reagent kits 32 to 34 for blood coagulation analysis.

FIG. 34A is graphs showing |Min 1| obtained from human FVIII-deficient plasma containing ACE910, using reagent kits 17 to 21 for blood coagulation analysis.

FIG. 34B is graphs showing |Min 1| obtained from human FVIII-deficient plasma containing ACE910, using reagent kits 22 to 24 for blood coagulation analysis.

FIG. 34C is graphs showing |Min 1| obtained from human FVIII-deficient plasma containing ACE910, using reagent kits 25 and 26 for blood coagulation analysis.

FIG. 34D is graphs showing |Min 1| obtained from human FVIII-deficient plasma containing ACE910, using reagent kits 27 to 31 for blood coagulation analysis.

FIG. 34E is graphs showing |Min 1| obtained from human FVIII-deficient plasma containing ACE910, using reagent kits 32 to 34 for blood coagulation analysis.

FIG. 35A is graphs showing |Min 2| obtained from human FVIII-deficient plasma containing ACE910, using reagent kits 17 to 21 for blood coagulation analysis.

FIG. 35B is graphs showing |Min 2| obtained from human FVIII-deficient plasma containing ACE910, using reagent kits 22 to 24 for blood coagulation analysis.

FIG. 35C is graphs showing |Min 2| obtained from human FVIII-deficient plasma containing ACE910, using reagent kits 25 and 26 for blood coagulation analysis.

FIG. 35D is graphs showing |Min 2| obtained from human FVIII-deficient plasma containing ACE910, using reagent kits 27 to 31 for blood coagulation analysis.

FIG. 35E is graphs showing |Min 2| obtained from human FVIII-deficient plasma containing ACE910, using reagent kits 32 to 34 for blood coagulation analysis.

FIG. 36A is graphs showing FVIII activity values converted from |Min 1| obtained from human FVIII-deficient plasma containing ACE910, using reagent kits 19, 20, 23 and 24 for blood coagulation analysis.

FIG. 36B is graphs showing FVIII activity values converted from |Min 1| obtained from human FVIII-deficient plasma containing ACE910, using reagent kits 28, 30, 32, 33 and 34 for blood coagulation analysis.

FIG. 37A is graphs showing FVIII activity values converted from |Min 2| obtained from human FVIII-deficient plasma containing ACE910, using reagent kits 22 and 23 for blood coagulation analysis.

FIG. 37B is graphs showing FVIII activity values converted from |Min 2| obtained from human FVIII-deficient plasma containing ACE910, using reagent kit 34 for blood coagulation analysis.

FIG. 38A is a graph showing |Min 1| obtained from human FVIII-deficient plasma containing ACE910 added with APCC that is a bypass preparation at a concentration of 0.5 U/mL, using reagent kit 20 for blood coagulation analysis.

FIG. 38B is a graph showing |Min 1| obtained from human FVIII-deficient plasma containing ACE910 added with APCC at a concentration of 1 U/mL, using reagent kit 20 for blood coagulation analysis.

FIG. 38C is a graph showing |Min 1| obtained from human FVIII-deficient plasma containing ACE910 added with FVIIa that is a bypass preparation at a concentration of 0.25 µg/mL, using reagent kit 20 for blood coagulation analysis.

FIG. 38D is a graph showing |Min 1| obtained from human FVIII-deficient plasma containing ACE910 added with FVIIa at a concentration of 1.25 µg/mL, using reagent kit 20 for blood coagulation analysis.

FIG. 39A is a graph showing |Min 1| obtained from human FVIII-deficient plasma containing ACE910 added with APCC at a concentration of 0.5 U/mL, using reagent kit 21 for blood coagulation analysis.

FIG. 39B is a graph showing |Min 1| obtained from human FVIII-deficient plasma containing ACE910 added with APCC at a concentration of 1 U/mL, using reagent kit 21 for blood coagulation analysis.

FIG. 39C is a graph showing |Min 1| obtained from human FVIII-deficient plasma containing ACE910 added with FVIIa at a concentration of 0.25 µg/mL, using reagent kit 21 for blood coagulation analysis.

FIG. 39D is a graph showing |Min 1| obtained from human FVIII-deficient plasma containing ACE910 added with FVIIa at a concentration of 1.25 µg/mL, using reagent kit 21 for blood coagulation analysis.

FIG. 40A is a graph showing |Min 1| obtained from human FVIII-deficient plasma containing ACE910 added with APCC at a concentration of 0.5 U/mL, using reagent kit 28 for blood coagulation analysis.

FIG. 40B is a graph showing |Min 1| obtained from human FVIII-deficient plasma containing ACE910 added with APCC at a concentration of 1 U/mL, using reagent kit 28 for blood coagulation analysis.

FIG. 40C is a graph showing |Min 1| obtained from human FVIII-deficient plasma containing ACE910 added with FVIIa at a concentration of 0.25 µg/mL, using reagent kit 28 for blood coagulation analysis.

FIG. 40D is a graph showing |Min 1| obtained from human FVIII-deficient plasma containing ACE910 added with FVIIa at a concentration of 1.25 µg/mL, using reagent kit 28 for blood coagulation analysis.

FIG. 41A is a graph showing |Min 1| obtained from human FVIII-deficient plasma containing ACE910 added with APCC at a concentration of 0.5 U/mL, using reagent kit 30 for blood coagulation analysis.

FIG. 41B is a graph showing |Min 1| obtained from human FVIII-deficient plasma containing ACE910 added with APCC at a concentration of 1 U/mL, using reagent kit 30 for blood coagulation analysis.

FIG. 41C is a graph showing |Min 1| obtained from human FVIII-deficient plasma containing ACE910 added with FVIIa at a concentration of 0.25 µg/mL, using reagent kit 30 for blood coagulation analysis.

FIG. 41D is a graph showing |Min 1| obtained from human FVIII-deficient plasma containing ACE910 added with FVIIa at a concentration of 1.25 µg/mL, using reagent kit 30 for blood coagulation analysis.

FIG. 42A is a graph showing |Min 1| obtained from human FVIII-deficient plasma containing ACE910 added with APCC at a concentration of 0.5 U/mL, using reagent kit 33 for blood coagulation analysis.

FIG. 42B is a graph showing |Min 1| obtained from human FVIII-deficient plasma containing ACE910 added with APCC at a concentration of 1 U/mL, using reagent kit 33 for blood coagulation analysis.

FIG. 42C is a graph showing |Min 1| obtained from human FVIII-deficient plasma containing ACE910 added with FVIIa at a concentration of 0.25 µg/mL, using reagent kit 33 for blood coagulation analysis.

FIG. 42D is a graph showing |Min 1| obtained from human FVIII-deficient plasma containing ACE910 added with FVIIa at a concentration of 1.25 µg/mL, using reagent kit 33 for blood coagulation analysis.

FIG. 43A is a graph showing |Min 1| obtained from human FVIII-deficient plasma containing ACE910 added with APCC at a concentration of 0.5 U/mL, using reagent kit 35 for blood coagulation analysis.

FIG. 43B is a graph showing |Min 1| obtained from human FVIII-deficient plasma containing ACE910 added with APCC at a concentration of 1 U/mL, using reagent kit 35 for blood coagulation analysis.

FIG. 43C is a graph showing |Min 1| obtained from human FVIII-deficient plasma containing ACE910 added with FVIIa at a concentration of 0.25 µg/mL, using reagent kit 35 for blood coagulation analysis.

FIG. 43D is a graph showing |Min 1| obtained from human FVIII-deficient plasma containing ACE910 added with FVIIa at a concentration of 1.25 µg/mL, using reagent kit 35 for blood coagulation analysis.

FIG. 44A is a graph showing |Min 1| obtained from human FVIII-deficient plasma containing ACE910 added with APCC at a concentration of 0.5 U/mL, using reagent kit 36 for blood coagulation analysis.

FIG. 44B is a graph showing |Min 1| obtained from human FVIII-deficient plasma containing ACE910 added with APCC at a concentration of 1 U/mL, using reagent kit 36 for blood coagulation analysis.

FIG. 44C is a graph showing |Min 1| obtained from human FVIII-deficient plasma containing ACE910 added with FVIIa at a concentration of 0.25 µg/mL, using reagent kit 36 for blood coagulation analysis.

FIG. 44D is a graph showing |Min 1| obtained from human FVIII-deficient plasma containing ACE910 added with FVIIa at a concentration of 1.25 µg/mL, using reagent kit 36 for blood coagulation analysis.

DESCRIPTION OF EMBODIMENTS

[1. Method for Evaluating Coagulability of Blood Specimen]

In the method for evaluating coagulability of a blood specimen according to the first embodiment (hereinafter, also referred to as "the method according to the first embodiment"), first, a measurement sample is prepared from a substance having a coagulation factor VIII-substituting activity (FVIII), a coagulation factor XII-activating agent, phospholipids, and a calcium ion-containing aqueous solution. In the method according to the first embodiment, the coagulability of a blood specimen containing a substance having a FVIII-substituting activity is evaluated, based on the measurement principle of activated partial thromboplastin time (APTT).

In the present embodiment, the blood specimen is not particularly limited as long as it is derived from blood containing a substance having a FVIII-substituting activity. Examples of the type of specimen include whole blood and plasma. Among them, plasma is preferable, and platelet-removed plasma is particularly preferable. The platelets can be removed by a known method such as centrifugation or filter separation. In the present embodiment, a mixture obtained by adding a substance having a FVIII-substituting activity to commercially available plasma may be used as a blood specimen. Examples of the commercially available plasma include coagulation factor-deficient plasma and the like. A coagulation factor preparation such as FVIII may be added to the blood specimen as necessary.

In a preferred embodiment, blood collected from a subject to whom a substance having a FVIII-substituting activity is administered or blood plasma prepared from the blood is used as a blood specimen containing a substance having a FVIII-substituting activity. Examples of the subject include patients with hemorrhagic disease caused by defect or dysfunction of coagulation factor. Examples of the hemorrhagic disease include hemophilia A, hemophilia B, acquired hemophilia, von Willebrand disease, and the like. More preferably, the subject is a patient with hemorrhagic disease in which the activity of either or both of FVIII and FVIIIa is decreased or deficient. The activity value of FVIII in the patient is, for example, less than 40%, 30% or 20%, preferably less than 10%, 9%, 8%, 7% or 6%, more preferably less than 5%, 4%, 3% or 2%, and particularly preferably less than 1%, based on the FVIII activity value of a healthy subject as 100%. The method itself for measuring the activity value of FVIII in a blood specimen is known in the art, and examples thereof include a synthetic substrate method and the like.

In the present embodiment, the substance having a FVIII-substituting activity is not particularly limited as long as it is a substance having cofactor activity similar to FVIIIa in blood. However, the substance having a FVIII-substituting activity does not include FVIII and FVIIIa. The substance having a FVIII-substituting activity is preferably a substance capable of specifically binding to both FIX or FIXa and FX and capable of promoting activation of FX by FIXa (that is, production of FXa). Examples of the substance include bispecific antibodies that specifically bind to both FIX or FIXa and FX. The bispecific antibodies themselves are known in the art, and disclosed, for example, in WO 2005/035756, WO 2006/109592, and WO 2012/067176. More specifically, examples of the substance having a FVIII-substituting activity include ACE910 (Q499-z121/J327-z119/L404-k) (Emicizumab) which is an anti-FIXa/FX bispecific antibody described in Patent Literature (WO 2012/067176).

In the present embodiment, the origin of the bispecific antibody is not particularly limited, and may be an antibody derived from any mammal such as human, mouse, rat, hamster, rabbit, goat, horse or camel, and is preferably a human antibody. Incidentally, the method itself for acquiring a human antibody is known in the art, and for example, a method utilizing a non-human transgenic animal having a human antibody gene and the like are known. In the present embodiment, fragments of bispecific antibodies and derivatives thereof may be used, and examples thereof include Fab fragments, F(ab')2 fragments, diabodies, linear antibodies, single chain antibodies, and the like. In addition, the bispecific antibody may be a genetically modified antibody such as a chimeric antibody or a humanized antibody.

In the present embodiment, the coagulation factor XII (FXII)-activating agent is not particularly limited as long as it is a known substance that is known to activate FXII to promote the production of activated factor XII (FXIIa) and promote blood coagulation in vitro. Examples of the activating agent include substances having a negative charge. Examples of the substance include ellagic acid, kaolin, celite, silica, and the like. Among them, ellagic acid is preferred. As ellagic acid, ellagic acid in the state of forming a metal ion with a chelate may be added. In the present embodiment, the FXII-activating agent is preferably in the form of a liquid in which the FXII-activating agent is dissolved in a suitable solvent.

In the method according to the first embodiment, in order to evaluate coagulability of a blood specimen containing a substance having a FVIII-substituting activity with appropriate sensitivity, the final concentration of the FXII-activating agent in the measurement sample is set at usually 1 $\mu$M or more and 22 $\mu$M or less, and preferably 2.9 $\mu$M or more and 14 $\mu$M or less.

In the present embodiment, examples of the phospholipid include phosphatidylethanolamine (PE), phosphatidylcholine (PC) and phosphatidylserine (PS). In the present embodiment, one, preferably two, more preferably all kinds of phospholipids selected from PE, PC and PS can be added. The phospholipid may be a naturally occurring phospholipid or a synthetic phospholipid. Among them, synthetic phospholipids or naturally occurring phospholipids purified to have a purity of 99% or more are preferred. The fatty acid side chains of PE, PC and PS are not particularly limited, and examples thereof include palmitic acid, oleic acid, stearic acid, and the like. Among them, oleic acid is preferable. In the present embodiment, the phospholipid is preferably in the form of a liquid in which the phospholipid is dissolved in a suitable solvent.

In the method according to the first embodiment, in order to evaluate coagulability of a blood specimen containing a substance having a FVIII-substituting activity with appropriate sensitivity, the final concentration of the phospholipids in the measurement sample is set at usually 1.4 $\mu$M or more and 33 $\mu$M or less, and preferably 4.3 $\mu$M or more and 22 $\mu$M or less. When PE, PC and PS are contained as phospholipids, the sum of the concentrations of PE, PC and PS in the measurement sample may be within the above range.

In the method according to the first embodiment, when the final concentration of the FXII-activating agent in the measurement sample is set at 1 $\mu$M or more and 2.9 $\mu$M or less, the upper limit of the final concentration of the phospholipids in the measurement sample is set within the range from more than 33 $\mu$M and less than 43 $\mu$M. Accordingly, in the present embodiment, in order to evaluate coagulability of a blood specimen containing a substance having a FVIII-substituting activity with appropriate sensitivity, when the final concentration of the FXII-activating agent in the measurement sample is set at 1 $\mu$M or more and 2.9 $\mu$M or less, the final concentration of the phospholipids in the measurement sample may be usually set at 1.4 $\mu$M or more and 43 $\mu$M or less.

In preparing the measurement sample, the order of mixing the blood specimen, the FXII-activating agent, and the phospholipids is not particularly limited. For example, the blood specimen and the FXII-activating agent are mixed, and then the phospholipids may be mixed therein. Alternatively, the blood specimen and the phospholipids are mixed, and then the FXII-activating agent may be mixed therein. Or, the FXII-activating agent and the phospholipids are mixed, and then the blood specimen may be mixed therein. Alternatively, the blood specimen, the FXII-activating agent, and the phospholipids may be substantially simultaneously mixed.

Since the method according to the first embodiment is based on the principle of APTT measurement, in the present embodiment, a commercially available APTT measuring reagent containing a FXII-activating agent and phospholipids may be used. In this case, an APTT measuring reagent may be used so that the respective final concentrations of the FXII-activating agent and the phospholipids in the measurement sample fall within the above range. However, a general commercially available APTT measuring reagent is not intended to be used with the respective final concentrations of the FXII-activating agent and the phospholipids in the measurement sample within the above range. Therefore, in the present embodiment, a commercially available APTT measuring reagent may be diluted and used as necessary. Examples of the diluent include physiological saline, buffer with a pH of 6 to 8, water, and the like. Also, commercially available buffers may be used, and examples thereof include Owren's Veronal buffer (Sysmex Corporation), TC buffer (Sysmex Corporation), imidazole buffer (HYPHEN BioMed), and the like.

In the present embodiment, it is preferable to mix a blood specimen, a FXII-activating agent and phospholipids, incubate them under predetermined conditions, and then add the calcium-containing aqueous solution described later. Such a predetermined condition may be any known condition as long as it accelerates the reaction between the coagulation factor and the substance having a FVIII-substituting activity in the blood specimen, with the FXII-activating agent and the phospholipid, and examples thereof include a condition of incubating at a temperature of 35° C. or more and 40° C. or less for a time of 2 minutes or more and 5 minutes or less.

In the present embodiment, a calcium ion-containing aqueous solution is used as a reagent for initiating blood coagulation. The calcium ion-containing aqueous solution is not particularly limited as long as it can provide calcium ions necessary for blood coagulation in the measurement sample. As the calcium ion-containing aqueous solution, an aqueous solution of a calcium salt is preferable, and examples thereof include an aqueous calcium chloride solution and the like. The calcium ion content in the measurement sample may be an amount sufficient to cause coagulation, and for example, it is usually 2 mM or more and 20 mM or less, and preferably 4 mM or more and 10 mM or less, in terms of calcium chloride concentration. Incidentally, the calcium ion-containing aqueous solution is also referred to as "calcium solution" hereinafter.

In the present embodiment, a blood specimen, a FXII-activating agent and phospholipids are mixed, and then a calcium solution is added to obtain a measurement sample. Then, using the time when the calcium solution is added as the measurement starting point, optical information on the light amount described later is acquired from the measurement sample.

In the present embodiment, the preparation of the measurement sample may be performed by a manual method or may be carried out by a fully automatic measurement device. Examples of the device include CS-5100 (Sysmex Corporation), CS-2400 (Sysmex Corporation), CS-2000i (Sysmex Corporation), and the like.

In the method according to the first embodiment, the measurement sample obtained as described above is irradiated with light to acquire optical information on the light amount from the measurement sample. In the present embodiment, the light to be irradiated to the measurement sample may be light which is usually used for measuring coagulation time, and examples thereof include light having a wavelength of around 660 nm, and preferably, light having a wavelength of 660 nm. A light source is not particularly limited, and examples thereof include a light emitting diode, a halogen lamp, and the like.

By irradiating the measurement sample with light from the above light source, scattered light and transmitted light are generated from the measurement sample. In the present embodiment, examples of the optical information on the light amount include the amount of scattered light or the amount of transmitted light, and scattered light intensity, transmittance, absorbance and the like are preferable.

In the present embodiment, the measurement conditions are not particularly limited, but irradiation of light and acquisition of optical information on the light amount are continuously or intermittently from the start of measurement (at the time of adding a calcium solution) to the completion of the coagulation reaction (formation of fibrin clot). In this way, based on the optical information on the light amount (e.g., scattered light intensity, transmittance or absorbance) continuously or intermittently measured over the whole process of coagulation, it is possible to acquire the parameter on differentiation of coagulation waveform described later at any time point or time in the coagulation process. Incidentally, the irradiation of light and the acquisition of optical information on the light amount may be performed by a fully automatic measurement device. Examples of the devices include CS-5100 (Sysmex Corporation), CS-2400 (Sysmex Corporation), and CS-2000i (Sysmex Corporation) of a fully automated blood coagulation measuring apparatus, and the like.

In the present embodiment, the coagulation waveform is a waveform representing a temporal change in the optical information on the light amount (e.g., amount of scattered light, transmittance or absorbance). With reference to FIG. 1, coagulation waveform and its waveform analysis will be described. In the coagulation waveform (upper graph) in FIG. 1, point a is a measurement starting point, point b is a fibrin precipitation (start of coagulation) point, and a-b shows coagulation time. Point c is a middle point of coagulation, point d is an end point of coagulation, and point e is an end point of measurement. When the coagulation waveform is differentiated (primarily differentiated), the coagulation rate is calculated (see the middle graph in FIG. 1). The point c of the coagulation waveform corresponds to the maximum value of the first derivative. When the coagulation rate is differentiated (secondarily differentiated), the coagulation acceleration is calculated (see the lower graph in FIG. 1). In the method according to the present embodiment, acquisition of coagulation time and coagulation waveform is arbitrary.

In the method according to the first embodiment, at least one parameter on differentiation of coagulation waveform is acquired based on the acquired optical information. The parameter on differentiation of coagulation waveform is not particularly limited as long as it is a value indicating at least one of coagulation rate, coagulation acceleration, and coagulation deceleration obtained on the basis of the acquired optical information. The value indicating the coagulation rate corresponds to a value that can be obtained from the first derivative of the coagulation waveform, and the value indicating the coagulation acceleration and the value indicating the coagulation deceleration correspond to values that can be obtained from the second derivative of the coagulation waveform.

Examples of the parameter on differentiation of coagulation waveform include |Min 1|, |Min 2|, Max 2, AUC, and Slope. |Min 1| is the absolute value of the minimum value of the first derivative of the coagulation waveform and represents the maximum coagulation rate. |Min 2| is the absolute value of the minimum value of the second derivative of the coagulation waveform and represents the maximum coagulation acceleration. Max 2 is the maximum value of the second derivative of the coagulation waveform and represents the maximum coagulation deceleration. AUC is the area of a region surrounded by the coagulation waveform or a waveform obtained by first derivative or second derivative of the coagulation waveform. Slope is the magnitude of the slope of a tangent at an arbitrary point of the coagulation waveform or a waveform obtained by first derivative or second derivative of the coagulation waveform. Among them, |Min 1|, |Min 2| and Max 2 are preferable. |Min 1|, |Min 2| and Max 2 are also denoted as |min 1|, |min 2| and max 2, respectively. The parameter on differentiation of coagulation waveform may be a value obtained by combining two or more of these values. Examples thereof include the sum, difference, product, and ratio of at least two values selected from |Min 1|, |Min 2|, Max 2, AUC and Slope, and the like.

When the coagulation time has been also acquired, the parameter on differentiation of coagulation waveform may be a value obtained by combining the value acquired from the first derivative or second derivative of the coagulation waveform with the coagulation time. Examples of the value include the sum, difference, product, and ratio of at least one value selected from |Min 1|, |Min 2| and Max 2, AUC and Slope and the value of coagulation time, and the like.

In the method according to the first embodiment, the coagulability of a blood specimen containing a substance having a FVIII-substituting activity is evaluated, based on the value of the acquired parameter. In the present embodiment, the degree of promotion of the blood coagulation reaction by the substance having a FVIII-substituting activity can be quantitatively evaluated based on the parameter. Accordingly, it is possible to evaluate the activity as a cofactor of the substance, that is, the efficacy of the substance.

In the present embodiment, it is preferable to acquire a value indicating the coagulability of a blood specimen, from the value of the acquired parameter. As the value indicating coagulability, an index reflecting the activity of blood coagulation is preferable, and the FVIII activity value is particularly preferable. The FVIII activity value may be expressed as a percentage when the activity value of a healthy subject is taken as 100%, or it may be expressed as an international unit (IU/dL or U/dL) in a predetermined amount of plasma.

For example, acquisition of the FVIII activity value from the value of the acquired parameter can be performed as follows. First, a FVIII preparation is added to commercially available FVIII-deficient plasma at various concentrations to prepare a specimen whose FVIII activity value is known. The FVIII activity value of these specimens may be determined by a known method such as a synthetic substrate method or may be determined from the addition amount of the preparation. Then, with respect to these specimens, a parameter on differentiation of coagulation waveform is acquired as described above, using the FXII-activating agent, the phospholipids and the calcium solution described above. For each specimen, a calibration curve is prepared by plotting the value of the parameter with respect to the FVIII activity value. Based on the resulting calibration curve, the value of the parameter for the blood specimen containing a substance having a FVIII-substituting activity is converted into FVIII activity value. The calibration curve may be created for each measurement of a blood specimen, or a predetermined calibration curve may be used. Alternatively, by accumulating data, an equation for directly converting from the value of the parameter to the value indicating coagulability of a blood specimen may be derived.

In the present embodiment, the coagulability of a blood specimen containing a substance having a FVIII-substituting activity can be evaluated, based on the acquired value indicating coagulability. For example, when the FVIII activity value has been acquired from the value of the acquired parameter, the efficacy of the substance having a FVIII-substituting activity can be evaluated in the same manner as the efficacy of the FVIII preparation. The appropriate range when converting the efficacy of the substance having a FVIII-substituting activity into FVIII activity value may be defined as 0.2 U/dL or more and 0.4 U/dL or less or FVIII per 1 μg/mL of ACE910. This range was calculated based on the effect of hemostatic effect and pharmacokinetics of porcine FVIII and ACE910 in the cynomolgus hemophilia model (see Non Patent Literature 2). Comparing at the maximum blood concentration at each dose when showing equivalent hemostatic activity, ACE910 was 61 μg/mL, porcine FVIII was 25 U/dL, and the expected haemostatic effect at 1 μg/mL ACE910 was equivalent to 0.4 U/dL of the FVIII preparation. Meanwhile, comparing at the minimum blood concentration at each dose when showing equivalent hemostatic activity, ACE910 was 36 μg/mL, porcine FVIII was 7.4 U/dL, and the expected haemostatic effect at 1 μg/mL ACE910 was equivalent to 0.2 U/dL of the FVIII preparation. Here, it is confirmed that the range of this converted value does not also deviate from the result of the number of bleeding in ACE910 clinical trial in hemophilia A patients.

The present inventors have newly found that tissue factor involved in the extrinsic coagulation pathway is further added, in addition to the FXII-activating agent and the phospholipids which are involved in the intrinsic coagulation pathway, whereby the coagulability of a blood specimen containing a substance having a FVIII-substituting activity can be evaluated. Hereinafter, a method for evaluating coagulability of a blood specimen according to the second embodiment that further uses tissue factor will be described (hereinafter, also referred to as "the method according to the second embodiment").

In the method according to the second embodiment, a measurement sample is prepared from a blood specimen containing a substance having a FVIII-substituting activity (preferably, a blood specimen obtained from a subject administered a substance having a FVIII-substituting activity), a FXII-activating agent, phospholipids, tissue factor, and a calcium ion-containing aqueous solution. In the present embodiment, the blood specimen, the substance having a FVIII-substituting activity, the FXII-activating agent, the phospholipids, and the calcium ion-containing aqueous solution are the same as those described in the method according to the first embodiment.

In the method according to the second embodiment, by further using tissue factor, monitoring of coagulability becomes possible even when the blood specimen is a specimen obtained from a subject using a combination of a bypass preparation and a substance having a FVIII-substituting activity. The bypass preparation is a generic term for preparations that can promote blood coagulation even when FVIII and/or FIX is not present in the blood in sufficient amount (that is, can bypass a coagulation pathway involving FVIII and/or FIX). As the bypass preparation, for example, an activated coagulation factor VII (FVIIa) preparation, an activated prothombin complex concentrate (APCC) and the like are known.

The tissue factor may be a natural tissue factor derived from a rabbit brain, a human placenta or the like, or may be tissue factor prepared by a genetic recombination technique. In the present embodiment, the final concentration of the tissue factor in the measurement sample is not particularly limited, and is, for example, 0.002 ng/mL or more and 7.3 ng/mL or less, and preferably 0.002 ng/mL or more and 0.49 ng/mL or less. In the present embodiment, the order of mixing the blood specimen, the FXII-activating agent, the phospholipids, and the tissue factor is not particularly limited. For example, either one of the FXII-activating agent, the phospholipids and the tissue factor may be mixed with the blood specimen, then the remaining two may be mixed simultaneously or sequentially. Or, the two selected from the FXII-activating agent, the phospholipids and the tissue factor may be mixed with the blood specimen, then the remaining one may be mixed. Alternatively, the FXII-activating agent, the phospholipids and the tissue factor may be mixed, then the blood specimen may be mixed.

In the method according to the second embodiment, the final concentration of the FXII-activating agent in the measurement sample is not particularly limited, and is, for example, 0.1 µM or more and 26 µM or less, and preferably 0.1 µM or more and 9.6 µM or less. The final concentration of the phospholipids in the measurement sample is also not particularly limited, and is, for example, 0.39 µM or more and 43 µM or less, and preferably 0.39 µM or more and 13 µM or less.

In the method according to the second embodiment, the measurement sample obtained as described above is irradiated with light to acquire optical information on the light amount from the measurement sample. In the method according to the second embodiment, the coagulability of a blood specimen containing a substance having a FVIII-substituting activity is evaluated, based on the acquired optical information. In the present embodiment, it is preferable to acquire at least one selected from the coagulation time and the parameter on differentiation of coagulation waveform from the acquired optical information, and evaluate the coagulability of a blood specimen, based on the acquired value. Here, the optical information and the type of parameter on differentiation of coagulation waveform and the procedure of acquisition are the same as those described in the method according to the first embodiment. The procedure for evaluating coagulability of a blood specimen is also the same as described in the method according to the first embodiment.

[2. Reagent and Reagent Kit for Evaluating Coagulability of Blood Specimen]

The scope of the present invention also includes a reagent for evaluating coagulability of a blood specimen containing a substance having a FVIII-substituting activity (hereinafter, also referred to simply as "reagent"). The reagent according to the third embodiment is suitable for use in the method according to the first embodiment described above, and contains a FXII-activating agent and phospholipids respectively at a predetermined concentration. The reagent accommodated in a first container 111 is shown in FIG. 2, as an example of the appearance of the reagent of the present embodiment. The types of the FXII-activating agent and the phospholipids are the same as those described for the method of the present embodiment.

In the reagent according to the third embodiment, the concentration of the FXII-activating agent in the reagent is not particularly limited as long as the final concentration in the measurement sample can be adjusted to the range described in the method according to the first embodiment. When preparing the measurement sample with a fully automatic coagulation time measuring apparatus, the concentration of the FXII-activating agent is, for example, 3 µM or more and 66 µM or less, in consideration of the amount of reagent that can be aspirated by the apparatus.

In the present embodiment, the concentration of the phospholipids in the reagent is not particularly limited as long as the final concentration in the measurement sample can be adjusted to the range described in the method according to the first embodiment. When preparing a measurement sample with a fully automatic coagulation time measuring apparatus, the concentration of the phospholipids is, for example, 4.2 µM or more and 99 µM or less, in consideration of the amount of reagent that can be aspirated by the apparatus. When PE, PC and PS are contained as phospholipids, the sum of the concentrations of PE, PC and PS in the reagent may be within the above range.

In the present embodiment, when the concentration of the FXII-activating agent in the reagent is set at 3 µM or more and 8.7 µM or less, the concentration of the phospholipids in the reagent may be, for example, 4.2 µM or more and 129 µM or less.

Also, the scope of the present invention also includes a reagent kit for evaluating coagulability of a blood specimen containing a substance having a FVIII-substituting activity (hereinafter, also referred to simply as "reagent kit"). The reagent kit according to the fourth embodiment is suitable for use in the method according to the first embodiment described above and comprises a first reagent containing a FXII-activating agent and phospholipids respectively at a predetermined concentration and a coagulation initiation reagent comprising a calcium ion-containing aqueous solution. The reagent kit including a first reagent accommodated in a first container 111 and a coagulation initiation reagent accommodated in a second container 112 is shown in FIG. 3A, as an example of the appearance of the reagent kit according to the fourth embodiment. The types of the FXII-activating agent and the phospholipids are the same as those described for the method of the present embodiment. In addition, each concentration of the FXII-activating agent and the phospholipids in the reagent is as described above.

In the present embodiment, the coagulation initiation reagent is the same as the calcium ion-containing aqueous solution used in the method according to the first embodiment. The calcium ion content in the coagulation initiation reagent may be any amount as long as it can be adjusted to a final concentration capable of causing coagulation, and for example, it is usually 2.5 mM or more and 40 mM or less, and preferably 10 mM or more and 30 mM or less, in terms of calcium chloride concentration.

In a further embodiment, the reagent for evaluating coagulability of a blood specimen containing a substance having a FVIII-substituting activity may further contain tissue factor, in addition to the FXII-activating agent and the phospholipid. Hereinafter, the reagent according to the fifth embodiment further using tissue factor will be described.

The reagent according to the fifth embodiment is suitable for use in the method according to the second embodiment described above, and contains a FXII-activating agent, phospholipids, and tissue factor. The appearance of the reagent of the present embodiment is similar to that of the reagent according to the third embodiment, and is shown, for example, in FIG. 2. Specifically, a reagent containing a FXII-activating agent, phospholipids, and tissue factor is accommodated in the first container 111. The types of the FXII-activating agent, the phospholipids and the tissue factor are the same as those described for the methods according to the first and second embodiments. In addition, the respective concentration of each of the FXII-activating agent and the phospholipids in the reagent according to the fifth embodiment is not particularly limited, and for example, may be the same as that described for the reagent according to the third embodiment. In the reagent according to the fifth embodiment, the concentration of the tissue factor in the reagent is not particularly limited, and is, for example, 0.006 ng/mL or more and 21.9 ng/mL or less.

In a further embodiment, the reagent kit for evaluating coagulability of a blood specimen containing a substance having a FVIII-substituting activity may further contain tissue factor, in addition to the FXII-activating agent and the phospholipids. Hereinafter, the reagent kits according to the sixth and seventh embodiments further using tissue factor will be described.

The reagent kits according to the sixth and seventh embodiments are suitable for use in the method according to the second embodiment described above. The reagent kit according to the sixth embodiment comprises a first reagent containing a FXII-activating agent, phospholipids and tissue factor, and a coagulation initiation reagent comprising a calcium ion-containing aqueous solution. The appearance of the reagent kit according to the sixth embodiment is similar to that of the reagent kit according to the fourth embodiment, and is shown, for example, in FIG. 3A. Specifically, a first reagent containing a FXII-activating agent, phospholipids and tissue factor is accommodated in a first container 111, and a coagulation initiation reagent comprising a calcium ion-containing aqueous solution is accommodated in a second container 112.

The reagent kit according to the seventh embodiment comprises a first reagent, a second reagent, and a coagulation initiation reagent comprising a calcium ion-containing aqueous solution. The reagent kit including a first reagent accommodated in a first container 111, a second reagent accommodated in a second container 112, and a coagulation initiation reagent accommodated in a third container 113 are shown in FIG. 3B, as an example of the appearance of the reagent kit according to the seventh embodiment. In the present embodiment, each of the FXII-activating agent, the phospholipid, and the tissue factor may be contained in either the first reagent or the second reagent. For example, it is possible that the first reagent contains the FXII-activating agent and the phospholipids and the second reagent contains the tissue factor, the first reagent contains the FXII-activating agent and the phospholipids and the second reagent contains the tissue factor and the phospholipids, or the first reagent contains the FXII-activating agent and the tissue factor and the second reagent contains the phospholipids.

In the reagent kits according to the sixth and seventh embodiments, the types and concentrations of the FXII-activating agent, phospholipids and tissue factor in the reagent are not particularly limited, and are, for example, the same as the concentrations as those described for the reagents according to the third and fifth embodiments as described above. In the reagent kit according to the seventh embodiment, when phospholipids are contained in both the first reagent and the second reagent, the concentration of the phospholipids in each reagent may be half the concentration as described for the reagent according to the third embodiment. In addition, the coagulation initiation reagent comprising the calcium ion-containing aqueous solution is the same as that described for the reagent kit according to the fourth embodiment as described above.

The reagent kit according to the twelfth embodiment is suitable for use in the method according to the second embodiment described above. The reagent kit according to the twelfth embodiment comprises a first reagent and a second reagent. In the present embodiment, the first reagent contains a FXII-activating agent and phospholipids, and the second reagent contains tissue factor and calcium ions. The second reagent may further contain phospholipids. The appearance of the reagent kit according to the twelfth embodiment is similar to that of the reagent kit according to the fourth embodiment, and is shown, for example, in FIG. 3A. Specifically, a first reagent containing a FXII-activating agent and phospholipids is accommodated in a first container 111, and a second reagent containing tissue factor and calcium ions is accommodated in a second container 112.

In the reagent kit according to the twelfth embodiment, the types and concentrations of the FXII-activating agent, phospholipids and tissue factor in each reagent are not particularly limited, and for example, are the same as the concentrations as those described for the reagents according to the third and fifth embodiments as described above. In the reagent kit according to the twelfth embodiment, when phospholipids are contained in both the first reagent and the second reagent, the concentration of the phospholipids in each reagent may be half the concentration as described for the reagent according to the third embodiment. In addition, the content of calcium ions in the second reagent is the same as that described for the coagulation initiation reagent of the reagent kit according to the fourth embodiment as described above. In the present embodiment, the second reagent contains calcium ions that are a coagulation initiation reagent. Therefore, first, a first reagent and a blood specimen containing a substance having a coagulation factor VIII-substituting activity are mixed, and then a second reagent is added to the obtained mixture.

[3. Blood Specimen Analyzer, Apparatus for Evaluating Coagulability of Blood Specimen and Computer Program]

An example of the blood specimen analyzer according to the present embodiment will be described below, with reference to the drawings. However, the present embodiment is not limited to this example. As shown in FIG. 4, a blood specimen analyzer 10 includes a measurement device 50 for preparing and optically measuring a measurement sample, a control device 40 for analyzing measurement data acquired by the measurement device 50 and giving an instruction to the measurement device 50. The measurement device 50 includes a measurement unit 20 for acquiring optical information on the light amount from the measurement sample, and a specimen transporting unit 30 arranged in front of the measurement unit 20.

The measurement unit 20 is provided with lids 20a and 20b, a cover 20c, and a power button 20d. A user can open the lid 20a and replace a reagent container 103 placed in reagent tables 11 and 12 (see FIG. 5) with a new reagent container 103, or a user can newly add another reagent container 103. To the reagent container 103 is attached a barcode label 103a printed with a barcode including the type of the reagent to be accommodated and a reagent ID made up of serial number provided to the reagent.

The user can open the lid 20b and replace a lamp unit 27 (see FIG. 5). The user can also open the cover 20c and replace a piercer 17a (see FIG. 5). The specimen transporting unit 30 transports a specimen container 101 supported by a specimen rack 102 to an aspiration position by the piercer 17a. The specimen container 101 is hermetically sealed by a rubber lid 101a.

When using the blood specimen analyzer 10, the user first presses the power button 20d of the measurement unit 20 to activate the measurement unit 20, and presses a power button 439 of the control device 40 to activate the control device 40. When the control device 40 is activated, a log-on screen is displayed on a display unit 41. The user inputs the user name and the password on the log-on screen to log on to the control device 40, and starts using the blood specimen analyzer 10.

The configuration of the measurement device will be described below. As shown in FIG. 5, the measurement unit 20 includes reagent tables 11 and 12, a cuvette table 13, a barcode reader 14, a cuvette supply section 15, a catcher 16, a specimen dispensing arm 17, a reagent dispensing arm 18, an urgent specimen setting section 19, an optical fiber 21, a detecting section 22, a cuvette transfer section 23, a warming section 24, a disposal port 25, a fluid section 26, and a lamp unit 27.

(Measurement Sample Preparing Section)

Each of the reagent tables 11 and 12 and the cuvette table 13 has an annular shape and is configured rotatably. Each of the reagent tables 11 and 12 corresponds to a reagent storing section, onto which a reagent container 103 is placed. The barcode of the reagent container 103 placed on the reagent tables 11 and 12 is read by the barcode reader 14. Information (type of reagent, reagent ID) read from the barcode is input to the control device 40 and stored in a hard disk 434 (see FIG. 10).

In the apparatus according to the eighth embodiment, the reagent container 103 in which an APTT measuring reagent containing a FXII-activating agent and phospholipids, a diluent for diluting the reagent, a calcium solution, and the like are each accommodated is placed on the reagent tables 11 and/or 12. In the apparatus according to the ninth embodiment, the reagent container 103 in which a FXII-activating agent, phospholipids, tissue factor, a calcium solution, and the like are each accommodated is placed on the reagent tables 11 and/or 12. Alternatively, the reagent container 103 in which the reagent according to the fifth embodiment or each reagent of the kit according to the sixth or seventh embodiment is each accommodated may be placed. In any of the apparatuses, the reagent container 103 in which each of the FVIII preparation and the FVIII-deficient plasma is accommodated may be placed on the reagent tables 11 and/or 12.

The cuvette table 13 is formed with a support portion 13a composed of a plurality of holes capable of supporting a cuvette 104. A new cuvette 104 introduced into the cuvette supply section 15 by the user is sequentially transferred by the cuvette supply section 15, and the cuvette 104 is placed on the support portion 13a of the cuvette table 13 by the catcher 16.

A stepping motor is connected to each of the specimen dispensing arm 17 and the reagent dispensing arm 18 so as to be able to move up and down and rotatably. A piercer 17a of which a tip is sharply formed is provided at the tip of the specimen dispensing arm 17, so that the lid 101a of the specimen container 101 can be punctured. A pipette 18a is provided at the tip of the reagent dispensing arm 18. The tip of the pipette 18a is formed flat unlike the piercer 17a. An electrostatic capacitance type liquid level detection sensor 213 (see FIG. 6) is connected to the pipette 18a.

When the specimen container 101 is transported to a predetermined position by the specimen transporting unit 30 (see FIG. 4), the piercer 17a is positioned just above the specimen container 101 by the rotational movement of the specimen dispensing arm 17. Then, the specimen dispensing arm 17 is moved downward, the piercer 17a penetrates the lid 101a of the specimen container 101, and the blood specimen accommodated in the specimen container 101 is aspirated by the piercer 17a. When an urgent blood specimen is set in the urgent specimen setting section 19, the piercer 17a intervenes in the specimen supplied from the specimen transporting unit 3 and aspirates the urgent blood specimen. The blood specimen aspirated by the piercer 17a is discharged into an empty cuvette 104 on the cuvette table 13.

The cuvette 104 into which the blood specimen has been discharged is transferred from the support portion 13a of the cuvette table 13 to a support portion 24a of the warming section 24 by a catcher 23a of the cuvette transfer section 23. The warming section 24 warms the blood specimen accommodated in the cuvette 104 placed in the support portion 24a at a predetermined temperature (for example, 37° C.) for a certain period of time. When the warming of the blood specimen by the warming section 24 is finished, the cuvette 104 is again gripped by the catcher 23a. Then, the cuvette 104 is positioned at a predetermined position while being gripped by the catcher 23a, and in this state, the reagent aspirated by the pipette 18a is discharged into the cuvette 104.

In the dispensing of the reagent by the pipette 18a, first, the reagent tables 11 and 12 are rotated, and the reagent container 103 that accommodates the reagent corresponding to the measurement item is transported to an aspiration position by the pipette 18a. Then, after the position of the pipette 18a in the vertical direction is positioned at the origin position, the pipette 18a is lowered until the lower end of the pipette 18a comes into contact with the liquid level of the reagent by the liquid level detection sensor 213. When the lower end of the pipette 18a comes into contact with the liquid level of the reagent, the pipette 18a is further lowered to an extent that a necessary amount of the reagent can be aspirated. Then, the lowering of the pipette 18a is stopped, and the reagent is aspirated by the pipette 18a. The reagent aspirated by the pipette 18a is discharged into the cuvette 104 gripped by the catcher 23a. Then, the blood specimen and the reagent in the cuvette 104 are agitated by the vibrating function of the catcher 23a. Thus, the measurement sample is prepared. Thereafter, the cuvette 104 that accommodates the measurement sample is transferred to a support portion 22a of the detecting section 22 by the catcher 23a.

(Optical Information Acquiring Section)

The lamp unit 27 supplies light having plural kinds of wavelengths used for detection of an optical signal by the detecting section 22. An example of the configuration of the lamp unit 27 will be described with reference to FIG. 7. The lamp unit 27 corresponds to a light source, and includes a halogen lamp 27a, a lamp case 27b, condenser lenses 27c to 27e, a disk-shaped filter section 27f, a motor 27g, a light transmission type sensor 27h, and an optical fiber coupler 27i.

With reference to FIG. 5, light from the lamp unit 27 is supplied to the detecting section 22 via the optical fiber 21. A plurality of hole-shaped support portions 22a is provided in the detecting section 22, and a cuvette 104 can be inserted into each of the support portions 22a. The end part of the optical fiber 21 is attached to each of the support portions 22a, and the cuvette 104 supported by the support portion 22a can be irradiated with light from the optical fiber 21. The detecting section 22 irradiates the cuvette 104 with light supplied from the lamp unit 27 via the optical fiber 21 and detects the light amount of light to be transmitted through the cuvette 104 (or scattered light from the cuvette 104).

FIGS. 8A to 8D show an example of one configuration of the plurality of support portions 22a arranged in the detecting section 22, and the other support portions 22a have the same configuration. With reference to FIG. 8A, the detecting section 22 is formed with a circular hole 22b into which the tip of the optical fiber 21 is inserted. The detecting section 22 is further formed with a circular communication hole 22c for communicating the hole 22b with the support portion 22a. The diameter of the hole 22b is larger than the diameter of the communication hole 22c. A lens 22d for condensing light from the optical fiber 21 is arranged at the end of the hole 22b. Further, on the inner wall surface of the support portion 22a, a hole 22f is formed at a position facing the communication hole 22c. A photodetector 22g is arranged at the back of the hole 22f. The photodetector 22g corresponds to a light receiving portion, and outputs an electric signal corresponding to the amount of received light. The light transmitted through the lens 22d is condensed on the light receiving surface of the photodetector 22g, through the communication hole 22c, the support portion 22a, and the hole 22f. The optical fiber 21 is prevented from falling off by a plate spring 22e in a state in which the end part of the optical fiber 21 is inserted into the hole 22b.

With reference to FIG. 8B, when the cuvette 104 is supported by the support portion 22a, the light condensed by the lens 22d is transmitted through the cuvette 104 and the sample accommodated in the cuvette 104, and the transmitted light enters the photodetector 22g. As the blood coagulation reaction progresses in the sample, the turbidity of the sample increases. Along with this, the amount of light to be transmitted through the sample (the amount of transmitted light) decreases, and the level of the detection signal of the photodetector 22g decreases.

With reference to FIG. 8C, the configuration of the detecting section 22 when scattered light is used will be described. On the inner side surface of the support portion 22a, a hole 22h is provided at a position which is the same height as the communication hole 22c. A photodetector 22i is arranged at the back of the hole 22h. When the cuvette 104 is inserted into the support portion 22a and light is emitted from the optical fiber 21, the light scattered by the measurement sample in the cuvette 104 is irradiated to the photodetector 22i via the hole 22h. In this example, the detection signal from the photodetector 22i indicates the intensity of scattered light by the measurement sample. Also, as shown in FIG. 8D, both the light to be transmitted through the measurement sample and the light to be scattered by the measurement sample may be detected.

As described above, the detecting section 22 irradiates the cuvette 104 with light supplied from the lamp unit 27, and acquires optical information from the measurement sample. The acquired optical information is transmitted to the control device 40. The control device 40 performs analysis based on the optical information and displays the analysis result on a display unit 41.

After completion of the measurement, the cuvette 104 that has become unnecessary is transported by the cuvette table 13, and discarded to the disposal port 25 by the catcher 16. During the measurement operation, the piercer 17a and the pipette 18a are appropriately washed with a liquid such as a cleaning liquid supplied from the fluid section 26.

The hardware configuration of the measurement device will be described below. As shown in FIG. 6, the measurement unit 20 includes a control section 200, a stepping motor section 211, a rotary encoder section 212, a liquid level detection sensor 213, a sensor section 214, a mechanism section 215, an optical information acquiring section 216, and a barcode reader 14.

With reference to FIG. 6, the control section 200 includes a CPU 201, a memory 202, a communication interface 203, and an I/O interface 204. The CPU 201 executes a computer program stored in the memory 202. The memory 202 is composed of a ROM, a RAM, a hard disk, and the like. The CPU 201 drives the specimen transporting unit 30 via the communication interface 203 and also transmits and receives instruction signals and data with the control device 40. The CPU 201 controls each section in the measurement unit 20 via the I/O interface 204, and also receives signals outputted from each section.

The stepping motor section 211 includes stepping motors for driving the reagent tables 11 and 12, the cuvette table 13, the catcher 16, the specimen dispensing arm 17, the reagent dispensing arm 18, and the cuvette transfer section 23, respectively. The rotary encoder section 212 includes a rotary encoder that outputs a pulse signal corresponding to the amount of rotational displacement of each stepping motor included in the stepping motor unit 211.

The liquid level detection sensor 213 is connected to the pipette 18a provided at the tip of the reagent dispensing arm 18, and detects that the lower end of the pipette 18a has come into contact with the liquid level of the reagent. The sensor section 214 includes a sensor for detecting that the vertical position of the pipette 18a is positioned at the origin position and a sensor for detecting that the power button 20d is pressed. The mechanism section 215 includes a mechanism for driving the cuvette supply section 15, the urgent specimen setting section 19, the warming section 24 and the fluid section 26, and an air pressure source which supplies pressure to the piercer 17a and the pipette 18a so that dispensing operation by the piercer 17a and the pipette 18a can be performed. With reference to FIG. 5, the optical information acquiring section 216 includes at least the lamp unit 27, the optical fiber 21, and the detecting section 22.

The configuration of the control device 40 will be described below. As shown in FIG. 4, the control device 40 includes the display unit 41, an input unit 42, and a computer body 43. The control device 40 receives optical information from the measurement unit 20. Then, a processor of the control device 40 calculates a parameter on differentiation of coagulation waveform based on the optical information. The processor of the control device 40 may also calculate coagulation time based on the optical information. Then, the processor of the control device 40 executes a computer program for evaluating coagulability of a blood specimen. Accordingly, the control device 40 also functions as an apparatus for evaluating coagulability of a blood specimen.

As to the functional configuration of the control device 40, as shown in FIG. 9, the control device 40 includes an acquisition unit 401, a storage unit 402, a calculation unit 403, and an output unit 404. The acquisition unit 401 is communicably connected to the measurement unit 20 via a network. The output unit 404 is communicably connected to the display unit 41.

The acquisition unit 401 acquires the optical information transmitted from the measurement unit 20. The storage unit 402 stores an expression for calculating values of various parameters on differentiation of coagulation waveform and the like. The storage unit 402 may also store an expression for calculating coagulation time, an expression for converting a parameter on differentiation of coagulation waveform into a FVIII activity value or the like, and a threshold value for the value of the parameter or a converted value thereof. Using the information acquired by the acquisition unit 401, the calculation unit 403 calculates the values of the various parameters, according to the expression stored in the storage unit 402. Further, the calculation unit 403 may convert the value of the calculated parameter into the FVIII activity value. The output unit 404 outputs the values of the parameters calculated by the calculation unit 403 or a converted value thereof, as reference information regarding the blood specimen.

As shown in FIG. 10, the computer body 43 of the control device 40 includes a CPU 431, a ROM 432, a RAM 433, a hard disk 434, a reading device 435, an input/output interface 436, a communication interface 437, an image output interface 438, and a power button 439. The CPU 431, the ROM 432, the RAM 433, the hard disk 434, the reading device 435, the input/output interface 436, the communication interface 437, the image output interface 438, and the power button 439 are communicably connected by a bus 440.

The CPU 431 executes a computer program stored in the ROM 432 and a computer program loaded in the RAM 433. Each of the above-described functional blocks is realized by the CPU 431 executing an application program. Thus, the computer system functions as a terminal serving as a determination device for evaluating coagulability of a blood specimen.

The ROM 432 includes a mask ROM, PROM, EPROM, EEPROM, and the like. In the ROM 432, a computer program executed by the CPU 431 and data used for the computer program are recorded.

The RAM 433 includes SRAM, DRAM, and the like. The RAM 433 is used for reading the computer program recorded in the ROM 432 and the hard disk 434. The RAM 433 is also used as a work area of the CPU 431 when executing these computer programs.

The hard disk 434 has installed therein an operating system, a computer program such as an application program (a computer program for evaluating coagulability of a blood specimen) to be executed by the CPU 431, data used for executing the computer program, and setting contents of the control device 40.

The reading device 435 includes a flexible disk drive, a CD-ROM drive, a DVD-ROM drive, and the like. The reading device 435 can read a computer program or data recorded on a portable recording medium 441 such as a CD or a DVD.

The input/output interface 436 includes, for example, a serial interface such as USB, IEEE1394 or RS-232C, a parallel interface such as SCSI, IDE or IEEE1284, and an analog interface including a D/A converter, an A/D converter and the like. The input unit 42 such as a keyboard and a mouse is connected to the input/output interface 436. The user inputs an instruction via the input unit 42, and the input/output interface 436 receives a signal input via the input unit 42.

The communication interface 437 is, for example, an Ethernet (registered trademark) interface or the like. The control device 40 can transmit print data to a printer through the communication interface 437. The communication interface 437 is connected to the measurement unit 20, and the CPU 431 transmits and receives an instruction signal and data with the measurement unit 20 via the communication interface 437.

The image output interface 438 is connected to the display unit 41 including an LCD, a CRT, and the like. The image output interface 438 outputs a video signal corresponding to image data to the display unit 41, and the display unit 41 displays an image based on the video signal outputted from the image output interface 438.

With reference to FIG. 6, during the measurement operation, the CPU 201 of the measurement unit 20 temporarily stores in the memory 202 the data (optical information) obtained by digitizing the detection signal outputted from the detecting section 22 (see FIG. 5). The storage area of the memory 202 is divided into areas for each support portion 22a. In each area, the data (optical information) which are acquired when the cuvette 104 supported by the corresponding support portion 22a is irradiated with light having a predetermined wavelength are sequentially stored. Thus, the data are sequentially stored in the memory 202 over a predetermined measurement time. When the measurement time elapses, the CPU 201 stops storing the data in the memory 202, and transmits the stored data to the control device 40 via the communication interface 203. The control device 40 processes and analyzes the received data, and displays the analysis result on the display unit 41.

The processing in the measurement unit 20 is mainly performed under the control of the CPU 201 of the measurement unit 20, and the processing in the control device 40 is mainly performed under the control of the CPU 431 of the control device 40. With reference to FIG. 11, when the measurement processing is started, the measurement unit 20 aspirates a predetermined amount of a test plasma from the specimen container 101 transported by the specimen transporting unit, and dispenses the aspirated blood specimen into an empty cuvette 104 on the cuvette table 13. When also measuring FVIII-deficient plasma as a control, the measurement unit 20 aspirates a predetermined amount of FVIII-deficient plasma from the reagent container 103 containing FVIII-deficient plasma accommodated in the reagent accommodating section, and dispenses it into an empty cuvette 104. When also measuring FVIII-deficient plasma to which FVIII preparation is added, the measurement unit 20 aspirates a predetermined amount of FVIII-deficient plasma from the reagent container 103 in which the FVIII-deficient plasma is accommodated, and dispenses it into an empty cuvette 104. Then, the measurement unit 20 aspirates a predetermined amount of the FVIII preparation from the reagent container 103 in which the FVIII preparation is accommodated, dispenses it into the cuvette 104 containing the FVIII-deficient plasma, and stirs it.

Subsequently, the measurement unit 20 transfers the cuvette 104 into which the plasma is dispensed to the warming section 24, and warms the plasma in the cuvette 104 to a predetermined temperature (for example, 37° C.). Thereafter, the measurement unit 20 adds a reagent and a calcium solution to the cuvette 104 to prepare a measurement sample (step S11). Here, in the apparatus according to the eighth embodiment, when a usual APTT measuring reagent containing a FXII-activating agent and phospholipids is placed, the measurement unit 20 can dilute the APTT measuring reagent with a predetermined ratio with a diluent to prepare a reagent for blood coagulation analysis. Specifically, a reagent for blood coagulation analysis can be prepared as follows. The measurement unit 20 aspirates a predetermined amount of the usual APTT measuring reagent from the reagent container 103 in which the reagent is accommodated and dispenses it into an empty reagent container 103. Then, the measurement unit 20 aspirates a predetermined amount of the diluent from the reagent container 103 in which the diluent is accommodated, adds it to the reagent container 104 into which the usual APTT measuring reagent is dispensed, and stirs it. The dilution ratio can be determined as appropriate depending on the APTT measuring reagent to be used, and is, for example, 1.3 times or more and 30 times or less, and preferably 2 times or more and 10 times or less, in the case of a general commercially available APTT measuring reagent. In the apparatus according to the eighth embodiment, a reagent obtained by diluting a general commercially available APTT measuring reagent is used as a reagent for blood coagulation analysis.

In a preferred embodiment, the measurement unit 20 prepares a measurement sample using the diluted APTT measuring reagent, so that the final concentration of the FXII-activating agent in the measurement sample is 1 µM or more and 22 µM or less and the final concentration of the phospholipids is 1.4 µM or more and 33 µM or less, or the final concentration of the FXII-activating agent in the measurement sample is 1 µM or more and 2.9 µM or less and the final concentration of phospholipids is 1.4 µM or more and 43 µM or less.

Thereafter, the measurement unit 20 transfers the cuvette 104 to which the reagent is added to the detecting section 22, and irradiates the cuvette 104 with light to measure the measurement sample (step S12). The measurement unit 20 starts measuring time from the time when the calcium solution is added to the cuvette 104. In this measurement, data (the amount of scattered light or the amount of transmitted light) based on the light with a wavelength of 660 nm is sequentially stored in the memory 202 during the measurement time. At this time, the data is stored in the memory 202 in a state associated with the elapsed time from the addition time point of the calcium solution. Then, when the measurement time elapses, the measurement unit 20 stops the measurement, and transmits the measurement result (data) stored in the memory 202 to the control device 40 (step S13). Accordingly, when the control device 40 receives the measurement result (data) from the measurement unit 20 (step S21: YES), the control device 40 executes analysis processing on the received measurement result (step S22). That is, the control device 40 converts from the parameters on differentiation of coagulation waveform (|Min 1|, |Min 2|, Max 2, AUC and Slope) into a value indicating coagulability of a blood specimen (for example, FVIII activity value), for a measurement sample. The control device 40 may also calculate the coagulation time and coagulation waveform of the measurement sample. After performing the analysis processing, the control device 40 executes display processing of the analysis result (step S23).

With reference to FIG. 12, the processing flow when using one parameter on differentiation of coagulation waveform will be described. Here, a case where the value of |min 1| as the value of the parameter on differentiation of coagulation waveform is acquired from the optical information on the light amount from the measurement sample, the acquired value is converted to acquire a FVIII value, and this FVIII value is outputted as reference information on coagulability of a blood specimen will be described as an example. However, the present embodiment is not limited to this example. In this example, values of |min 2|, max 2, AUC or Slope may be acquired, in place of |min 1|. Alternatively, a plurality of parameters may be acquired, and the FVIII value may be acquired from the value of each parameter. In this case, as the reference information, the average value, the minimum value, the maximum value and the like of the FVIII value converted from the values of the plurality of parameters may be outputted.

First, in step S101, the acquisition unit 401 of the control device 40 acquires optical information (scattered light intensity, or transmittance or absorbance), based on the data (the amount of scattered light or the amount of transmitted light) received from the measurement unit 20. Next, in step S102, the calculation unit 403 calculates a value of |min 1| from the optical information acquired by the acquisition unit 401, according to the equation for calculating a parameter on differentiation of coagulation waveform stored in the storage unit 402. Although the coagulation time and the coagulation waveform are not used for the determination processing described later, the calculation unit 403 may further calculate the coagulation time and the coagulation waveform from the optical information acquired by the acquisition unit 401.

In step S103, the calculation unit 403 calculates the FVIII activity value from the calculated value of |min 1|, according to the conversion formula stored in the storage unit 402. In step S103, the calculation unit 403 transmits the acquired FVIII activity value to the output unit 404. In step S104, the output unit 404 outputs the FVIII activity value, and displays it on the display unit 41, or makes a printer to print it. Alternatively, the FVIII activity value may be outputted by voice. As a result, the FVIII activity value can be provided to the user as reference information on coagulability of the test plasma.

As an example of a screen displaying the analysis result, a screen for displaying the result of analyzing the coagulation process of the test plasma using a reagent containing a FXII-activating agent and phospholipids will be described with reference to FIG. 13. A screen D1 includes an area D11 for displaying a specimen number, an area D12 for displaying a measurement item name, a button D13 for displaying a detailed screen, an area D14 for displaying measurement data and time, an area D15 for displaying measurement results, an area D16 for displaying analysis information, and an area D17 for displaying a coagulation waveform and a graph obtained by differentiating it.

In the area D15, measurement items and measurement values are displayed. In the area D15, the "APTT sec" is the activated partial thromboplastin time. |Min 1|, |Min 2|, Max 2 and the like may be displayed as values of parameters on differentiation of coagulation waveform in the region D15.

In the area D16, analysis items and reference information are displayed. In the area D16, the "Index" is the value of the parameter on differentiation of the coagulation waveform used for the calculation of FVIII activity value. The "FVIII converted value (reference)" is the value of the FVIII activity value converted from the value of Index. The evaluation of the efficacy of a substance having a FVIII-substituting activity is desirably performed not only based on this result, but also information such as other examination results and physical findings of the subject. Accordingly, it is displayed as "(reference)" to indicate that the FVIII converted value by the blood specimen analyzer according to the present embodiment is reference information.

Hereinafter, the present invention will be described in more detail with reference to examples, but the present invention is not limited to these examples.

EXAMPLES

Example 1

Whether or not the coagulability of a blood specimen containing a substance having a FVIII-substituting activity could be appropriately evaluated by diluting a commercially available APTT measuring reagent and using it as a reagent for blood coagulation analysis whose concentrations of a FXII-activating agent and phospholipids were adjusted was investigated.

(1) Reagent

As the commercially available APTT measuring reagent, Thrombocheck APTT-SLA (Sysmex Corporation) was used. This reagent is composed of ellagic acid (86.4 µM) as a FXII-activating agent and synthetic phospholipids (130 µM). The APTT measuring reagent and Owren's Veronal buffer (Sysmex Corporation) were mixed in ratios of reagent:buffer of 3:1, 1:1, 1:2, 1:9 and 1:29 expressed by volume ratios to prepare reagents for blood coagulation analysis (corresponding to reagents of 1.33-fold, 2-fold, 3-fold, 10-fold and 30-fold dilutions of Thrombocheck APTT-SLA, respectively). As a coagulation initiation reagent containing calcium ions, a 20 mM calcium chloride solution (Sysmex Corporation) was used. Also, Thrombocheck APTT-SLA was used without dilution as a control.

(2) Substance Having Coagulation Factor VIII-Substituting Activity

ACE910 (Q499-z121/J327-z119/L404-k) which is an anti-FIXa/FX bispecific antibody described in Patent Literature (WO 2012/067176) was used as a substance having a FVIII-substituting activity. This antibody was acquired by the methods described in WO 2005/035756, WO 2006/109592 and WO 2012/067176. Specifically, the antibody was acquired as follows. First, the antibody gene described in WO 2012/067176 was incorporated into a vector for animal cell expression, and the resulting construct was transfected into HEK293 cells to express an anti-FIXa/FX bispecific antibody. Then, the bispecific antibody contained in the culture supernatant of the cells was purified by Protein A and gel filtration. It was confirmed that the resulting bispecific antibody had FXa production promoting activity, by the method described in WO 2012/067176, WO 2014/050926, or the like.

(3) Blood Specimen

The bispecific antibody ACE910 was added to FVIII-deficient human plasma (George King Bio-Medical) to a concentration of 0, 10, 30, 100 or 300 μg/mL to prepare blood specimens containing a substance having a FVIII-substituting activity. Also, as a specimen for preparing a calibration curve, blood specimens obtained by adding recombinant human FVIII (rhFVIII, Bayer Co., Ltd.) to FVIII-deficient human plasma (George King Bio-Medical) so as to have a concentration of 0, 1, 3, 10, 30, 100 or 200 IU/dL were prepared.

(4) Preparation and Measurement of Measurement Sample

For preparing and measuring a measurement sample, a fully automated blood coagulation measurement device CS-5100 (Sysmex Corporation) was used. A reagent for blood coagulation analysis (50 μL) was added to a blood specimen (50 μL), and the mixture was incubated at 37° C. for 3 minutes. Then, a measurement sample was prepared by adding a 20 mM calcium chloride solution (50 μL). The transmittance of the measurement sample was continuously measured for 420 seconds from the addition of the calcium chloride solution. The respective final concentrations of ellagic acid and phospholipids in the measurement sample are as shown in Table 1.

TABLE 1

| | Final concentration in measurement sample | |
|---|---|---|
| Dilution ratio | Ellagic acid (μM) | Phospholipid (μM) |
| No dilution | 28.8 | 43.3 |
| 1.33-fold | 21.6 | 32.5 |
| 2-fold | 14.4 | 21.6 |
| 3-fold | 9.6 | 14.4 |
| 10-fold | 2.9 | 4.3 |
| 30-fold | 1.0 | 1.4 |

(5) Analysis Results

The coagulation time and |Min 1|, |Min 2| and Max 2 were calculated as parameters on differentiation of coagulation waveform, based on the temporal change in the resulting transmittance, and plotted on a graph. The graphs of the coagulation time, |Min 1|, |Min 2| and Max 2 obtained from the blood specimens containing ACE910 and the blood specimens containing rhFVIII are shown in FIGS. 14A, 15A, 16A and 17A, respectively. The coagulation time, |Min 1|, |Min 2| and Max 2 of the blood specimens containing ACE910 were converted into FVIII activity values, using the graphs of the blood specimens containing rhFVIII as calibration curves, to create graphs from the resulting converted values. The resulting graphs are shown in FIGS. 14B, 15B, 16B and 17B, respectively.

The present inventors have previously found a relationship between ACE910 blood concentration and FVIII activity value from animal models of hemophilia. Specifically, based on the hemostatic effect of ACE910 and rhFVIII in cynomolgus monkeys exhibiting symptoms similar to acquired hemophilia A by administration of anti-FVIII-neutralizing antibody, ACE910 was defined to be converted into a FVIII activity value of 0.2 to 0.4 IU/dL per 1 μg/mL. In addition, the present inventors have confirmed that this converted value does not deviate from the result of clinical trial (the number of bleeding) in hemophilia A patients. Two broken lines in FIGS. 14B, 15B, 16B and 17B show graphs obtained by converting the ACE910 concentration into a FVIII activity value of 0.2 or 0.4 IU/dL per 1 μg/mL. The region sandwiched between these two broken lines was defined as the ideal range, and whether or not the reagent for blood coagulation analysis described above in which FVIII converted from each parameter is within this ideal range enables appropriate evaluation of coagulability of the blood specimen containing ACE910 was investigated. In particular, the results of the range of 10 to 100 μg/mL considered clinically important as the blood concentration of ACE910 was investigated.

As shown in FIG. 14B, the FVIII activity values converted from the coagulation time were largely deviated from the ideal range even when any of the reagents was used. This indicates that the FVIII activity value converted from the coagulation time deviates from the activity value predicted from the animal models. Accordingly, it was shown that the coagulability of the blood specimen containing ACE910 cannot be appropriately evaluated also based on the coagulation time. As shown in FIGS. 15B, 16B and 17B, in the case of using undiluted APTT reagent, the FVIII activity values each converted from |Min 1|, |Min 2| and Max 2 were not within the ideal range. Accordingly, it was shown that the coagulability of the blood specimen containing ACE910 cannot be appropriately evaluated with the commercially available APTT reagent. Meanwhile, when the reagents diluted 1.33 to 30-folds were used, among the FVIII activity values converted from |Min 1|, at least one FVIII activity value was included in the ideal range, in the range of an ACE910 concentration of 10 to 100 μg/mL. In addition, when the reagents diluted 2 to 3-folds were used, among the FVIII activity values converted from |Min 2|, at least one FVIII activity value was included in the ideal range, in the range of an ACE910 concentration of 10 to 100 μg/mL. In addition, when the reagents diluted 1.33 to 10-folds were used, among the FVIII activity values converted from Max 2, at least one FVIII activity value was included in the ideal range, in the range of an ACE910 concentration of 10 to 100 μg/mL. Accordingly, it was shown that the coagulability of a blood specimen containing a substance having a FVIII-substituting activity can be appropriately evaluated by adjusting the concentrations of the activators of the APTT measuring reagent and the phospholipids by dilution.

Example 2

Also as to commercially available APTT measuring reagents which were different from the reagent used in Example 1, whether the coagulability of a blood specimen containing a substance having a FVIII-substituting activity could be appropriately evaluated by diluting and using them was investigated in the same manner.

(1) Reagent

As the commercially available APTT measuring reagents, Thrombocheck APTT-SLA (Sysmex Corporation), Actin FSL (Sysmex Corporation), and Data Phi•APTT (FS) (Sysmex Corporation) were used. Actin FSL is composed of ellagic acid and phospholipids derived from soybean and rabbit brain. Data Phi•APTT (FS) is composed of ellagic acid and soybean-derived phospholipids. Each APTT measuring reagent and Owren's Veronal buffer (Sysmex Corporation) were mixed in a ratio of reagent:buffer of 1:2 expressed by a volume ratio to prepare a reagent for blood coagulation analysis (corresponding to a reagent of 3-fold dilution of each reagent). As a coagulation initiation reagent containing calcium ions, a 20 mM calcium chloride solution (Sysmex Corporation) was used. Also, each reagent was used without dilution as a control.

(2) Blood Specimen

The bispecific antibody ACE910 was added to FVIII-deficient human plasma (George King Bio-Medical) to a concentration of 0, 0.3, 1, 3, 10, 30, 100 or 300 μg/mL to prepare blood specimens containing a substance having a FVIII-substituting activity. Also, as a specimen for preparing a calibration curve, blood specimens obtained by adding recombinant human FVIII (rhFVIII, Bayer Co., Ltd.) to FVIII-deficient human plasma (George King Bio-Medical) so as to have a concentration of 0, 1, 3, 10, 30, 100 or 200 IU/dL were prepared.

(3) Preparation and Measurement of Measurement Sample

Preparation and measurement of the measurement sample were carried out in the same manner as in Example 1.

(4) Analysis Results

The coagulation time and |Min 1|, |Min 2| and Max 2 were calculated as parameters on differentiation of coagulation waveform, based on the temporal change in the resulting transmittance, and plotted on a graph. The coagulation time, |Min 1|, |Min 2| and Max 2 of the blood specimens containing ACE910 were converted into FVIII activity values, using the graphs of the blood specimens containing rhFVIII as calibration curves, to create graphs from the resulting converted values. FIGS. 18A to 18D show the converted values of each parameter obtained with the 3-fold diluted reagent, respectively. In these figures, the graphs indicated by the broken lines are the ideal ranges defined from the animal models as in Example 1.

The FVIII activity values converted from the coagulation time obtained using each undiluted reagent were largely deviated from the ideal range. Also, as shown in FIG. 18A, the FVIII activity values converted from the coagulation time obtained by using each of 3-fold diluted reagents were also largely deviated from the ideal range. In addition, many of the FVIII activity values from |Min 1|, |Min 2| and Max 2 obtained using each undiluted reagent were deviated from the ideal range at an ACE910 concentration of 10 to 100 μg/mL. Accordingly, it was shown difficult to appropriately evaluate the coagulability of the blood specimen containing ACE910 with the commercially available APTT reagent. Meanwhile, as shown in FIGS. 18B to 18D, many of the FVIII activity values from |Min 1|, |Min 2| and Max 2 obtained by using each of 3-fold diluted reagents were included in the ideal range at an ACE910 concentration of 10 to 100 μg/mL. Accordingly, it was shown that the coagulability of a blood specimen containing a substance having a FVIII-substituting activity can be appropriately evaluated by diluting the commercial APTT reagent.

Example 3

Whether or not the coagulability could be appropriately evaluated, even a blood specimen containing both a substance having a FVIII-substituting activity and FVIII, by the diluted APTT measuring reagent was investigated.

(1) Reagent

As the commercially available APTT measuring reagent, Thrombocheck APTT-SLA (Sysmex Corporation) was used. This APTT measuring reagent and Owren's Veronal buffer (Sysmex Corporation) were mixed in a ratio of reagent:buffer of 1:2 expressed by a volume ratio to prepare a reagent for blood coagulation analysis (corresponding to a reagent of 3-fold dilution of Thrombocheck APTT-SLA). As a coagulation initiation reagent containing calcium ions, a 20 mM calcium chloride solution (Sysmex Corporation) was used.

(2) Blood Specimen

The bispecific antibody ACE910 was added to FVIII-deficient human plasma (George King Bio-Medical) to a concentration of 0, 0.3, 1, 3, 10, 30, 100 or 300 μg/mL to prepare blood specimens containing a substance having a FVIII-substituting activity. Three additional sets of series of blood specimens containing ACE910 at various concentrations were prepared, and recombinant human FVIII (rhFVIII, Bayer Co., Ltd.) was added to each set so as to have a concentration of 1 or 5 IU/dL to prepare blood specimens containing both ACE910 and FVIII. Also, as a specimen for preparing a calibration curve, blood specimens obtained by adding recombinant human FVIII (rhFVIII, Bayer Co., Ltd.) to FVIII-deficient human plasma (George King Bio-Medical) so as to have a concentration of 0, 1, 3, 10, 30, 100 or 200 IU/dL were prepared.

(3) Preparation and Measurement of Measurement Sample

Preparation and measurement of the measurement sample were carried out in the same manner as in Example 1. In the measurement sample, the final concentration of ellagic acid is 9.6 μM, and the final concentration of phospholipids is 14.4 μM.

(4) Analysis Results

|Min 1|, |Min 2| and Max 2 were calculated as parameters on differentiation of coagulation waveform, based on the temporal change in the resulting transmittance, and plotted on a graph. The resulting graphs are shown in FIGS. 19A, 20A and 21A, respectively. |Min 1|, |Min 2| and Max 2 of each blood specimen were converted into FVIII activity values, using the graphs of the blood specimens containing rhFVIII as calibration curves, to create graphs from the resulting converted values. The resulting graphs are shown in FIGS. 19B, 20B and 21B, respectively. As shown in these graphs, even in the presence of FVIII, a change in parameter value dependent on ACE910 concentration was observed. Accordingly, it was shown that the coagulability can be appropriately evaluated, even a blood specimen containing both a substance having a FVIII-substituting activity and FVIII, by adjusting the concentrations of the activators of the APTT measuring reagent and the phospholipids by dilution.

Example 4

(1) Coagulation Waveform Analysis of Bispecific Antibody in FVIII-Deficient Plasma Using Coagulation Initiation Reagent Composed of Ellagic Acid and Phospholipids To 50 μL of factor VIII (FVIII) deficient human plasma (George King Bio-Medical, Lot No. 899-3062, 895-2757, 899-2847) added with bispecific antibody ACE910 or recombinant human FVIII (rhFVIII, Bayer Co., Ltd.) was added 50 μL of each of reagents 1 to 3 for blood coagulation analysis composed of ellagic acid and phospholipids. After incubation for 3 minutes, 50 μL of a 0.02 mol/L calcium chloride solution was added thereto to start a coagulation reaction, and measurement was performed with an automatic blood coagulation measuring device CS-2000i (Sysmex Corporation). The respective final concentrations of ellagic acid and phospholipids in the measurement sample were shown in Table 2 below. Incidentally, reagents 1 to 3 for blood coagulation analysis are denoted as Reagent 1 to Reagent 3 in FIGS. 22 to 24, respectively.

TABLE 2

Reagent for blood coagulation analysis composed of ellagic acid and phospholipids

|  | Ellagic acid | Phospholipid |
|---|---|---|
| Reagent 1 for blood coagulation analysis | 29 μM | 43 μM |
| Reagent 2 for blood coagulation analysis | 29 μM | 4.3 μM |
| Reagent 3 for blood coagulation analysis | 2.9 μM | 43 μM |

Each concentration of ellagic acid and phospholipids in Table 2 was described as the final concentration after mixing the plasma, the reagent for blood coagulation analysis, and the calcium chloride solution (final concentration in the measurement sample).

(2) Coagulation waveform analysis of bispecific antibody in FVIII-deficient plasma using reagent for blood coagulation analysis composed of tissue factor, ellagic acid and phospholipids To 50 μL of FVIII-deficient human plasma (George King Bio-Medical, Lot No. 899-3062, 895-3394) added with ACE910 or recombinant human FVIII (rhFVIII, Bayer Co., Ltd.) was added 50 μL of each of reagents 4 to 16 for blood coagulation analysis composed of tissue factor, ellagic acid and phospholipids. After incubation for 3 minutes, 50 μL of a 0.02 mol/L calcium chloride solution was added thereto to start a coagulation reaction, and measurement was performed with an automatic blood coagulation measuring device CS-2000i (Sysmex Corporation). The respective final concentrations of tissue factor, ellagic acid and phospholipids in the measurement sample were shown in Table 3 below.

Incidentally, reagents 4 to 15 for blood coagulation analysis are denoted as Reagent 4 to Reagent 15 in FIGS. 25 to 29, respectively.

TABLE 3

Reagent for blood coagulation analysis composed of tissue factor, ellagic acid and phospholipids

|  | Tissue factor | Ellagic acid | Phospholipid |
|---|---|---|---|
| Reagent 4 for blood coagulation analysis | 7.3 ng/mL | 26 μM | 43 μM |
| Reagent 5 for blood coagulation analysis | 0.13 ng/mL | 0.86 μM | 13 μM |
| Reagent 6 for blood coagulation analysis | 0.044 ng/mL | 0.86 μM | 13 μM |
| Reagent 7 for blood coagulation analysis | 0.015 ng/mL | 0.86 μM | 13 μM |
| Reagent 8 for blood coagulation analysis | 0.0049 ng/mL | 0.86 μM | 13 μM |
| Reagent 9 for blood coagulation analysis | 0.002 ng/mL | 0.86 μM | 13 μM |
| Reagent 10 for blood coagulation analysis | 0.044 ng/mL | 0.29 μM | 13 μM |
| Reagent 11 for blood coagulation analysis | 0.015 ng/mL | 0.29 μM | 13 μM |
| Reagent 12 for blood coagulation analysis | 0.0049 ng/mL | 0.29 μM | 13 μM |
| Reagent 13 for blood coagulation analysis | 0.002 ng/mL | 0.29 μM | 13 μM |
| Reagent 14 for blood coagulation analysis | 0.0049 ng/mL | 0.10 μM | 13 μM |
| Reagent 15 for blood coagulation analysis | 0.002 ng/mL | 0.10 μM | 13 μM |
| Reagent 16 for blood coagulation analysis | 0.0049 ng/mL | 0.15 μM | 13 μM |

Each concentration of tissue factor, ellagic acid and phospholipids in Table 3 was described as the final concentration after mixing the plasma, the reagent for blood coagulation analysis, and the calcium chloride solution (final concentration in the measurement sample).

(3) Coagulation Waveform Analysis of Bispecific Antibody in FVIII-Deficient Plasma in the Presence of FVIII Using Agent for Blood Coagulation Analysis Containing Ellagic Acid and Phospholipids To 50 μL of a sample obtained by adding ACE910 to FVIII-deficient human plasma (George King Bio-Medical, Lot No. 899-3062) added with 1, 5 or 20 U/dL recombinant human FVIII (rhFVIII, Bayer Co., Ltd.) was added 50 μL of a reagent for blood coagulation analysis (reagent 3 for blood coagulation analysis in Table 2) composed of ellagic acid and phospholipids. After incubation for 3 minutes, 50 μL of a 0.02 mol/L calcium chloride solution was added thereto to start a coagulation reaction, and measurement was performed with an automatic blood coagulation measuring device CS-2000i (Sysmex Corporation).

(4) Coagulation waveform analysis of bispecific antibody in FVIII-deficient plasma in the presence of FVIII using agent for blood coagulation analysis containing tissue factor, ellagic acid and phospholipids To 50 μL of a sample obtained by adding ACE910 to FVIII-deficient human plasma (George King Bio-Medical, Lot No. 899-3394) added with 1, 5, 20, 50, 100, or 200 U/dL recombinant human FVIII (rhFVIII, Bayer Co., Ltd.) was added 50 μL of a reagent for blood coagulation analysis (reagent 12 or 16 for blood coagulation analysis in Table 3) composed of tissue factor, ellagic acid and phospholipids. After incubation for 3 minutes, 50 μL of a 0.02 mol/L calcium chloride solution was added thereto to start a coagulation reaction, and measurement was performed with an automatic blood coagulation measuring device CS-2000i (Sysmex Corporation).

Results

<Reagent for Blood Coagulation Analysis Composed of Ellagic Acid and Phospholipids>

Each concentration of ellagic acid and phospholipids contained in reagent 1 for blood coagulation analysis is the same as that of ellagic acid and phospholipids contained in Thrombocheck which is a commercially available APTT measuring reagent. Reagent 2 for blood coagulation analysis is a reagent in which the phospholipid concentration is diluted to 1/10 without changing the ellagic acid concentration, and reagent 3 for blood coagulation analysis is a reagent in which the ellagic acid concentration is diluted to 1/10 without changing the phospholipid concentration. In any of reagents 1, 2 and 3 for blood coagulation analysis, the coagulation rate in FVIII-deficient plasma each containing rhFVIII and ACE910, and coagulation acceleration were increased (see FIGS. 22A and 22B, FIGS. 23A and 23B, and FIGS. 24A and 24B). Meanwhile, the case where a value obtained by converting each of |Min 1| and |Min 2| of the specimen containing 10, 30 or 100 μg/mL ACE910 from the calibration curves of |Min 1| and |Min 2| of the specimen containing rhFVIII into FVIII activity fell in the expected ideal range (0.2 to 0.4 U/dL FVIII per 1 μg/mL ACE910) for its haemostatic effect was only when reagent 3 for blood coagulation analysis was used (see FIGS. 22C and 22D, FIGS. 23C and 23D, and FIGS. 24C and 24D. In the figures, a region sandwiched between two broken lines shows the ideal range). When using reagent 3 for blood coagulation analysis, two or more of the 10, 30, or 100 μg/mL FVIII activity values converted from |Min 1| of the specimen containing ACE910 fell in the ideal range. From these results, it was shown that the commercially available APTT reagent (reagent 1 for blood coagulation analysis) overestimates the efficacy of ACE910, whereas reagent 3 for blood coagulation analysis can properly monitor the efficacy of ACE910.

Furthermore, as an example, when the effect of ACE910 in FVIII-deficient plasma containing a FVIII preparation was evaluated using reagent 3 for blood coagulation analysis, the coagulation rate and the coagulation acceleration increased by addition of ACE910 (see FIGS. 30A to 30E). From these results, it was shown that the efficacy of ACE910 can be monitored even in the presence of FVIII, by using a reagent for blood coagulation analysis composed of ellagic acid and phospholipids at concentrations like reagent 3 for blood coagulation analysis.

<Reagent for Blood Coagulation Analysis Composed of Tissue Factor, Ellagic Acid and Phospholipids>

Reagents 4 to 16 for blood coagulation analysis are reagents prepared so that the tissue factor, ellagic acid and phospholipids each have various concentrations. The coagulation time, coagulation rate and acceleration of ACE910 increased, even under conditions using any of reagents 4 to 16 for blood coagulation analysis (see FIGS. 25A to 25C, FIGS. 26A to 26I, FIGS. 27A to 27I, and FIGS. 32A to 32C).

Based on the above, it was shown that the efficacy of ACE910 can be monitored by using a reagent for blood coagulation analysis composed of tissue factor, ellagic acid and phospholipids. Here, as an example, it was shown that a value obtained by converting the coagulation rate of 10, 30 or 100 μg/mL ACE910 from the calibration curve of |Min 1| of the specimen containing rhFVIII into FVIII activity falls in the expected ideal range (0.2 to 0.4 U/dL FVIII per 1 μg/mL ACE910) for its haemostatic effect, by using reagents 4, 6, 11, 12 and 15 for blood coagulation analysis (see FIGS. 28 and 29. In the figures, a region sandwiched between two broken lines shows the ideal range).

Furthermore, as an example, when the effect of ACE910 in FVIII-deficient plasma containing a FVIII preparation was evaluated each using reagents 12 and 16 for blood coagulation analysis, the coagulation rate and the coagulation acceleration increased by addition of ACE910 (see FIGS. 31A to 31K and FIGS. 32A to 32C). From these results, it was shown that the efficacy of ACE910 can be monitored even in the presence of FVIII, by using a reagent for blood coagulation analysis composed of tissue factor, ellagic acid and phospholipids.

Example 5

Coagulation Waveform Analysis of Bispecific Antibody in FVIII-Deficient Plasma Using Reagent Kit for Blood Coagulation Analysis Containing Tissue Factor, Ellagic Acid and Phospholipids In Example 5, reagent kits 17 to 34 for blood coagulation analysis composed of a first reagent containing ellagic acid and phospholipids and a second reagent containing tissue factor and a calcium chloride solution (0.02 mol/L) were used. 50 μL of the first reagent was added to 50 μL of FVIII-deficient human plasma (George King Bio-Medical) added with ACE910 or recombinant human FVIII (rhFVIII, Bayer Co., Ltd.). After incubation for 3 minutes, 50 μL of the second reagent was added thereto to start a coagulation reaction, and measurement was performed with an automatic blood coagulation measuring device CS-5100 (Sysmex Corporation). The respective final concentrations of each of tissue factor, ellagic acid and phospholipids in the measurement sample prepared using reagent kits 17 to 34 for blood coagulation analysis were shown in Table 4 below. Reagent kits 17 to 34 for blood coagulation analysis are denoted as Reagent 17 to Reagent 34 in FIGS. 33 to 37, respectively.

TABLE 4

Reagent kit for blood coagulation analysis composed of first reagent containing ellagic acid and phospholipids and second reagent containing tissue factor and calcium chloride

|  | Ellagic acid (First reagent) | Phospholipid (First reagent) | Tissue factor (Second reagent) |
|---|---|---|---|
| Reagent kit 17 for blood coagulation analysis | 2.9 μM | 13 μM | 0.15 ng/mL |
| Reagent kit 18 for blood coagulation analysis | 0.26 μM | 13 μM | 0.49 ng/mL |
| Reagent kit 19 for blood coagulation analysis | 0.78 μM | 13 μM | 0.49 ng/mL |
| Reagent kit 20 for blood coagulation analysis | 2.9 μM | 13 μM | 0.49 ng/mL |
| Reagent kit 21 for blood coagulation analysis | 9.6 μM | 13 μM | 0.49 ng/mL |
| Reagent kit 22 for blood coagulation analysis | 0.78 μM | 13 μM | 1.5 ng/mL |
| Reagent kit 23 for blood coagulation analysis | 2.9 μM | 13 μM | 1.5 ng/mL |
| Reagent kit 24 for blood coagulation analysis | 9.6 μM | 13 μM | 1.5 ng/mL |
| Reagent kit 25 for blood coagulation analysis | 2.9 μM | 13 μM | 4.9 ng/mL |
| Reagent kit 26 for blood coagulation analysis | 9.6 μM | 13 μM | 4.9 ng/mL |
| Reagent kit 27 for blood coagulation analysis | 0.26 μM | 0.39 μM | 0.015 ng/mL |
| Reagent kit 28 for blood coagulation analysis | 0.26 μM | 0.39 μM | 0.044 ng/mL |
| Reagent kit 29 for blood coagulation analysis | 0.78 μM | 1.2 μM | 0.044 ng/mL |
| Reagent kit 30 for blood coagulation analysis | 0.78 μM | 1.2 μM | 0.15 ng/mL |

TABLE 4-continued

Reagent kit for blood coagulation analysis composed of first reagent containing ellagic acid and phospholipids and second reagent containing tissue factor and calcium chloride

|  | Ellagic acid (First reagent) | Phospholipid (First reagent) | Tissue factor (Second reagent) |
| --- | --- | --- | --- |
| Reagent kit 31 for blood coagulation analysis | 2.9 µM | 4.3 µM | 0.15 ng/mL |
| Reagent kit 32 for blood coagulation analysis | 0.78 µM | 1.2 µM | 0.49 ng/mL |
| Reagent kit 33 for blood coagulation analysis | 2.9 µM | 4.3 µM | 0.49 ng/mL |
| Reagent kit 34 for blood coagulation analysis | 2.9 µM | 4.3 µM | 1.5 ng/mL |

Each concentration of tissue factor, ellagic acid, and phospholipids in Table 4 was described as the final concentrations after mixing the plasma, the first reagent, and the second reagent (final concentrations in the measurement sample).

The coagulation rate and acceleration of ACE910 increased, even under conditions using any of reagent kits 17 to 34 for blood coagulation analysis (see FIGS. 33A to 33E, FIGS. 34A to 34E, and FIGS. 35A to 35E). Based on the above, it was shown that the efficacy of ACE910 can be monitored by using a reagent for blood coagulation analysis composed of tissue factor, ellagic acid and phospholipids. Here, as an example, it was shown that a value obtained by converting the coagulation rate of 10, 30 or 100 µg/mL ACE910 from the calibration curve of |Min 1| of the specimen containing rhFVIII into FVIII activity falls in the expected ideal range (0.2 to 0.4 U/dL FVIII per 1 µg/mL ACE910) for its haemostatic effect, by using reagent kits 19, 20, 23, 24, 28, 30, 32, 33 and 34 for blood coagulation analysis (see FIGS. 36A and 36B. In the figures, a region sandwiched between two broken lines shows the ideal range).

In addition, as an example, it was shown that a value obtained by converting the coagulation rate of 10, 30 or 100 µg/mL ACE910 from the calibration curve of |Min 2| of the specimen containing rhFVIII into FVIII activity falls in the expected ideal range (0.2 to 0.4 U/dL FVIII per 1 µg/mL ACE910) for its haemostatic effect, by using reagent kits 22, 23 and 34 for blood coagulation analysis (see FIGS. 37A and 37B. In the figures, a region sandwiched between two broken lines shows the ideal range).

Example 6

Coagulation Waveform Analysis of Bispecific Antibody in FVIII-Deficient Plasma in the Presence of Bypass Preparation Using Reagent Kit for Blood Coagulation Analysis Containing Tissue Factor, Ellagic Acid and Phospholipids In Example 6, reagent kits 20, 21, 28, 30, 33, 35 and 36 for blood coagulation analysis composed of a first reagent containing ellagic acid and phospholipids and a second reagent containing tissue factor and a calcium chloride solution (0.02 mol/L) were used. Reagent kits 20, 21, 28, 30 and 33 are the same as in Example 5. To 50 µL of a sample obtained by adding ACE910 to FVIII-deficient human plasma (George King Bio-Medical) added with 0.5 or 1.0 U/mL APCC (Fiber (registered trademark), Baxter Limited) or FVIII-deficient human plasma (George King Bio-Medical) added with 0.25 or 1.0 µg/mL FVIIa (NovoSeven (registered trademark), Novo Nordisk Pharma Ltd.) was added 50 µL of the first reagent. After incubation for 3 minutes, 50 µL of the second reagent was added thereto to start a coagulation reaction, and measurement was performed with an automatic blood coagulation measuring device CS-2000i (Sysmex Corporation). The respective final concentrations of the tissue factor, ellagic acid and phospholipids in the measurement sample prepared using each of the above reagent kits were shown in Table 5 below.

TABLE 5

Reagent kit for blood coagulation analysis composed of first reagent containing ellagic acid and phospholipids and second reagent containing tissue factor and calcium chloride

|  | Ellagic acid (First reagent) | Phospholipid (First reagent) | Tissue factor (Second reagent) |
| --- | --- | --- | --- |
| Reagent kit 20 for blood coagulation analysis | 2.9 µM | 13 µM | 0.49 ng/mL |
| Reagent kit 21 for blood coagulation analysis | 9.6 µM | 13 µM | 0.49 ng/mL |
| Reagent kit 28 for blood coagulation analysis | 0.26 µM | 0.39 µM | 0.044 ng/mL |
| Reagent kit 30 for blood coagulation analysis | 0.78 µM | 1.2 µM | 0.15 ng/mL |
| Reagent kit 33 for blood coagulation analysis | 2.9 µM | 4.3 µM | 0.49 ng/mL |
| Reagent kit 35 for blood coagulation analysis | 0.26 µM | 13 µM | 0.044 ng/mL |
| Reagent kit 36 for blood coagulation analysis | 0.78 µM | 13 µM | 0.15 ng/mL |

Each concentration of tissue factor, ellagic acid, and phospholipids in Table 5 was described as the final concentrations after mixing the plasma, the first reagent, and the second reagent (final concentrations in the measurement sample).

When the effect of ACE910 in FVIII-deficient plasma containing a bypass preparation was evaluated using reagent kits 20, 21, 28, 30, 33, 35 and 36 for blood coagulation analysis, the coagulation rate increased by addition of ACE910 (see FIGS. 38A to 38D for reagent kit 20, FIGS. 39A to 39D for reagent kit 21, FIGS. 40A to 40D for reagent kit 28, FIGS. 41A to 41D for reagent kit 30, FIGS. 42A to 42D for reagent kit 33, FIGS. 43A to 43D for reagent kit 35, and FIGS. 44A to 44D for reagent kit 36). From these results, it was shown that the efficacy of ACE910 can be monitored even in the presence of a bypass preparation, by using a reagent for blood coagulation analysis composed of tissue factor, ellagic acid and phospholipids.

REFERENCE SIGNS LIST

10 Blood Specimen Analyzer
11, 12 Reagent table (reagent accommodating section)
20 Measurement unit
22g, 22i Photodetector (light receiving portion)
27 Lamp unit (light source)
30 Specimen transporting unit
40 Control device (control section)
41 Display unit
42 Input unit
43 Computer body
50 Measurement device (measurement sample preparing section and optical information acquiring section)
111 First container
112 Second container
113 Third container

The invention claimed is:

1. A method for evaluating coagulability of a blood specimen, the method comprising the steps of:
   preparing a measurement sample by mixing: a blood specimen obtained from a subject to whom a bispecific antibody specifically binding to (i) FIX or FIXa and (ii) FX is administered; a coagulation factor XII-activating agent; phospholipids; and a calcium ion-containing aqueous solution;
   irradiating the measurement sample with light to acquire optical information on the light amount from the measurement sample;
   acquiring at least one parameter on differentiation of coagulation waveform based on the acquired optical information; and
   evaluating coagulability of the blood specimen based on the value of the acquired parameter,
   wherein
   a final concentration of the coagulation factor XII-activating agent is 1 µM or more and 2.9 µM or less and a final concentration of the phospholipids is 1.4 µM or more and 43 µM or less in the measurement sample.

2. The method according to claim 1, wherein, in the evaluation step, a value indicating coagulability of the blood specimen containing the substance having a coagulation factor VIII-substituting activity is acquired from the value of the acquired parameter, and the coagulability of the blood specimen is evaluated based on the acquired value indicating coagulability.

3. The method according to claim 2, wherein the value indicating coagulability is a coagulation factor VIII activity value.

4. The method according to claim 1, wherein the optical information is a scattered light amount, a transmittance or an absorbance measured continuously or intermittently, and the coagulation waveform is a waveform representing a temporal change of the scattered light amount, the transmittance, or the absorbance.

5. The method according to claim 1, wherein the parameter on differentiation of coagulation waveform is at least one selected from the group consisting of maximum coagulation rate (|Min 1|), maximum coagulation acceleration (|Min 2|), maximum coagulation deceleration (Max 2), area under the waveform (AUC), and slope.

6. The method according to claim 1, wherein the coagulation factor XII-activating agent is at least one selected from ellagic acid, kaolin, celite, and silica.

7. A method for evaluating coagulability of a blood specimen, the method comprising the steps of
   preparing a measurement sample by mixing: a blood specimen obtained from a subject to whom a bispecific antibody specifically binding to (i) FIX or FIXa and (ii) FX is administered; a coagulation factor XII-activating agent; phospholipids; tissue factor; and a calcium ion-containing aqueous solution;
   irradiating the measurement sample with light to acquire optical information on the light amount from the measurement sample; and
   evaluating coagulability of the blood specimen based on the acquired optical information.

* * * * *